US008153384B2

(12) United States Patent
Friedman et al.

(10) Patent No.: US 8,153,384 B2
(45) Date of Patent: Apr. 10, 2012

(54) MARKS AS MODIFIERS OF THE P53 PATHWAY AND METHODS OF USE

(75) Inventors: Lori Friedman, San Carlos, CA (US); Gregory D. Plowman, San Carlos, CA (US); Helen Francis-Lang, San Francisco, CA (US); Danxi Li, San Francisco, CA (US); Roel P. Funke, South San Francisco, CA (US); Marcia Belvin, Albany, CA (US); Mario N. Lioubin, San Mateo, CA (US)

(73) Assignee: Exelixis, Inc., South San Francisco, CA (US)

( * ) Notice: Subject to any disclaimer, the term of this patent is extended or adjusted under 35 U.S.C. 154(b) by 0 days.

(21) Appl. No.: 12/802,748

(22) Filed: Jun. 10, 2010

(65) Prior Publication Data

US 2010/0325743 A1 Dec. 23, 2010

Related U.S. Application Data

(63) Continuation of application No. 11/627,976, filed on Jan. 28, 2007, now abandoned, which is a continuation of application No. 10/161,565, filed on Aug. 2, 2002, now abandoned.

(60) Provisional application No. 60/296,076, filed on Jun. 5, 2001, provisional application No. 60/328,605, filed on Oct. 10, 2001, provisional application No. 60/357,253, filed on Feb. 15, 2002.

(51) Int. Cl.
*G01N 33/53* (2006.01)
*G01N 33/574* (2006.01)
*C12Q 1/00* (2006.01)

(52) U.S. Cl. ............................ 435/7.1; 435/6; 435/7.23
(58) Field of Classification Search ........................ None
See application file for complete search history.

(56) References Cited

U.S. PATENT DOCUMENTS

| 5,863,729 A | 1/1999 | Piwnica-Worms |
| 6,165,461 A | 12/2000 | Cobb et al. |

FOREIGN PATENT DOCUMENTS

| WO | WO 98/01756 A1 | 1/1998 |
| WO | WO 96/13592 A2 | 5/1998 |
| WO | WO 00/55178 A1 | 9/2000 |
| WO | WO 00/73469 A2 | 12/2000 |
| WO | WO 01/09345 A1 | 2/2001 |
| WO | WO 01/38530 A2 | 5/2001 |
| WO | WO 01/57190 A2 | 8/2001 |
| WO | WO 01/70979 * | 9/2001 |
| WO | WO 01/88108 A1 | 11/2001 |
| WO | WO 01/90160 A2 | 11/2001 |
| WO | WO 01/96547 A2 | 12/2001 |
| WO | WO 02/10402 A2 | 2/2002 |
| WO | WO 03/033708 | 4/2003 |

OTHER PUBLICATIONS

Tockman et al (Cancer Res., 1992, 52:2711s-2718s).*
Kato et al (Neoplasia, Jan./Feb. 2001, 3:4-9).*
Schumacher et al.: "The *C. elegans* homology of the p53 tumor suppressor is required for DNA damage-induced apoptosis," Current Biology, 2001, 11:1722-1727.
Ollman et al.: "*Drosophila* p53 Is a Structural and Functional homolog of the Tumor suppressor p53," Cell, 2000. 101:91-101.
Bowie et al.: "Deciphering the message in protein sequences: Tolerance to amino acids solutions," Science, 1990, 247:1306-1310.
Schultz, S. J. et al.: "*Homosapiens* ELKL motif kinase (EMK1), transcript variant 1, mRNA," Genbank GI No. 9845486, Feb. 3, 2001.
Schultz,S J et al *Homo sapiens* ELKL motif kinase (EMK1), transcript variant 1, mRNA. Genbank GI No. 0845486. Feb. 3, 2001.
Schultz,S.J. et al., "*Homo sapiens* ELKL motif kinase (EMK1), transcript variant 2, mRNA." Genbank GI No. 9845488, Feb. 3, 2001.
NCB Annotation Project, "*Homo sapiens* ELKL motif kinase (EMK1), mRNA." Genbank GI No. 18578044, Feb. 7, 2002.
Strausberg,R., "*Homo sapiens*, Similar to ELKL motif kinase," clone MGC:1466 Image:3139103, mRNA, complete cds. Genbank GI No. 14250621, Jul. 12, 2001.
Sun,T.Q., et al., "*Homo sapiens* Ser/Thr protein kinase PAR-1Balpha mRNA, complete cds." Genbank GI No. 15042610,Dec. 27, 2001.
Drewes,G., et al., "*Homo sapiens* MAP/microtubule affinity-regulating kinase 1 (MARK1), mRNA." Genbank GI No. 8923921, Feb. 10, 2002.
NCB Annotation Project.. *Homo sapiens* MAP/microlubule affinity-regulating kinase 1 (MARK1), mRNA., Genbank GI No. 17445805, Feb. 6, 2002.
Nagase,T.. et al., "*Homo sapiens* mRNA for KIAA1477 protein, partial cds." Genbank GI No. 7959214, Feb. 22, 2001.
Isogai,T., et al., *Homo sapiens* cDNA FLJ14587 fis, clone NT2RM4001758, moderately similar to Putative Serine/Threonine-Protein Kinase EMI< (EC 2.7.14, Genbank GI No. 14042208, May 15, 2001.
Peng,C.Y., et al., "*Homo sapiens* Cdc25C associated protein kinase C-TAK1 mRNA, complete cds," Genbank GI No. 3089348, Apr. 29, 1998. Ono T, et al., "*Homo sapiens* MAP/microtubute affinity-regulating kinase 3 (MARK3), mRNA." Genbank GI No. 4505102, 31.00T-2000.
Waggoner,S N., et al., "*Homo sapiens* serine/threonine protein kinase Kp78 splice variant CTAK75a mRNA, complete cds," Genbank GI No. 5714035, Sep. 21, 2001.
Drewes,G., "*Homo sapiens* MAP/microtubule affinity-regulating kinase 3 long isoform (MARK3) mRNA, complete cds; alternatively spliced," Genbank GI No. 19448970, Jan. 31, 2002.
Kato,T., et al, "*Homo sapiens* MARKL1 mRNA for MAP/microtubule affinity-regulating kinase like 1, complete cds." Genbank GI No. 13366083, Apr. 10, 2001.
Nagase,T., et al., "*Homo sapiens* mRNA for KIAA1860 protein, partial cds." Genbank GI No. 14017936, Jun. 5, 2001.
Drewes,G., et al., "*Homo sapiens* MARK4 serine/threonine protein kinase mRNA, complete cds." Genbank GI No. 16555377, Oct. 31, 2001.
Schultz,S.J et al., "ELKL motif kinase 1 isoform a; ELKL motif kinase 1 [*Homo sapiens*]." Genbank GI No. 9845487, Feb. 3, 2001.

(Continued)

*Primary Examiner* — Laura B Goddard
(74) *Attorney, Agent, or Firm* — McDonnell Boehnen Hulbert & Berghoff LLP

(57) ABSTRACT

Human MARK genes are identified as modulators of the p53 pathway, and thus are therapeutic targets for disorders associated with defective p53 function. Methods for identifying modulators of p53, comprising screening for agents that modulate the activity of MARK are provided.

15 Claims, No Drawings

OTHER PUBLICATIONS

Drewes et al.: "MARK, a novel family of protein kinases that phosphorylate microtubule-asscoiated proteins and trigger microtubule disruption," Cell, Apr. 18, 1007, vol. 89, pp. 297-308.

Drewes,G., et al., "MAP/microtubule affinity-regulating kinase 1 [*Homo sapiens*]." Genbank GI No. 8923922, Feb. 10, 2002.

Peng,C.Y., et al., "Cdc25C associated protein kinase C-TAK1 [*Homo sapiens*]." Genbank GI No. 3089349, Apr. 28, 1998.

Ono T, el al, "MAP/microtubule affinity-regulating kinase 3 [*Homo sapiens*)." Genbank GI No. 4505103, Oct. 31, 2000.

Kato,T., et at.,'MAP/microtubule affinity-regulating kinase like 1 [*Homo sapiens*].' Genbank GI No. 13366084, Apr. 10, 2001.

Drewes,G., et al., "MAP/microtubule affinity-regulating kinase like 1; MARK4 serine/threonine protein kinase (*Homo sapiens*)." Genbank GI No. 13899225, Nov. 30, 2001.

Tassan et al., Biology of the Cell, 2004, 96-193-199.

NCBI "Ace View" (p. 1-2) printed Nov. 24, 2009.

Waggoner, S.N. et al.: "*Homo sapiens* serine/therone protein kinase Kp78 splice variant CTAK75a mRNA, complete cds," GenBank GI No. 5714635, Sep. 21, 2001.

Drewes, G.: "*Homo sapiens* MAP/microtubule affinity-regulating kinase 3 long isoform (MARK3) mRNA complete cds; alternatively spliced," GenBank GI No. 18448970, Jan. 31, 2002.

\* cited by examiner

SEQUENCE LISTING

<160> NUMBER OF SEQ ID NOS: 29

<210> SEQ ID NO 1
<211> LENGTH: 2946
<212> TYPE: DNA
<213> ORGANISM: Homo sapiens

<400> SEQUENCE: 1

```
tcctggaatt gcacgcgctt cctgaccacc aggctctggc ccttgagaag ccagcggggc      60
tttgtccctg ttgctctcct tgccaaaccc agtctctctg ctagtggtgg tttcggttgc     120
gacaccgtcc aggttcccag gcaggaaccg ctcggcctgg ctgcttagct acttttcact     180
gaggaggtgg tggaaggtgt cgcctgctct ggctgagtaa gggtggctgg ctgagccggc     240
agcccccgcc ctaggcctgg ctcttcccgg cctctgtact ttgccctcgc tgcctgacag     300
gttctgctgt gggctctgct gaatggaagt cgctggtagt ccttttccct ttctccagtc     360
ggcccacctt gggacacctt gactccaagc ccagcagtaa gtccaacatg attcggggcc     420
gcaactcagc cacctctgct gatgagcagc cccacattgg aaactaccgg ctcctcaaga     480
ccattggcaa gggtaatttt gccaaggtga agttggcccg acacatcctg actgggaaag     540
aggtagctgt gaagatcatt gacaagactc aactgaactc ctccagcctc cagaaactat     600
tccgcgaagt aagaataatg aaggttttga atcatcccaa catagttaaa ttatttgaag     660
tgattgagac tgagaaaacg ctctaccttg tcatggagta cgctagtggc ggagaggtat     720
ttgattacct agtggctcat ggcaggatga agaaaaaga ggctcgagcc aaattccgcc     780
agatagtgtc tgctgtgcag tactgtcacc agaagtttat tgtccataga gacttaaagg     840
cagaaaacct gctcttggat gctgatatga acatcaagat tgcagacttt ggcttcagca     900
atgaattcac ctttgggaac aagctggaca ccttctgtgg cagtcccccct tatgctgccc     960
cagaactctt ccagggcaaa aaatatgatg acccgaggg ggatgtgtgg agcctaggag    1020
ttatcctcta tactggtc agcggatccc tgccttttga tggacagaac ctcaaggagc    1080
tgcgggaacg ggtactgagg gggaaatacc gtattccatt ctacatgtcc acggactgtg    1140
aaaacctgct taagaaattt ctcatcctta atcccagcaa gagaggcact ttagagcaaa    1200
tcatgaaaga tcgatggatg aatgtgggtc acgaagatga tgaactaaag ccttacgtgg    1260
agccactccc tgactacaag gaccccccggc ggacagagct gatggtgtcc atgggttata    1320
cacgggaaga gatccaggac tcgctggtgg gccagagata caacgaggtg atggccacct    1380
atctgctcct gggctacaag agctccgagc tggaaggcga caccatcacc ctgaaaccc    1440
ggccttcagc tgatctaacc aatagcagcg cccaattccc atcccacaag gtacagcgaa    1500
gcgtgtcggc caatcccaag cagcggcgct tcagcgacca ggctggtcct gccattccca    1560
cctctaattc ttactctaag aagactcaga gtaacaacgc agaaaataag cggcctgagg    1620
aggaccggga gtcagggcgg aaagccagca gcacagccaa ggtgcctgcc agcccctgc    1680
```

```
ccggtctgga gaggaagaag accaccccaa cccctccac gaacagcgtc ctctccacca    1740
gcacaaatcg aagcaggaat tccccacttt tggagcgggc cagcctcggc caggcctcca    1800
tccagaatgg caaagacagc ctaaccatgc cagggtcccg ggcctccacg gcttctgctt    1860
ctgccgcagt ctctgcggcc cggccccgcc agcaccgaaa atccatgtcg gcctccgtgc    1920
accccaacaa ggcctctggg ctgcccccca cggagagtaa ctgtgaggtg ccgcggccca    1980
gcacagcccc ccagcgtgtc cctgttgcct ccccatccgc ccacaacatc agcagcagtg    2040
gtggagcccc agaccgaact aacttccccc ggggtgtgtc cagccgaagc accttccatg    2100
ctgggcagct ccgacaggtg cgggaccagc agaatttgcc ctacggtgtg accccagcct    2160
ctccctctgg ccacagccag ggccggcggg gggcctctgg gagcatcttc agcaagttca    2220
cctccaagtt tgtacgcagg aacctgaatg aacctgaaag caaagaccga gtggagacgc    2280
tcagacctca cgtggtgggc agtggcggca cgacaaaga aaaggaagaa tttcgggagg    2340
ccaagccccg ctccctccgc ttcacgtgga gtatgaagac cacgagctcc atggagccca    2400
acgagatgat gcgggagatc cgcaaggtgc tggacgcgaa cagctgccag agcgagctgc    2460
atgagaagta catgctgctg tgcatgcacg gcacgccggg ccacgaggac ttcgtgcagt    2520
gggagatgga ggtgtgcaaa ctgccgcggc tctctctcaa cggggttcga tttaagcgga    2580
tatcgggcac ctccatggcc ttcaaaaaca ttgcctccaa aatagccaac gagctgaagc    2640
tttaacaggc tgccaggagc gggggcggcg ggggcgggcc agctggacgg gctgccggcc    2700
gtgcgccgcc ccacctgggc gagactgcag cgatggattg tgtgtctcc ctgctggcac    2760
ttctcccctc cctggcccct tcagttttc tcccacattc acccctgccc agagattccc    2820
ccttctcctc tccctactg gaggcaaagg aaggggaggg tggatggggg ggcagggctc    2880
cccctcggta ctgcggttgc acagagtatt tcgcctaaac caagaaattt tttattacca    2940
aaaaga                                                              2946
```

<210> SEQ ID NO 2
<211> LENGTH: 2784
<212> TYPE: DNA
<213> ORGANISM: Homo sapiens

<400> SEQUENCE: 2

```
tcctggaatt gcacgcgctt cctgaccacc aggctctggc ccttgagaag ccagcggggc      60
tttgtccctg ttgctctcct tgccaaaccc agtctctctg ctagtggtgg tttcggttgc     120
gacaccgtcc aggttcccag gcaggaaccg ctcggcctgg ctgcttagct acttttcact     180
gaggaggtgg tggaaggtgt cgcctgctct ggctgagtaa gggtggctgg ctgagccggc     240
agccccgcc ctaggcctgg ctcttcccgg cctctgtact ttgccctcgc tgcctgacag     300
gttctgctgt gggctctgct gaatggaagt cgctggtagt cctttcccct ttctccagtc     360
ggcccacctt gggacacctt gactccaagc ccagcagtaa gtccaacatg attcggggcc     420
gcaactcagc cacctctgct gatgagcagc cccacattgg aaactaccgg ctcctcaaga     480
ccattggcaa gggtaatttt gccaaggtga agttggcccg acacatcctg actgggaaag     540
aggtagctgt gaagatcatt gacaagactc aactgaactc ctccagcctc cagaaactat     600
tccgcgaagt aagaataatg aaggttttga atcatcccaa catagttaaa ttatttgaag     660
tgattgagac tgagaaaacg ctctaccttg tcatggagta cgctagtggc ggagaggtat     720
ttgattacct agtggctcat ggcaggatga agaaaaaga ggctcgagcc aaattccgcc     780
agatagtgtc tgctgtgcag tactgtcacc agaagtttat tgtccataga gacttaaagg     840
```

```
cagaaaacct gctcttggat gctgatatga acatcaagat tgcagacttt ggcttcagca      900
atgaattcac ctttgggaac aagctggaca ccttctgtgg cagtccccct tatgctgccc      960
cagaactctt ccagggcaaa aaatatgatg acccgaggt ggatgtgtgg agcctaggag       1020
ttatcctcta tacactggtc agcggatccc tgccttttga tggacagaac ctcaaggagc      1080
tgcgggaacg ggtactgagg gggaaatacc gtattccatt ctacatgtcc acggactgtg      1140
aaaacctgct taagaaattt ctcatcctta atcccagcaa gagaggcact ttagagcaaa      1200
tcatgaaaga tcgatggatg aatgtgggtc acgaagatga tgaactaaag ccttacgtgg      1260
agccactccc tgactacaag gaccccggc ggacagagct gatggtgtcc atgggttata      1320
cacgggaaga gatccaggac tcgctggtgg gccagagata caacgaggtg atggccacct      1380
atctgctcct gggctacaag agctccgagc tggaaggcga ccatcacc ctgaaacccc       1440 ggccttcagc tgatctaacc aatagcagcg cccaattccc atcccacaag gtacagcgaa      1500
gcgtgtcggc caatcccaag cagcggcgct tcagcgacca ggctggtcct gccattccca      1560
cctctaattc ttactctaag aagactcaga gtaacaacgc agaaaataag cggcctgagg      1620
aggaccggga gtcagggcgg aaagccagca gcacagccaa ggtgcctgcc agcccctgc      1680 ccggtctgga gaggaagaag accacccaa cccctccac gaacagcgtc ctctccacca       1740
gcacaaatcg aagcaggaat tccccacttt tggagcgggc cagcctcggc caggcctcca     1800
tccagaatgg caaagacagc acagccccc agcgtgtccc tgttgcctcc ccatccgccc      1860
acaacatcag cagcagtggt ggagcccag accgaactaa cttccccgg ggtgtgtcca       1920 gccgaagcac cttccatgct gggcagctcc gacaggtgcg ggaccagcag aatttgccct      1980
acggtgtgac cccagcctct ccctctggcc acagccaggg ccggcggggg gcctctggga     2040
gcatcttcag caagttcacc tccaagtttg tacgcaggaa cctgaatgaa cctgaaagca     2100
aagaccgagt ggagacgctc agacctcacg tggtgggcag tggcggcaac gacaaagaaa    2160
aggaagaatt tcgggaggcc aagccccgct ccctccgctt cacgtggagt atgaagacca    2220
cgagctccat ggagcccaac gagatgatgc gggagatccg caaggtgctg acgcgaaca      2280 gctgccagag cgagctgcat gagaagtaca tgctgctgtg catgcacggc acgccgggcc    2340
acgaggactt cgtgcagtgg gagatggaggg tgtgcaaact gccgcggctc tctctcaacg   2400
gggttcgatt taagcggata tcgggcacct ccatggcctt caaaaacatt gcctccaaaa    2460
tagccaacga gctgaagctt taacaggctg ccaggagcgg gggcggcggg ggcgggccag    2520
ctggacgggc tgccggccgt gcgccgcccc acctgggcga gactgcagcg atggattggt    2580
gtgtctccct gctggcactt ctcccctccc tggcccttct cagttttctc ccacattcac    2640
ccctgcccag agattccccc ttctcctctc ccctactgga ggcaaaggaa ggggagggtg    2700 gatgggggg cagggctccc cctcggtact gcggttgcac agagtatttc gcctaaacca    2760
agaaattttt tattaccaaa aaga                                             2784
```

<210> SEQ ID NO 3
<211> LENGTH: 3103
<212> TYPE: DNA
<213> ORGANISM: Homo sapiens
<220> FEATURE:
<221> NAME/KEY: misc_feature
<222> LOCATION: (2941)..(2941)
<223> OTHER INFORMATION: "n" is A, C, G, or T

<400> SEQUENCE: 3

```
cggtggtggc ggccatgttg ggagcagcag gtccggcggc ggctgcctgt gtgccgggcg       60
```

```
cggagcagtg ccgctgaggg caggggagga gcgaggcagg cggccggctg cggcggcaga    120
gagtaggcgg agcggcgcgg cccggccgaa aggcggcaca gcccagccgg gggtcggggg    180
ggtgcggtcc ggagccgctc ggagccggcg cggcctagcc cgagcggcgc atccccgggc    240
tggcgtgagc ggctgcccgg cctcccgca ccccggccg gggcccatgc ggcgggtgct    300
cctgctgtga gaagcccgc ccggccgggc tccgcgcctt cccttccctc ccttcctcca    360
agcttctcgg ttccctcccc cgagataccg cgccatgtc cagcgctcgg accccctac    420 ccacgctgaa cgagagggac acggagcagc ccaccttggg acaccttgac tccaagccca    480
gcagtaagtc caacatgatt cggggccgca actcagccac ctctgctgat gagcagcccc    540
acattggaaa ctaccggctc ctcaagacca ttggcaaggg taattttgcc aaggtgaagt    600
tggcccgaca catcctgact gggaaagagg tagctgtgaa gatcattgac aagactcaac    660
tgaactcctc cagcctccag aaactattcc gcgaagtaag aataatgaag gttttgaatc    720
atcccaacat agttaaatta tttgaagtga ttgagactga gaaaacgctc taccttgtca    780
tggagtacgc tagtggcgga gaggtatttg attacctagt ggctcatggc aggatgaaag    840
aaaaagaggc tcgagccaaa ttccgccaga tagtgtctgc tgtgcagtac tgtcaccaga    900
agtttattgt ccatagagac ttaaaggcag aaaacctgct cttggatgct gatatgaaca    960
tcaagattgc agactttggc ttcagcaatg aattcacctt tgggaacaag ctggacacct   1020
tctgtggcag tccccttat gctgccccag aactcttcca gggcaaaaaa tatgatggac   1080
ccgaggtgga tgtgtggagc ctaggagtta tcctctatac actggtcagc ggatccctgc   1140
cttttgatgg acagaacctc aaggagctgc gggaacgggt actgaggga aaataccgta   1200 ttccattcta catgtccacg gactgtgaaa acctgcttaa gaatttctc attcttaatc   1260 ccagcaagag aggcacttta gagcaaatca tgaaagatcg atggatgaat gtgggtcacg   1320
aagatgatga actaaagcct tacgtggagc cactccctga ctacaaggac ccccggcgga   1380
cagagctgat ggtgtccatg ggttatacac gggaagagat ccaggactcg ctggtgggcc   1440
agagatacaa cgaggtgatg gccacctatc tgctcctggg ctacaagagc tccgagctgg   1500
aaggcgacac catcaccctg aaaccccggc cttcagctga tctgaccaat agcagcgccc   1560
catccccatc ccacaaggta cagcgcagcg tgtcggccaa tcccaagcag cggcgcttca   1620
gcgaccaggc tggtcctgcc attcccacct ctaattctta ctctaagaag actcagagta   1680
acaacgcaga aaataagcgg cctgaggagg accgggagtc agggcggaaa gccagcagca   1740
cagccaaggt gcctgccagc cccctgcccg gtctggagag aagaagacc accccaaccc   1800 cctccacgga acagcgtcct ctccaccagc acaaatcgaa gcaggaattc cccactttg   1860 gagcgggcca gcctcggcca ggcctccatc cagaatggca aagacagcct aaccatgcca   1920
gggtcccggg cctccacggc ttctgcttct gcccgcagtct ctgcggcccg gccccgccag   1980
caccagaaat ccatgtcggc ctccgtgcac cccaacaagg cctctgggct gccccccacg   2040
gagagtaact gtgaggtgcc gcggcccagc acagccccc agcgtgtccc tgttgcctcc   2100
ccatccgccc acaacatcag cagcagtggt ggagccccag accgaactaa cttccccgg   2160 ggtgtgtcca gccgaagcac cttccatgct gggcagctcc gacaggtgcg ggaccagcag   2220
aatttgccct acggtgtgac cccagcctct ccctctggcc acagccaggg ccggcggggg   2280
gcctctggga gcatcttcag caagttcacc tccaagtttg tacgcagaaa tctgtctttc   2340
aggtttgcca gaaggaacct gaatgaacct gaaagcaaag accgagtgga gacgctcaga   2400
cctcacgtgg tgggcagtgg cggcaacgac aaagaaaagg aagaatttcg ggaggccaag   2460
```

```
cccegctccc tccgcttcac gtggagtatg aagaccacga gctccatgga gcccaacgag    2520
atgatgcggg agatccgcaa ggtgctggac gcgaacagct gccagagcga gctgcatgag    2580
aagtacatgc tgctgtgcat gcacggcacg ccgggccacg aggacttcgt gcagtgggag    2640
atggaggtgt gcaaactgcc gcggctctct ctcaacgggg ttcgatttaa gcggatatcg    2700
ggcacctcca tggccttcaa aaacattgcc tccaaaatag ccaacgagct gaagctttaa    2760
caggctgcca ggagcggggg cggcgggggg cgggccagct ggacgggctg ccggccgctg    2820
cgccgcccca cctgggcgag actgcagcga tggattggtg tgtctcccct gctggcactt    2880
ctcccctccc tggcccttct cagttttctc ttacatgttt gtgggggggtg ggagattgtt    2940 ntccagcacc ccacattcac ccctgcccag agattccccc ttctcctctc ccctactgga    3000
ggcaaaggaa ggggagggtg gatgggggg cagggctccc cctcggtact gcggttgcac    3060
agagtatttc gcctaaacca agaaattttt tattaccaaa aag                      3103

<210> SEQ ID NO 4
<211> LENGTH: 2086
<212> TYPE: DNA
<213> ORGANISM: Homo sapiens

<400> SEQUENCE: 4
agtccaacat gattcggggc cgcaactcag ccacctctgc tgatgagcag ccccacattg      60
gaaactaccg gctcctcaag accattggca agggtaattt tgccaaggtg aagttggccc     120
gacacatcct gactgggaaa gaggtagctg tgaagatcat tgacaagact caactgaact     180
cctccagcct ccagaaacta ttccgcgaag taagaataat gaaggttttg aatcatccca     240
acatagttaa attatttgaa gtgattgaga ctgagaaaac gctctacctt gtcatggagt     300
acgctagtgg cggagaggta tttgattacc tagtggctca tggcaggatg aaagaaaaag     360
aggctcgagc caaattccgc cagatagtgt ctgctgtgca gtactgtcac cagaagttta     420
ttgtccatag agacttaaag gcagaaaacc tgcttcttgga tgctgatatg aacatcaaga     480
ttgcagactt tggcttcagc aatgaattca cctttgggaa caagctggac accttctgtg     540
gcagtccccc ttatgctgcc ccagaactct tccagggcaa aaaatatgat ggacccgagg     600
tggatgtgtg gagcctagga gttatcctct atacactggt cagcggatcc ctgcctttg      660 atggacagaa cctcaaggag ctgcgggaac gggtactgag gggaaaatac cgtattccat     720
tctacatgtc cacggactgt gaaaacctgc ttaagaaatt tctcattctt aatcccagca     780
agagaggcac tttagagcaa atcatgaaag atcgatggat gaatgtgggt cacgaagatg     840
atgaactaaa gccttacgtg gagccactcc ctgactacaa ggaccccggg cggacagagc     900
tgatggtgtc catgggttat acacgggaag agatccagga ctcgctggtg ggccagagat     960
acaacgaggt gatggccacc tatctgctcc tgggctacaa gagctccgag ctggaaggcg    1020
acaccatcac cctgaaaccc cggccttcag ctgatctgac caatagcagc gccccatccc    1080
catcccacaa ggtacagcgc agcgtgtcgg ccaatcccaa gcagcggcgc ttcagcgacc    1140
aggctggtcc tgccattccc acctctaatt cttactctaa gaagactcag agtaacaacg    1200
cagaaaataa gcggcctgag gaggaccggg agtcagggcg gaaagccagc agcacagcca    1260
aggtgcctgc cagcccctg cccggtctgg agaggaagaa gaccacccca accccctcca    1320
cgaacagcgt cctctccacc agcacaaatc gaagcaggaa ttccccactt ttggagcggg    1380
ccagcctcgg ccaggcctcc atccagaatg gcaaagacag cacagccccc cagcgtgtcc    1440
ctgttgcctc cccatccgcc cacaacatca gcagcagtgg tggagcccca gaccgaactc    1500
```

| | |
|---|---|
| acttccccg gggtgtgtcc agccgaagca ccttccatgc tgggcagctc cgacaggtgc | 1560 |
| gggaccagca gaatttgccc tacggtgtga ccccagcctc tccctctggc cacagccagg | 1620 |
| gccggcgggg ggcctctggg agcatcttca gcaagttcac ctccaagttt gtacgcagga | 1680 |
| acctgaatga acctgaaagc aaagaccgag tggagacgct cagacctcac gtggtgggca | 1740 |
| gtggcggcaa cgacaaagaa aaggaagaat ttcgggaggc caagcccgc tccctccgct | 1800 |
| tcacgtggag tatgaagacc acgagctcca tggagcccaa cgagatgatg cgggagatcc | 1860 |
| gcaaggtgct ggacgcgaac agctgccaga gcgagctgca tgagaagtac atgctgctgt | 1920 |
| gcatgcacgg cacgccgggc cacgaggact cgtgcagtg ggagatggag gtgtgcaaac | 1980 |
| tgccgcggct ctctctcaac ggggttcgat ttaagcggat atcgggcacc tccatggcct | 2040 |
| tcaaaaacat tgcctccaaa atagccaacg agctgaagct ttaaca | 2086 |

<210> SEQ ID NO 5
<211> LENGTH: 2248
<212> TYPE: DNA
<213> ORGANISM: Homo sapiens

<400> SEQUENCE: 5

| | |
|---|---|
| agtccaacat gattcggggc cgcaactcag ccacctctgc tgatgagcag ccccacattg | 60 |
| gaaactaccg gctcctcaag accattggca agggtaattt tgccaaggtg aagttggccc | 120 |
| gacacatcct gactgggaaa gaggtagctg tgaagatcat tgacaagact caactgaact | 180 |
| cctccagcct ccagaaacta ttccgcgaag taagaataat gaaggttttg aatcatccca | 240 |
| acatagttaa attatttgaa gtgattgaga ctgagaaaac gctctacctt gtcatggagt | 300 |
| acgctagtgg cggagaggta tttgattacc tagtggctca tggcaggatg aaagaaaaag | 360 |
| aggctcgagc caaattccgc cagatagtgt ctgctgtgca gtactgtcac cagaagttta | 420 |
| ttgtccatag agacttaaag gcagaaaacc tgctcttgga tgctgatatg aacatcaaga | 480 |
| ttgcagactt tggcttcagc aatgaattca cctttgggaa caagctggac accttctgtg | 540 |
| gcagtccccc ttatgctgcc ccagaactct tccagggcaa aaaatatgat ggacccgagg | 600 |
| tggatgtgtg gagcctagga gttatcctct atacactggt cagcggatcc ctgccttttg | 660 |
| atggacagaa cctcaaggag ctgcgggaac gggtactgag gggaaaatac cgtattccat | 720 |
| tctacatgtc cacggactgt gaaaacctgc ttaagaaatt tctcattctt aatcccagca | 780 |
| agagaggcac tttagagcaa atcatgaaag atcgatggat gaatgtgggt cacgaagatg | 840 |
| atgaactaaa gccttacgtg gagccactcc ctgactacaa ggaccccgg cggacagagc | 900 |
| tgatggtgtc catgggttat acacgggaag atccagga ctcgctggtg gccagagat | 960 |
| acaacgaggt gatggccacc tatctgctcc tgggctacaa gagctccgag ctggaaggcg | 1020 |
| acaccatcac cctgaaaccc cggccttcag ctgatctgac caatagcagc gccccatccc | 1080 |
| catcccacaa ggtacagcgc agcgtgtcgg ccaatcccaa gcagcggcgc ttcagcgacc | 1140 |
| aggctggtcc tgccattccc acctctaatt cttactctaa gaagactcag agtaacaacg | 1200 |
| cagaaaataa gcggcctgag gaggaccggg agtcagggcg gaaagccagc agcacagcca | 1260 |
| aggtgcctgc cagcccctg cccggtctgg agaggaagaa gaccaccca accccctcca | 1320 |
| cgaacagcgt cctctccacc agcacaaatc gaagcaggaa ttccccactt ttggagcggg | 1380 |
| ccagcctcgg ccaggcctcc atccagaatg gcaaagacag cctaaccatg ccagggtccc | 1440 |
| gggcctccac ggcttctgct tctgccgcag tctctgcggc ccggccccgc cagcaccaga | 1500 |
| aatccatgtc ggcctccgtg cacccccaaca aggcctctgg gctgcccccc acggagagta | 1560 |

-continued
actgtgaggt gccgcggccc agcacagccc cccagcgtgt ccctgttgcc tccccatccg 1620
cccacaacat cagcagcagt ggtggagccc cagaccgaac taacttcccc cggggtgtgt 1680
ccagccgaag caccttccat gctgggcagc tccgacaggt gcgggaccag cagaatttgc 1740
cctacggtgt gaccccagcc tctccctctg gccacagcca gggccggcgg ggggcctctg 1800
ggagcatctt cagcaagttc acctccaagt ttgtacgcag gaacctgaat gaacctgaaa 1860
gcaaagaccg agtggagacg ctcagacctc acgtggtggg cagtggcggc aacgacaaag 1920
aaaaggaaga atttcgggag gccaagcccc gctccctccg cttcacgtgg agtatgaaga 1980
ccacgagctc catggagccc aacgagatga tgcgggagat ccgcaaggtg ctggacgcga 2040
acagctgcca gagcgagctg catgagaagt acatgctgct gtgcatgcac ggcacgccgg 2100
gccacgagga cttcgtgcag tgggagatgg aggtgtgcaa actgccgcgg ctctctctca 2160
acggggttcg atttaagcgg atatcgggca cctccatggc cttcaaaaac attgcctcca 2220
aaatagccaa cgagctgaag ctttaaca 2248

<210> SEQ ID NO 6
<211> LENGTH: 2701
<212> TYPE: DNA
<213> ORGANISM: Homo sapiens

<400> SEQUENCE: 6
ggcacgaggg ctgaacgaga gggacacgga gcagcccacc ttgggacacc ttgactccaa 60
gcccagcagt aagtccaaca tgattcgggg ccgcaactca gccacctctg ctgatgagca 120
gccccacatt ggaaactacc ggctcctcaa gaccattggc aagggtaatt ttgccaaggt 180
gaagttggcc cgacacatcc tgactgggaa agaggtagct gtgaagatca ttgacaagac 240
tcaactgaac tcctccagcc tccagaaact attccgcgaa gtaagaataa tgaaggtttt 300
gaatcatccc aacatagtta aattatttga agtgattgag actgagaaaa cgctctacct 360
tgtcatggag tacgctagtg gcggagaggt atttgattac ctagtggctc atggcaggat 420
gaaagaaaaa gaggctcgag ccaaattccg ccagatagtg tctgctgtgc agtactgtca 480
ccagaagttt attgtccata gagacttaaa ggcagaaaac ctgctcttgg atgctgatat 540
gaacatcaag attgcagact ttggcttcag caatgaattc acctttggga acaagctgga 600
caccttctgt ggcagtcccc cttatgctgc cccagaactc ttccagggca aaaaatatga 660
tggacccgag gtggatgtgt ggagcctagg agttatcctc tatacactgg tcagcggatc 720
cctgcctttt gatggacaga acctcaagga gctgcgggaa cgggtactga ggggaaaata 780
ccgtattcca ttctacatgt ccacggactg tgaaaacctg cttaagaaat ttctcattct 840
taatcccagc aagagaggca ctttagagca aatcatgaaa gatcgatgga tgaatgtggg 900
tcacgaagat gatgaactaa agccttacgt ggagccactc cctgactaca aggacccccg 960
gcggacagag ctgatggtgt ccatgggtta tacacgggaa gagatccagg actcgctggt 1020
gggccagaga tacaacgagg tgatggccac ctatctgctc ctgggctaca agagctccga 1080
gctggaaggc gacaccatca ccctgaaacc ccggccttca gctgatctga ccaatagcag 1140
cgccccatcc ccatcccaca aggtacagcg cagcgtgtcg gccaatccca agcagcggcg 1200
cttcagcgac caggcagctg gtcctgccat tcccacctct aattcttact ctaagaagac 1260
tcagagtaac aacgcagaaa ataagcggcc tgaggaggac cgggagtcag ggcggaaagc 1320
cagcagcaca gccaaggtgc ctgccagccc cctgcccggt ctggagagga agaagaccac 1380
cccaaccccc tccacgaaca gcgtcctctc caccagcaca aatcgaagca ggaattcccc 1440

```
acttttggag cgggccagcc tcggtcaggc ctccatccag aatggcaaag acagcctaac      1500
catgccaggg tcccgggcct ccacggcttc tgcttctgcc gcagtctctg cggcccggcc      1560
ccgccagcac cagaaatcca tgtcggcctc cgtgcacccc aacaaggcct ctgggctgcc      1620
ccccacggag agtaactgtg aggtgccgcg gcccagcaca gccccccagc gtgtccctgt      1680
tgcctcccca tccgcccaca acatcagcag cagtggtgga gccccagacc gaactaactt      1740
cccccggggt gtgtccagcc gaagcacctt ccatgctggg cagctccgac aggtgcggga      1800
ccagcagaat ttgccctacg gtgtgacccc agcctctccc tctggccaca gccagggccg      1860
gcgggggggcc tctgggagca tcttcagcaa gttcacctcc aagtttgtac gcagaaatct      1920
gtctttcagg tttgccagaa ggaacctgaa tgaacctgaa agcaaagacc gagtggagac      1980
gctcagacct cacgtggtgg gcagtggcgg caacgacaaa gaaaaggaag aatttcggga      2040
ggccaagccc cgctccctcc gcttcacgtg gagtatgaag accacgagct ccatggagcc      2100
caacgagatg atgcgggaga tccgcaaggt gctggacgcg aacagctgcc agagcgagct      2160
gcatgagaag tacatgctgc tgtgcatgca cggcacgccg ggccacgagg acttcgtgca      2220
gtgggagatg gaggtgtgca aactgccgcg gctctctctc aacggggttc gatttaagcg      2280
gatatcgggc acctccatgg ccttcaaaaa cattgcctcc aaaatagcca acgagctgaa      2340
gctttaacag gctgccagga gcgggggcgg cggggcggg ccagctggac gggctgccgg      2400
ccgctgcgcc gccccacctg ggcgagactg cagcgatgga ttggtgtgtc tcccctgctg      2460
gcacttctcc cctccctggc ccttctcagt tttctcttac atgtttgtgg ggggtgggag      2520
attgttctcc agccccccac attcaccccct gcccagagat tccccttct cctctcccct      2580
actggaggca aaggaagggg agggtggatg ggggggcagg gctcccccctc ggtactgcgg      2640
ttgcacagag tatttcgcct aaaccaagaa atttttttatt accaaaaaaa aaaaaaaaa      2700
a                                                                     2701

<210> SEQ ID NO 7
<211> LENGTH: 2112
<212> TYPE: DNA
<213> ORGANISM: Homo sapiens

<400> SEQUENCE: 7
cccagcagta agtccaacat gattcggggc cgcaactcag ccacctctgc tgatgagcag        60
ccccacattg gaaactaccg gctcctcaag accattggca agggtaattt tgccaaggtg       120
aagttggccc gacacatcct gactgggaaa gaggtagctg tgaagatcat tgacaagact       180
caactgaact cctccagcct ccagaaacta ttccgcgaag taagaataat gaaggttttg       240
aatcatccca acatagttaa attatttgaa gtgattgaga ctgagaaaac gctctacctt       300
gtcatggagt acgctagtgg cggagaggta tttgattacc tagtggctca tggcaggatg       360
aaagaaaaag aggctcgagc caaattccgc cagatagtgt ctgctgtgca gtactgtcac       420
cagaagttta ttgtccatag agacttaaag gcagaaaacc tgcttcttgga tgctgatatg       480
aacatcaaga ttgcagactt tggcttcagc aatgaattca cctttgggaa caagctggac       540
accttctgtg gcagtccccc ttatgctgcc ccagaactct tccagggcaa aaaatatgat       600
ggacccgagg tggatgtgtg gagcctagga gttatcctct atactggt cagcggatcc         660
ctgcctttgg atggacagaa cctcaaggag ctgcgggaac gggtactgag gggaaaatac       720
cgtattccat tctacatgtc cacggactgt gaaaacctgc ttaagaaatt tctcattctt       780
aatcccagca agagaggcac tttagagcaa atcatgaaag atcgatggat gaatgtgggt       840
```

```
cacgaagatg atgaactaaa gccttacgtg gagccactcc ctgactacaa ggaccccggg      900
cggacagagc tgatggtgtc catgggttat acacgggaag agatccagga ctcgctggtg      960
ggccagagat acaacgaggt gatggccacc tatctgctcc tgggctacaa gagctccgag     1020
ctggaaggcg acaccatcac cctgaaaccc cggccttcag ctgatctgac caatagcagc     1080
gccccatccc catcccacaa ggtacagcgc agcgtgtcgg ccaatcccaa gcagcggcgc     1140
ttcagcgacc aggctggtcc tgccattccc acctctaatt cttactctaa gaagactcag     1200
agtaacaacg cagaaaataa gcggcctgag gaggaccggg agtcagggcg gaaagccagc     1260
agcacagcca aggtgcctgc cagcccctg cccggtctgg agaggaagaa gaccacccca     1320
accccctcca cgaacagcgt cctctccacc agcacaaatc gaagcaggaa ttccccactt     1380
ttggagcggg ccagcctcgg ccaggcctcc atccagaatg gcaaagacag cacagccccc     1440
cagcgtgtcc ctgttgcctc ccatccgcc cacaacatca gcagcagtgg tggagcccca     1500
gaccgaacta acttccccg gggtgtgtcc agccgaagca ccttccatgc tgggcagctc     1560
cgacaggtgc gggaccagca gaatttgccc tacggtgtga ccccagcctc tccctctggc     1620
cacagccagg gccggcgggg ggcctctggg agcatcttca gcaagttcac ctccaagttt     1680
gtacgcagga acctgaatga acctgaaagc aaagaccgag tggagacgct cagacctcac     1740
gtggtgggca gtgcggcaa cgacaaagaa aggaagaat tcgggaggc caagcccgc        1800 tccctccgct tcacgtggag tatgaagacc acgagctcca tggagcccaa cgagatgatg     1860
cgggagatcc gcaaggtgct ggacgcgaac agctgccaga gcgagctgca tgagaagtac     1920
atgctgctgt gcatgcacgg cacgccgggc cacgaggact tcgtgcagtg ggagatggag     1980
gtgtgcaaac tgccgcggct ctctctcaac gggggttcgat ttaagcggat atcgggcacc     2040
tccatggcct tcaaaaacat tgcctccaaa atagccaacg agctgaagct ttaacaggct     2100
gccaggagcg gg                                                          2112
```

<210> SEQ ID NO 8
<211> LENGTH: 2965
<212> TYPE: DNA
<213> ORGANISM: Homo sapiens

<400> SEQUENCE: 8

```
cgggcaaccg cctcgcccga agccctccct cgttactgtc cgcatacccc ggcggcgccg       60
ccgcggaaag cggctccccc tcctcttact ccgcgtcctc ttcccctctt ccccgccgg       120 ggcacgcttg ttgcaccgtc ccgcggcctg cgggagccgc tcgccccgga cttgagctcg      180
cgtacgaccc atttcctgtc gccccccgga gcccgcacca cagcccggcc ggtctagacc      240
ccggcagacc ccgctggccg cacaaaatgt cggcccggac gccattgccg acggtgaacg      300
agcgggacac ggtaaatcat acgactgtgg atggatatac tgaaccacac atccagccta      360
ccaagtcgag tagcagacag aacatccccc ggtgtagaaa ctccattacg tcagcaacag      420
atgaacagcc tcacattgga aattaccgtt tacaaaaaac aatagggaag ggaaattttg      480
ccaaagtcaa attggcaaga cacgttctaa ctggtagaga ggttgctgtg aaaataatag      540
acaaaactca gctaaatcct accagtctac aaaagttatt tcgagaagta cgaataatga      600
agatactgaa tcatcctaat atagtaaaat tgtttgaagt tattgaaaca gagaagactc      660
tctatttagt catggaatac gcgagtgggg gtgaagtatt tgattactta gttgcccatg      720
gaagaatgaa agagaaagag gcccgtgcaa aatttaggca gattgtatct gctgtacagt      780
attgtcatca aaagtacatt gttcaccgtg atcttaaggc tgaaaacctt ctccttgatg      840
```

```
gtgatatgaa tattaaaatt gctgactttg gttttagtaa tgaatttaca gttgggaaca    900
aattggacac attttgtgga agcccaccct atgctgctcc cgagcttttc caaggaaaga    960
agtatgatgg gcctgaagtg gatgtgtgga gtctgggcgt cattctctat acattagtca   1020
gtggctcctt gcctttcgat ggccagaatt taaaggaact gcgagagcga gttttacgag   1080
ggaagtaccg tattcccttc tatatgtcca cagactgtga aaatcttctg aagaaattat   1140
tagtcctgaa tccaataaag agaggcagct tggaacaaat aatgaaagat cgatggatga   1200
atgttggtca tgaagaggaa gaactaaagc catatactga gcctgatccg gatttcaatg   1260
acacaaaaag aatagacatt atggtcacca tgggctttgc acgagatgaa ataaatgatg   1320
ccttaataaa tcagaagtat gatgaagtta tggctactta tattcttcta ggtagaaaac   1380
cacctgaatt tgaaggtggt gaatcgttat ccagtggaaa cttgtgtcag aggtcccggc   1440
ccagtagtga cttaaacaac agcactcttc agtccctgc tcacctgaag gtccagagaa    1500
gtatctcagc aaatcagaag cagcggcgtt tcagtgatca tgctggtcca tccattcctc   1560
ctgctgtatc atataccaaa agacctcagg ctaacagtgt ggaaagtgaa cagaaagagg   1620
agtgggacaa agatgtggct cgaaaacttg gcagcacaac agttggatca aaaagcgaga   1680
tgactgcaag ccctcttgta gggccagaga ggaaaaaatc ttcaactatt ccaagtaaca   1740
atgtgtattc tggaggtagc atggcaagaa ggaatacata tgtctgtgaa aggaccacag   1800
atcgatacgt agcattgcag aatggaaaag acagcagcct tacggagatg tctgtgagta   1860
gcatatcttc tgcaggctct tctgtggcct ctgctgtccc ctcagcacga ccccgccacc   1920
agaagtccat gtccacttct ggtcatccta ttaaagtcac actgccaacc attaaagacg   1980
gctctgaagc ttaccggcct ggtacaaccc agagagtgcc tgctgcttcc ccatctgctc   2040
acagtattag tactgcgact ccagaccgga cccgttttcc ccgagggagc tcaagccgaa   2100
gcactttcca tggtgaacag ctccgggagc gacgcagcgt tgcttataat gggccacctg   2160
cttcaccatc ccatgaaacg ggtgcatttg cacatgccag aaggggaacg tcaactggta   2220
taataagcaa aatcacatcc aaatttgttc gcagggatcc aagtgaaggc gaagccagtg   2280
gcagaaccga cacctcaaga agtacatcag gggaaccaaa agaaagagac aaggaagagg   2340
gtaaagattc taagccgcgt tctttgcggt tcacatggag tatgaagacc actagttcaa   2400
tggaccctaa tgacatgatg agagaaatcc gaaaagtgtt agatgcaaat aactgtgatt   2460
atgagcaaaa agagagattt ttgcttttct gtgtccatgg agacgctaga caggatagcc   2520
tcgtgcagtg ggagatggaa gtctgcaagt tgccacgact gtcacttaat ggggttcgct   2580
tcaagcgaat atctgggaca tctattgcct ttaagaacat tgcatcaaaa atagcaaatg   2640
agcttaagct gtaaagaagt ccaaatttac aggttcaggg aagatacata catatatgag   2700
gtacagtttt tgaatgtact ggtaatgcct aatgtggtct gcctgtgaat ctccccatgt   2760
agaatttgcc cttaatgcaa taaggttata catagttatg aactgtaaaa ttaaagtcag   2820
tatgaactat aataaatatc tgtagcttaa aaagtaggtt cacatgtaca ggtaagtata   2880
ttgtgtattt ctgttcattt tctgttcata gagttgtata ataaaacatg attgcttaaa   2940
aacttgaaaa aaaaaaaaaa aaaaa                                          2965
```

<210> SEQ ID NO 9
<211> LENGTH: 3210
<212> TYPE: DNA
<213> ORGANISM: Homo sapiens

<400> SEQUENCE: 9

```
ggcgcggcgg cggcggtggc tgtgaccgcg cggaccgagc cgagacattc gcgccggggg     60
atcgggcgcc gccgccgctg ggccccgggc gcgtggatgc ggctgggtcg ggcggcgccg    120
tacacctgag gcgagaacg gggcgcggcg cgggtgacgc tgtcagggcc gcggttcctg    180
acgcccaggc gctcgccagg acgagccagg cagtgatttg aggcaccggc ttcaccttca    240
cccatggtcc ggagagccta gcggggctcg ccaccgcctc ccggctcccc ttccacgcct    300
catcctgcca gcctcgccgc cccgccagcg ccgggcaacc gcctcgcccg aagccctccc    360
tcgttactgt ccgcataccc cggcggcgcc gccgcgggaa gcggctcccc ctcctcttcc    420
tccgcgtcct cttccctctt tcccccgccg gggccgcttg ttgcaccgcc ccgcggcctg    480
cgggagccgc tcgccccggc cttgtgctcg cgtccgcacc cctttcctgt cgccccccgg    540
ggcccgcacc acagcccggc cggcgagacc ccggccagac cccgctgccc gcacaaaatg    600
tcggcccgga cgccattgcc gacggtgaac gagcgggaca cggaaaatca tacatctgtg    660
gatggatata ctgaaccaca catccagcct accaagtcga gtagcagaca gaacatcccc    720
cggtgtagaa actccattac gtcagcaaca gatgaacagc ctcacattgg aaattaccgt    780
ttacaaaaaa caatagggaa gggaaatttt gccaaagtca aattggcaag acacgttcta    840
actggtagag aggttgctgt gaaaataata gacaaaactc agctaaatcc taccagtcta    900
caaaagttat ttcgagaagt acgaataatg aagatactga atcatcctaa tataggtgaa    960
gtatttgatt acttagttgc ccatggaaga atgaaagaga agaggcccg tgcaaaattt   1020 aggcagattg tatctgctgt acagtattgt catcaaaagt acattgttca ccgtgatctt   1080
aagctgaaaa ccttctcctt gatggtgata tgaatattaa aattgctgac tttggtttta   1140
gtaatgaatt tacagttggg aacaaattgg acacattttg tggaagccca ccctatgctg   1200 ctccccgagct tttccaagga agaagtatg atgggcctga agtggatgtg tggagtctgg   1260
gcgtcattct ctatacatta gtcagtggct ccttgccttt cgatggccag aatttaaagg   1320
aactgcgaga gcgagtttta cgagggaagt accgtattcc cttctatatg tccacagact   1380
gtgaaaatct tctgaagaaa ttattagtcc tgaatccaat aaagagaggc agcttggaac   1440
aaataatgaa agatcgatgg atgaatgttg gtcatgaaga ggaagaacta aagccatata   1500
ctgagcctga tccggatttc aatgacacaa aaagaataga cattatggtc accatgggct   1560
ttgcacgaga tgaaataaat gatgccttaa taaatcagaa gtatgatgaa gttatggcta   1620
cttatattct tctaggtaga aaaccacctg aatttgaagg tggtgaatcg ttatccagtg   1680
gaaacttgtg tcagaggtcc cggcccagta gtgacttaaa caacagcact cttcagtccc   1740
ctgctcacct gaaggtccag agaagtatct cagcaaatca gaagcagcgg cgtttcagtg   1800
atcatgctgg tccatccatt cctcctgctg tatcatatac caaaagacct caggctaaca   1860
gtgtggaaag tgaacagaaa gaggagtggg acaaagatgt ggctcgaaaa cttggcagca    1920
caacagttgg atcaaaaagc gagatgactg caagccctct tgtagggcca gagaggaaaa   1980
aatcttcaac tattccaagt aacaatgtgt attctggagg tagcatggca agaaggaata   2040
catatgtctg tgaaaggacc acagatcgat acgtagcatt gcagaatgga aaagacagca   2100
gccttacgga gatgtctgtg agtagcatat cttctgcagg ctcttctgtg gcctctgctg   2160 tccccctcagc acgaccccgc caccagaagt ccatgtccac ttctggtcat cctattaaag   2220
tcacactgcc aaccattaaa gacggctctg aagcttaccg gcctggtaca acccagagag   2280
tgcctgctgc ttccccatct gctcacagta ttagtactgc gactccagac cggacccgtt   2340
ttccccgagg gagctcaagc cgaagcactt tccatggtga acagctccgg gagcgacgca   2400
```

```
gcgttgctta taatgggcca cctgcttcac catcccatga aacgggtgca tttgcacatg    2460
ccagaagggg aacgtcaact ggtataataa gcaaaatcac atccaaattt gttcgcaggg    2520
atccaagtga aggcgaagcc agtggcagaa ccgacacctc aagaagtaca tcaggggaac    2580
caaaagaaag agacaaggaa gagggtaaag attctaagcc gcgttctttg cggttcacat    2640
ggagtatgaa gaccactagt tcaatggacc ctaatgacat gatgagagaa atccgaaaag    2700
tgttagatgc aaataactgt gattatgagc aaaaagagag attttttgctt ttctgtgtcc    2760 atggagacgc tagacaggat agcctcgtgc agtgggagag ggaagtctgc aagttgccac    2820
gactgtcact taatggggtt cgcttcaagc gaatatctgg gacatctatt gcctttaaga    2880
acattgcatc aaaaatagca aatgagctta agctgtaaag aagtccaaat ttacaggttc    2940
agggaagata catacatata tgaggtacag ttttgaatg tactggtaat gcctaatgtg    3000
gtctgcctgt gaatctcccc atgtagaatt tgcccttaat gcaataaggt tatacatagt    3060
tatgaactgt aaaattaaag tcagtatgaa ctataataaa tatctgtagc ttaaaaagta    3120
ggttcacatg tacaggtaag tatattgtgt atttctgttc attttctgtt catagagttg    3180
tataataaaa catgattgct taaaaacttg                                     3210

<210> SEQ ID NO 10
<211> LENGTH: 2505
<212> TYPE: DNA
<213> ORGANISM: Homo sapiens

<400> SEQUENCE: 10
gctggccgca caaatgtcg gcccggacgc cattgccgac ggtgaacgag cgggacacgg      60
aaaatcatac atctgtggat ggatatactg aaccacacat ccagcctacc aagtcgagta    120
gcagacagaa catcccccgg tgtagaaact ccattacgtc agcaacagat gaacagcctc    180
acattggaaa ttaccgttta caaaaaacaa tagggaaggg aaattttgcc aaagtcaaat    240
tggcaagaca cgttctaact ggtagagagg ttgctgtgaa aataatagac aaaactcagc    300
taaatcctac cagtctacaa aagttatttc gagaagtacg aataatgaag atactgaatc    360
atcctaatat agtaaaattg tttgaagtta ttgaaacaga gaagactctc tatttagtca    420
tggaatacgc gagtgggggt gaagtatttg attacttagt tgcccatgga agaatgaaag    480
agaaagaggc ccgtgcaaaa tttaggcaga ttgtatctgc tgtacagtat tgtcatcaaa    540
agtacattgt tcaccgtgat cttaaggctg aaaaccttct ccttgatggt gatatgaata    600
ttaaaattgc tgactttggt tttagtaatg aatttacagt tgggaacaaa ttggacacat    660
tttgtggaag cccaccctat gctgctcccg agcttttcca aggaaagaag tatgatgggc    720
ctgaagtgga tgtgtggagt ctgggcgtca ttctctatac attagtcagt ggctccttgc    780
ctttcgatgg ccagaattta aaggaactgc gagagcgagt tttacgaggg aagtaccgta    840
ttcccttcta tatgtccaca gactgtgaaa atcttctgaa gaattatta gtcctgaatc    900 caataaagag aggcagcttg gaacaaataa tgaaagatcg atggatgaat gttggtcatg    960
aagaggaaga actaaagcca tatactgagc ctgatccgga tttcaatgac acaaaaagaa   1020
tagacattat ggtcaccatg ggctttgcac gagatgaaat aaatgatgcc ttaataaatc   1080
agaagtatga tgaagttatg gctacttata ttcttcagg tagaaaacca cctgaatttg   1140
aaggtggtga atcgttatcc agtggaaact tgtgtcagag gtcccggccc agtagtgact   1200
taaacaacag cactcttcag tcccctgctc acctgaaggt ccagagaagt atctcagcaa   1260
atcagaagca gcggcgtttc agtgatcatg ctggtccatc cattcctcct gctgtatcat   1320
```

```
ataccaaaag acctcaggct aacagtgtgg aaagtgaaca gaaagaggag tgggacaaag    1380
atgtggctcg aaaacttggc agcacaacag ttggatcaaa aagcgagatg actgcaagcc    1440
ctcttgtagg gccagagagg aaaaaatctt caactattcc aagtaacaat gtgtattctg    1500
gaggtagcat ggcaagaagg aatacatatg tctgtgaaag gaccacagat cgatacgtag    1560
cattgcagaa tggaaaagac agcagcctta cggagatgtc tgtgagtagc atatcttctg    1620
caggctcttc tgtggcctct gctgtcccct cagcacgacc ccgccaccag aagtccatgt    1680
ccacttctgg tcatcctatt aaagtcacac tgccaaccat taaagacggc tctgaagctt    1740
accggcctgg tacaacccag agagtgcctg ctgcttcccc atctgctcac agtattagta    1800
ctgcgactcc agaccggacc cgttttcccc gagggagctc aagccgaagc actttccatg    1860
gtgaacagct ccgggagcga cgcagcgttg cttataatgg gccacctgct tcaccatccc    1920
atgaaacggg tgcatttgca catgccagaa ggggaacgtc aactggtata ataagcaaaa    1980
tcacatccaa atttgttcgc agggatccaa gtgaaggcga agccagtggc agaaccgaca    2040
cctcaagaag tacatcaggg gaaccaaaag aaagagacaa ggaagagggt aaagattcta    2100
agccgcgttc tttgcggttc acatggagta tgaagaccac tagttcaatg gaccctaatg    2160
acatgatgag agaaatccga aaagtgttag atgcaaataa ctgtgattat gagcaaaaag    2220
agagattttt gcttttctgt gtccatggag acgctagaca ggatagcctc gtgcagtggg    2280
agatggaagt ctgcaagttg ccacgactgt cacttaatgg ggttcgcttc aagcgaatat    2340
ctgggacatc tattgccttt aagaacattg catcaaaaat agcaaatgag cttaagctgt    2400
aaagaagtcc aaatttacag gttcagggaa gatacataca tatatgaggt acagttttg    2460 aatgtactgg taatgcctaa tgtggtctgc ctgtgaatct ccccca              2505

<210> SEQ ID NO 11
<211> LENGTH: 4638
<212> TYPE: DNA
<213> ORGANISM: Homo sapiens

<400> SEQUENCE: 11
ggcgcggcgg cggcggtggc tgtgaccgcg cggaccgagc cgagacattc gcgccggggg      60
atcgggcgcc gccgccgctg ggccccgggc gcgtggatgc ggctgggtcg ggcggcgccg     120
tacacctgag gcggagaacg gggcgcggcg cgggtgacgc tgtcagggcc gcggttcctg     180
acgcccaggc gctcgccagg acgagccagg cagtgatttg aggcaccggc ttcaccttca     240
cccatggtcc ggagagccta gcggggctcg ccaccgcctc ccggctcccc ttccacgcct     300
catcctgcca gcctcgccgc cccgccagcc ccgggcaacc gcctcgcccg aagccctccc     360
tcgttactgt ccgcataccc cggcggcgcc gccgcgggaa gcggctcccc ctcctcttcc     420
tccgcgtcct cttccctctt tccccgcgcg gggccgcttg ttgcaccgcc ccgcggcctg     480
cgggagccgc tcgccccggc cttgtgctcg cgtccgcacc cctttcctgt cgcccccgg     540 ggcccgcacc acagcccggc cggcgagacc ccggccagac cccgctgccc gcacaaaatg     600
tcggcccgga cgccattgcc gacggtgaac gagcgggaca cggaaaatca tacatctgtg     660
gatggatata ctgaaccaca catccagcct accaagtcga gtagcagaca gaacatcccc     720
cggtgtagaa actccattac gtcagcaaca gatgaacagc ctcacattgg aaattaccgt     780
ttacaaaaaa caatagggaa gggaaatttt gccaaagtca aattggcaag acacgttcta     840
actggtagag aggttgctgt gaaaataata gacaaaactc agctaaatcc taccagtcta     900
caaaagttat ttcgagaagt acgaataatg aagatactga atcatcctaa tataggtgaa     960
```

```
gtatttgatt acttagttgc ccatggaaga atgaaagaga aagaggcccg tgcaaaattt   1020
aggcagattg tatctgctgt acagtattgt catcaaaagt acattgttca ccgtgatctt   1080
aaggctgaaa accttctcct tgatggtgat atgaatatta aaattgctga ctttggtttt   1140
agtaatgaat ttacagttgg gaacaaattg gacacatttt gtggaagccc accctatgct   1200
gctcccgagc ttttccaagg aaagaagtat gatgggcctg aagtggatgt gtggagtctg   1260
ggcgtcattc tctatacatt agtcagtggc tccttgcctt tcgatggcca gaatttaaag   1320
gaactgcgag agcgagtttt acgagggaag taccgtattc ccttctatat gtccacagac   1380
tgtgaaaatc ttctgaagaa attattagtc ctgaatccaa taagagagg cagcttggaa    1440 caaataatga agatcgatg gatgaatgtt ggtcatgaag aggaagaact aaagccatat   1500
actgagcctg atccggattt caatgacaca aaaagaatag acattatggt caccatgggc   1560
tttgcacgag atgaaataaa tgatgcctta ataaatcaga gtatgatga agttatggct   1620 acttatattc ttctaggtag aaaaccacct gaatttgaag tggtgaatc gttatccagt    1680 ggaaacttgt gtcagaggtc ccggcccagt agtgacttaa caacagcac tcttcagtcc    1740 cctgctcacc tgaaggtcca gagaagtatc tcagcaaatc agaagcagcg gcgtttcagt   1800
gatcatgctg gtccatccat tcctcctgct gtatcatata ccaaaagacc tcaggctaac   1860
agtgtggaaa gtgaacagaa agaggagtgg gacaaagatg tggctcgaaa acttggcagc   1920
acaacagttg gatcaaaaag cgagatgact gcaagccctc ttgtagggcc agagaggaaa   1980
aaatcttcaa ctattccaag taacaatgtg tattctggag gtagcatggc aagaaggaat   2040
acatatgtct gtgaaaggac cacagatcga tacgtagcat tgcagaatgg aaaagacagc   2100
agccttacgg agatgtctgt gagtagcata tcttctgcag gctcttctgt ggcctctgct   2160
gtcccctcag cacgaccccg ccaccagaag tccatgtcca cttctggtca tcctattaaa   2220
gtcacactgc caaccattaa agacggctct gaagcttacc ggcctggtac aacccagaga   2280
gtgcctgctg cttccccatc tgctcacagt attagtactg cgactccaga ccggacccgt   2340
tttccccgag ggagctcaag ccgaagcact ttccatggtg aacagctccg ggagcgacgc   2400
agcgttgctt ataatgggcc acctgcttca ccatcccatg aaacgggtgc atttgcacat   2460
gccagaaggg gaacgtcaac tggtataata agcaaaatca catccaaatt tgttcgcaga   2520
agtacatcag gggaaccaaa agaaagagac aaggaagagg gtaaagattc taagccgcgt   2580
tctttgcggt tcacatggag tatgaagacc actagttcaa tggaccctaa tgacatgatg   2640
agagaaatcc gaaaagtgtt agatgcaaat aactgtgatt atgagcaaaa agagagattt   2700
ttgcttttct gtgtccatgg agacgctaga caggatagcc tcgtgcagtg ggagatggaa   2760
gtctgcaagt tgcacgact gtcacttaat ggggttcgct tcaagcgaat atctgggaca   2820
tctattgcct ttaagaacat tgcatcaaaa atagcaaatg agcttatgct gtaaagaagt   2880
ccaaatttac aggttcaggg aagatacata catatatgag gtacagtttt tgaatgtact   2940
ggtaatgcct aatgtggtct gcctgtgaat ctccccatgt agaatttgcc cttaatgcaa   3000
taaggttata catagttatg aactgtaaaa ttaaagtcag tatgaactat aataaatatc   3060
tgtagcttaa aaagtaggtt cacatgtaca ggtaagtata ttgtgtattt ctgttcattt   3120
tctgttcata gagttgtata ataaaacatg attgcttaaa aacttgtata gttgtctaga   3180
tttctgcacc tgaatgtatg tttgatgctt tgatttgaaa atgttcttcc ctgttatta   3240 cattctggtg ggttttaaa attcttacct ccatcatgca attttgaaaa ttgtgtccag   3300
aattaaaagt gcatagaaat agcctttaca attgtagcat ggacctttaa aaattgtttt   3360
```

```
aaaatcttat ttaaatttaa accagaagct gaaaaataga tcagctttat tatacacaaa      3420
attattactg cttatctttg ctcttttcct tgttatcccg caaggtttag ttgagaagat      3480
acaaaatgtt tacagtgttg gcacttagag tttttaaatt caagtacatg aaattcagta      3540
atagcattgc cttgagctaa ctaggaagta ccgggaaaaa agttaaatct acatcaagtt      3600
tcttttgaac tttgaagtgt tttctgaccc actgctaact gtagcaacaa aatttaaaag      3660
aaaaaaaaca tactttatct ggctattata acataaactg tcacgtaggt ttgctgcctt      3720
cagaataccg caatttaatt gcgggaatat aataatattg ggactgtttc acagcacaaa      3780
ctcatcttta cagtgttgat caatgcatca gttaagaaat aatgccacct caggaattaa      3840
ctggcattgg gaacatttgc ctcattctcc tgctatcctc ttcattcacc cctgccactg      3900
taatatctat aagtacttaa gagacttgtg agcaaaacat actatttata acagtatatg      3960
attgatttat gcttatgtgg ttgttcagtt tgttcccatg taactcgttt gttttaaata      4020
ttttgccaga tttcttgtat ttattccaca tcattatgcc tataatgtgc cgctttgtga      4080
ttgggcattt gcctactttt ctttcataat tagtgatata tgcgatgtaa aaccactagt      4140
aaaggtacat tttaatactt gttatttat actgaattag ccttggaggt tgactgtgca      4200
atgttattta ctgttgtaat tactgtaata ccaacatatg ggccccatct gcacactcct      4260
gaaaaacaga aagtgtattc aaattttatc agtttaaaga aaataaagct gtgataaata      4320
ctgtaattcc aacctacatt agaaggtcta agtgtaggtg atgtgccatt ccataatggc      4380
ttccagacta gggtgaattt tatgttctgt actgtactgt gatgtagctt tcttctgtaa      4440
cagttatgtt ttaaaattaa gtgagttttt ttttgccctt agcaaagggt ggtgtttgaa      4500
aaaaaaaatg tgtagcccct ttttaaccta gtgttcattc aaaaaaaaat tgatgcaaat      4560
ctttattcac tttcactggt gcacactgaa attttacttg aacagttctc ataataaagc      4620
acttgtcttt tgctctttt                                                  4638

<210> SEQ ID NO 12
<211> LENGTH: 2720
<212> TYPE: DNA
<213> ORGANISM: Homo sapiens

<400> SEQUENCE: 12
tcatggaata cgcgagtggg ggtgaagtat ttgattactt agttgcccat ggaagaatga       60
aagagaaaga ggcccgtgca aaatttaggc agattgtatc tgctgtacag tattgtcatc      120
aaaagtacat tgttcaccgt gatcttaagg ctgaaaacct tctccttgat ggtgatatga      180
atattaaaat tgctgacttt ggttttagta atgaatttac agttgggaac aaattggaca      240
cattttgtgg aagcccaccc tatgctgctc ccgagctttt ccaaggaaag aagtatgatg      300
gtcctgaagt ggatgtgtgg agtctgggcg tcattctcta tacattagtc agtggctcct      360
tgcctttcga tggccagaat ttaaaggaac tgcgagagcg agttttacga gggaagtacc      420
gtattccctt ctatatgtcc acagactgtg aaaatcttct gaagaaatta ttagtcctga      480
atccaataaa gagaggcagc ttggaacaaa taatgaaaga tcgatggatg aatgttggtc      540
atgaagagga agaactaaag ccatatactg agcctgatcc ggatttcaat gacacaaaaa      600
gaatagacat tatggtcacc atgggctttg cacgagatga aataaatgat gccttaataa      660
atcagaagta tgatgaagtt atggctactt atattcttct aggtagaaaa ccacctgaat      720
ttgaaggtgt tgaatcgtta tccagtggaa acttgtgtca gaggtcccgg cccagtagtg      780
acttaaacaa cagcactctt cagtcccctg ctcacctgaa ggtccagaga agtatctcag      840
```

| | |
|---|---|
| caaatcagaa gcagcggcgt ttcagtgatc atgctggtcc atccattcct cctgctgtat | 900 |
| catataccaa agacctcag gctaacagtg tggaaagtga acagaaagag gagtgggaca | 960 |
| aagatgtggc tcgaaaactt ggcagcacaa cagttggatc aaaaagcgag atgactgcaa | 1020 |
| gccctcttgt agggccagag aggaaaaaat cttcaactat tccaagtaac aatgtgtatt | 1080 |
| ctggaggtag catggcaaga aggaatacat atgtctgtga aggaccaca gatcgatacg | 1140 |
| tagcattgca gaatggaaaa aacagcagcc ttacggagat gtctgtgagt agcatatctt | 1200 |
| ctgcaggctc ttctgtggcc tctgctgccc cctcagcacg accccgccac cagaagtcca | 1260 |
| tgtccacttc tggtcatcct attaaagtca cactgccaac cattaaagac ggctctgaag | 1320 |
| cttaccggcc tggtacaacc cagagagtgc ctgctgcttc cccatctgct cacagtatta | 1380 |
| gtactgcgac tccagaccgg acccgttttc cccgaggag ctcaagccga agcactttcc | 1440 |
| atggtgaaca gctccgggag cgacgcagcg ttgcttataa tgggccacct gcttcaccat | 1500 |
| cccatgaaac gggtgcattt gcacatgcca gaagggaac gtcaactggt ataataagca | 1560 |
| aaatcacatc caaatttgtt cgcagaagta catcagggga accaaaagaa agagacaagg | 1620 |
| aagagggtaa agattctaag ccgcgttctt tgcggttcac atggagtatg aagaccacta | 1680 |
| gttcaatgga ccctaatgac atgatgagag aaatccgaaa agtgttagat gcaaataact | 1740 |
| gtgattatga gcaaaagag agattttttgc ttttctgtgt ccatgagac gctagacagg | 1800 |
| atagcctcgt gcagtgggag atggaagtct gcaagttgca cgactgtcac ttaatggggt | 1860 |
| tcgcttcaag cgaatatctg ggacatctat tgccttaag aacattgcat caaaaatagc | 1920 |
| aaatgagctt aagctgtaaa gaagtccaaa tttacaggtt cagggaagat acatacatat | 1980 |
| atgaggtaca gttttgaat gtactggtaa tgcctaatgt ggtctgcctg tgaatctccc | 2040 |
| catgtagaat ttgcccttaa tgcaataagg ttatacatag ttatgaactg taaaattaaa | 2100 |
| gtcagtatga actataataa atatctgtag cttaaaaagt aggttcacat gtacaggtaa | 2160 |
| gtatattgtg tatttctgtt catttctgt tcatagagtt gtataataaa acatgattgc | 2220 |
| ttaaaaactt gtatagttgt ctagatttct gcacctgaat gtatgtttga tgctttgatt | 2280 |
| tgaaaatgtt cttccctgtt atttacattc cggtgggttt ttaaaattct tacctccatc | 2340 |
| atgcaatttt gaaaattgtg tccagaatta aaagtgcata gaaatagcct ttacaattgt | 2400 |
| agcatggacc tttaaaaatt gttttaaaat cttatttaaa tttaaaccag aagctgaaaa | 2460 |
| atagatcagc tttattatac acaaaattat tactgcttat ctttgctctt ttccttgtta | 2520 |
| tcccgcaagg tttagttgag aagatacaaa atgtttacag tgttggcact tagagttttt | 2580 |
| aaattcaagt acatgaaatt cagtaatagc attgccttga gctaactagg aagtaccggg | 2640 |
| aaaaagtta atctacatc aagtttcttt tgaactttga agtgttttct gacccactgc | 2700 |
| taactgtagc aacaaaattt | 2720 |

<210> SEQ ID NO 13
<211> LENGTH: 2698
<212> TYPE: DNA
<213> ORGANISM: Homo sapiens

<400> SEQUENCE: 13

| | |
|---|---|
| gagctgaaat tcgcggtgcg acgggaggga gtggagaagg aggtgagggg gcccaggatc | 60 |
| gcggggcgcc ctgaggcaag gggacgccgg tgggtcgaag cgcagcccgc cgcccgcagg | 120 |
| ctcggctccg ccactgccgc cctcccggtc tcctcgcctc gggcgccgag gcagggagag | 180 |
| aatgagcccc gggacccgcc ggggacggc ccgggccagg cccgggatct agaacggccg | 240 |

```
taggggggaag ggagccgccc tccccacggc gccttttcgg aactgccgtg gactcgagga      300
cgctggtcgc cggcctccta gggctgtgct gttttgtttt gaccctcgca ttgtgcagaa      360
ttaaagtgca gtaaaatgtc cactaggacc ccattgccaa cggtgaatga acgagacact      420
gaaaaccaca cgtcacatgg agatgggcgt caagaagtta cctctcgtac cagccgctca      480
ggagctcggt gtagaaactc tatagcctcc tgtgcagatg aacaacctca catcggaaac      540
tacagactgt tgaaaacaat cggcaagggg aattttgcaa aagtaaaatt ggcaagacat      600
atccttacag gcagagaggt tgcaataaaa ataattgaca aaactcagtt gaatccaaca      660
agtctacaaa agctcttcag agaagtaaga ataatgaaga ttttaaatca tcccaatata      720
gtgaagttat tcgaagtcat tgaaactgaa aaaacactct acctaatcat ggaatatgca      780
agtggaggtg aagtatttga ctatttggtt gcacatggca ggatgaagga aaagaagca      840
agatctaaat ttagacagat tgtgtctgca gttcaatact gccatcagaa acggatcgta      900
catcgagacc tcaaggctga aaatctattg ttagatgccg atatgaacat aaaaatagca      960
gatttcggtt ttagcaatga atttactgtt ggcggtaaac tcgacacgtt ttgtggcagt     1020
cctccatacg cagcacctga gctcttccag ggcaagaaat atgacgggcc agaagtggat     1080
gtgtggagtc tgggggtcat tttatacaca ctagtcagtg gctcacttcc ctttgatggg     1140
caaaacctaa aggaactgag agagagagta ttaagaggga aatacagaat tcccttctac     1200
atgtctacag actgtgaaaa ccttctcaaa cgtttcctgg tgctaaatcc aattaaacgc     1260
ggcactctag agcaaatcat gaaggacagg tggatcaatg cagggcatga agaagatgaa     1320
ctcaaaccat tgttgaacc agagctagac atctcagacc aaaaaagaat agatattatg     1380
gtgggaatgg gatattcaca agaagaaatt caagaatctc ttagtaagat gaaatacgat     1440
gaaatcacag ctacatattt gttattgggg agaaaatctt cagagctgga tgctagtgat     1500
tccagttcta gcagcaatct ttcacttgct aaggttaggc cgagcagtga tctcaacaac     1560
agtactggcc agtctcctca ccacaaagtg cagagaagtg tttcttcaag ccaaaagcaa     1620
agacgctaca gtgaccatgc tggaccagct attccttctg ttgtggcgta tccgaaaagg     1680
agtcagacaa gcactgcaga tggtgacctc aaagaagatg gaatttcctc ccggaaatca     1740
agtggcagtg ctgttggagg aaagggaatt gctccagcca gtcccatgct gggaatgca      1800
agtaatccta ataaggcgga tattcctgaa cgcaagaaaa gctccactgt ccctagtagt     1860
aacacagcat ctggtggaat gacacgacga aatacttatg tttgcagtga gagaactaca     1920
gctgatagac actcagtgat tcagaatggc aaagaaaaca gcactattcc tgatcagaga     1980
actccagttg cttcaacaca cagtatcagt agtgcagcca ccccagatcg aatccgcttc     2040
ccaagaggca ctgccagtcg tagcactttc cacggccagc cccgggaacg gcgaaccgca     2100
acatataatg gccctcctgc ctctcccagc ctgtcccatg aagccacacc attgtcccag     2160
actcgaagcc gaggctccac taatctcttt agtaaattaa cttcaaaact cacaaggagt     2220
cgcaatgtat ctgctgagca aaagatgaa aacaaagaag caaagcctcg atccctacgc     2280
ttcacctgga gcatgaaaac cactagttca atggatcccg gggacatgat gcgggaaatc     2340
cgcaaagtgt tggacgccaa taactgcgac tatgagcaga gggagcgctt cttgctcttc     2400
tgcgtccacg gagatgggca gcggagaac ctcgtgcagt gggaaatgga agtgtgcaag     2460
ctgccaagac tgtctctgaa cggggtccgg tttaagcgga tatcggggac atccatagcc     2520
ttcaaaaata ttgcttccaa aattgccaat gagctaaagc tgtaacccag tgattatgat     2580
gtaaattaag tagcaagtaa agtgttttcc tgaacactga tggaaatgta tagaataata     2640
```

```
tttaggcaat aacgtctgca tcttctaaat catgaaatta agtctgagg acgagagc       2698

<210> SEQ ID NO 14
<211> LENGTH: 2914
<212> TYPE: DNA
<213> ORGANISM: Homo sapiens

<400> SEQUENCE: 14
gacggcccgg gccaggcccg ggatctagaa cggccgtagg gggaagggag ccgccctccc        60
cacgcgcct tttcggaact gccgtggact cgaggacgct ggtcgccggc ctcctagggc        120
tgtgctgttt tgttttgacc ctcgcattgt gcagaattaa agtgcagtaa aatgtccact       180
aggaccccat tgccaacggt gaatgaacga gacactgaaa accacacgtc acatggagat       240
gggcgtcaag aagttacctc tcgtaccagc cgctcaggag ctcggtgtag aaactctata       300
gcctcctgtg cagatgaaca acctcacatc ggaaactaca gactgttgaa acaatcggc        360
aaggggaatt ttgcaaaagt aaaattggca agacatatcc ttacaggcag agaggttgca       420
ataaaaataa ttgacaaaac tcagttgaat ccaacaagtc tacaaaagct cttcagagaa       480
gtaagaataa tgaagatttt aaatcatccc aatatagtga agttattcga agtcattgaa       540
actcaaaaaa cactctacct aatcatggaa tatgcaagtg gaggtaaagt atttgactat       600
ttggttgcac atggcaggat gaaggaaaaa gaagcaagat ctaaatttag acagattgtg       660
tctgcagttc aatactgcca tcagaaacgg atcgtacatc gagacctcaa ggctgaaaat       720
ctattgttag atgccgatat gaacattaaa atagcagatt tcggttttag caatgaattt       780
actgttggcg gtaaactcga cacgttttgt ggcagtcctc catacgcagc acctgagctc       840
ttccagggca gaaatatga cgggccagaa gtggatgtgt ggagtctggg ggtcatttta       900
tacacactag tcagtggctc acttcccttt gatgggcaaa acctaaagga actgagagag       960
agagtattaa gagggaaata cagaattccc ttctacatgt ctacagactg tgaaaacctt      1020
ctcaaacgtt tcctggtgct aaatccaatt aaacgcggca ctctagagca aatcatgaag      1080
gacaggtgga tcaatgcagg gcatgaagaa gatgaactca aaccatttgt tgaaccagag      1140
ctagacatct cagaccaaaa agaatagat attatggtgg aatgggata ttcacaagaa        1200
gaaattcaag aatctcttag taagatgaaa tacgatgaaa tcacagctac atatttgtta      1260
ttggggagaa aatcttcaga ggttaggccg agcagtgatc tcaacaacag tactggccag      1320
tctcctcacc acaaagtgca gagaagtgtt tcttcaagcc aaaagcaaag acgctacagt      1380
gaccatgctg gaccaggtat tccttctgtt gtggcgtatc cgaaaaggag tcagaccagc      1440
actgcagata gtgaccctca agaagatgga atttcctccc ggaaatcaac tggcagtgct      1500
gttggaggaa agggaattgc tccagccagt cccatgcttg ggaatgcaag taatcctaat      1560
aaggcggata ttcctgaacg caagaaaagc tccactgtcc ctagtagtaa cacagcatct      1620
ggtggaatga cacgacgaaa tacttatgtt tgcagtgaga gaactacaga tgatagacac      1680
tcagtgattc agaatggcaa agaaaacagc actattcctg atcagagaac tccagttgct      1740
tcaacacaca gtatcagtag tgcagccacc ccagatcgaa tccgcttccc aagaggcact      1800
gccagtcgta gcactttcca cggccagccc cgggaacggc gaaccgcaac atataatggc      1860
cctcctgcct ctcccagcct gtcccatgaa gccacaccat tgtcccagac tcgaagccga      1920
ggctccacta ctctctttag taaattaact tcaaaactca aggagtcg caatgtatct        1980
gctaagcaaa aagatgaaaa caagaagca aagcctcgat ccctacgctt cacctggagc       2040
atgaaaacca ctagttcaat ggatccccggg gacatgatgc gggaaatccg caaagtgttg      2100
```

```
gacgccaata actgcgacta tgagcagagg gagcgcttct tgctcttctg cgtccacgga    2160
gatgggcacg cggagaacct cgtgcagtgg gaaatggaag tgtgcaagct gccaagactg    2220
tctctgaacg gggtccggtt taagcggata tcggggacat ccatagcctt caaaaatatt    2280
gcttccaaaa ttgccaatga gctaaagctg taacccagtg attatgatgt aaattaagta    2340
gcaagtaaag tgttttcctg aacactgatg gaaatgtata gaataatatt taggcaataa    2400
cgtctgcatc ttctaaatca tgaaattaaa gtctgaggac gagagcacgc ctgggagcga    2460
aagctggcct tttttctacg aatgcactac attaaagatg tgcaacctat gcgcccctg     2520 ccctacttcc gttaccctga gagtcggcgt gtggccccat ctccatgtgc ctcccgtctg    2580
ggtgggtgtg agagtggacg gtatgtgtgt gaagtggtgt atatggaagc atctccctac    2640
actggcagcc agtcattact agtacctctg cgggagatca tccggtgcta aaacattaca    2700
gttgccaagg aggaaaatac tgaatgactg ctaagaatta accttaagac cagttcatag    2760
ttaatacagg tttacagttc atgcctgtgg ttttgtgttt ttgttttgt gtttttttag     2820 tgcaaaaggt ttaaatttat agttgtgaac attgcttgtg tgtgttttc taagtagatt    2880 cacaagataa ttaaaaattc acttttctc aggt                                 2914

<210> SEQ ID NO 15
<211> LENGTH: 3895
<212> TYPE: DNA
<213> ORGANISM: Homo sapiens

<400> SEQUENCE: 15
ctgcaggaat tccgatcctt ccgcaggttc acctacggaa accttgttac gacttttact     60
tcctctagat agtcaagttc gaccgtcttc tcagcgctcc gccagggccg tgggccgacc    120
ccggcggggc cgatccgagg gcctcactaa accatccaat cggtagtagc gacgggcggt    180
gtgtacaaag gcagggact taatcaacgc aagcttatga cccgcactta ctgggaattc    240
ctcgttcatg gggaataatt gcaatccccg atccccatca cgaatggggt tcaacgggtt    300
acccgcgcct gccggcgtag ggtaggcaca cgctgagcca gtcagtgtag cgcgcgtgca    360
gccccggaca tctaagggca tcacagacct gttattgctc aatctcgggt ggctgaacgc    420
cacttgtccc tctaagaagt tgggggacgc cgaccgctcg ggggtcgcgt aactagttag    480
catgccagag tctcgttcgt tatcggaatt aaccagacaa atcgctccac caactaagaa    540
cggccatgca ccaccaccca cggaatcgag aaagagctat caatctgtca atcctgtccg    600
tgtccgggcc gggtgaggtt tcccgtgttg agtcaaatta agccgcaggc tccactcctg    660
gtggtgccct tccgtcaatt cctttaagtt tcagctttgc aaccatactc cccccggaac    720
ccaaagactt tggtttcccg gaagctgccc ggcgggtcat gggaataacg ccgccgcatc    780
gccggtcggc atcgtttatg gtcggaacta cgacggtatc tgatcgtctt cgaacctccg    840
actttcgttc ttgattaatg aaaacattct tggcaaatgc tttcgctctg gtccgtcttg    900
cgccggtcca agaatttcgg aattccgcag cggcggccag cagggcggag gctgaggcag    960
caagctcgct agagagggag aagcagtcgg gcgcaggcgc ctcctccgca gcccgctcca   1020
tggtcggcgc ccacagcccg cggcggcctg tcttgcgctc cacttccttc acatcctcct   1080
ccgcctcctc gttttcaggc gccgccggcg gcgctgtgtg gaggccccgcg agctgaaatt   1140 cgcggtgcga cggagggggag tggagaagga ggtgaggggg cccaggatcg cggggcgccc   1200
tgaggcaagg ggacgccggc gggccgaagc gcagcccgcc gcccgcaggc tcggctccgc   1260
cactgccgcc ctcccggtct cctcgcctcg gccgccgagg cagggagaga atgagccccg   1320
```

```
ggacccgccg ggggacggcc cgggccaggc ccgggatcta gacggccgta gggggaaggg   1380
agccgccctc cccacggcgc cttttcggaa ctgccgtgga ctcgaggacg ctggtcgccg   1440
gcctcctagg gctgtgctgt tttgttttga ccctcgcatt gtgcagaatt aaagtgcagt   1500
aaaatgtcca ctaggacccc attgccaacg gtgaatgaac gagacactga aaccacacg    1560 tcacatggag atgggcgtca agaagttacc tctcgtacca gccgctcagg agctcggtgt   1620
agaaactcta tagcctcctg tgcagatgaa caacctcaca tcggaaacta cagactgttg   1680
aaaacaatcg gcaaggggaa ttttgcaaaa gtaaaattgg caagacatat ccttacaggc   1740
agagaggttg caataaaaat aattgacaaa actcagttga atccaacaag tctacaaaag   1800
ctcttcagag aagtaagaat aatgaagatt ttaaatcatc ccaatatagt gaagttattc   1860
gaagtcattg aaactgaaaa aacactctac ctaatcatgg aatatgcaag tggaggtgaa   1920
gtatttgact attggttgc acatggcaag atgaaggaaa aagaagcaag atctaaattt    1980
agacagggtt gtcaagctgg acagactatt aaagttcaag tctcctttga tttgcttagt   2040
ctgatgttta catttattgt gtctgcagtt caatactgcc atcagaaacg gatcgtacat   2100
cgagacctca aggctgaaaa tctattgtta gatgccgata tgaacattaa aatagcagat   2160
ttcggtttta gcaatgaatt tactgttggc ggtaaactcg acacgttttg tggcagtcct   2220
ccatacgcag cacctgagct cttccagggc aagaaatatg acgggccaga agtggatgtg   2280
tggagtctgg gggtcatttt atacacacta gtcagtggct cacttcccTT tgatgggcaa   2340
aacctaaagg aactgagaga gagtatta agagggaaat acagaattcc cttctacatg     2400
tctacagact gtgaaaacct tctcaaacgt ttcctggtgc taaatccaat taaacgcggc   2460
actctagagc aaatcatgaa ggacaggtgg atcaatgcag gcatgaaga agatgaactc    2520 aaaccatttg ttgaaccaga gctagacatc tcagaccaaa aagaataga tattatggtg    2580 ggaatgggat attcacaaga agaaattcaa gaatctctta gtaagatgaa atacgatgaa   2640
atcacagcta catatttgtt attggggaga aaatcttcag agctggatgc tagtgattcc   2700
agttctagca gcaatctttc acttgctaag gttaggccga gcagtgatct caacaacagt   2760
actggccagt ctcctcacca caaagtgcag agaagtgttt cttcaagcca aaagcaaaga   2820
cgctacagtg accatgctgg accagctatt ccttctgttg tggcgtatcc gaaaaggagt   2880
cagacaagca ctgcagatgg tgacctcaaa gaagatggaa tttcctcccg gaaatcaagt   2940
ggcagtgctg ttggaggaaa gggaattgct ccagccagtc ccatgcttgg gaatgcaagt   3000
aatcctaata aggcggatat tcctgaacgc aagaaaagct ccactgtccc tagtagtaac   3060
acagcatctg gtggaatgac acgacgaaat acttatgttt gcagtgagag aactacagct   3120
gatagacact cagtgattca gaatggcaaa gaaaacagca ctattcctga tcagagaact   3180
ccagttgctt caacacacag tatcagtagt gcagccaccc cagatcgaat ccgcttccca   3240
agaggcactg ccagtcgtag cactttccac ggccagcccc gggaacggcg aaccgcaaca   3300
tataatggcc ctcctgcctc tcccagcctg tcccatgaag ccacaccatt gtcccagact   3360
cgaagccgag gctccactaa tctctttagt aaattaactt caaaactcac aaggagtcgc   3420
aatgtatctg ctgagcaaaa agatgaaaac aaagaagcaa agcctcgatc cctacgcttc   3480
acctggagca tgaaaaccac tagttcaatg gatcccgggg acatgatgcg ggaaatccgc   3540
aaagtgttgg acgccaataa ctgcgactat gagcagaggg agcgcttctt gctcttctgc   3600
gtccacggag atgggcacgc ggagaacctc gtgcagtggg aaatggaagt gtgcaagctg   3660
ccaagactgt ctctgaacgg ggtccggttt aagcggatat cggggacatc catagccttc   3720
```

| | | |
|---|---|---|
| aaaaatattg cttccaaaat tgccaatgag ctaaagctgt aacccagtga ttatgatgta | 3780 | |
| aattaagtag caagtaaagt gttttcctga acactgatgg aaatgtatag aataatattt | 3840 | |
| aggcaataac gtctgcatct tctaaatcat gaaattaaag tctgaggacg agagc | 3895 | |

<210> SEQ ID NO 16
<211> LENGTH: 2145
<212> TYPE: DNA
<213> ORGANISM: Homo sapiens

<400> SEQUENCE: 16

| | |
|---|---|
| atgtccacta ggaccccatt gccaacggtg aatgaacgag acactgaaaa ccacacgtca | 60 |
| catggagatg ggcgtcaaga agttacctct cgtaccagcc gctcaggagc tcggtgtaga | 120 |
| aactctatag cctcctgtgc agatgaacaa cctcacatcg gaaactacag actgttgaaa | 180 |
| acaatcggca aggggaattt tgcaaagta aaattggcaa gacatatcct tacaggcaga | 240 |
| gaggttgcaa taaaataat tgacaaaact cagttgaatc aacagtct acaaaagctc | 300 |
| ttcagagaag taagaataat gaagatttta atcatccca atatagtgaa gttattcgaa | 360 |
| gtcattgaaa ctgaaaaaac actctaccta atcatggaat atgcaagtgg aggtgaagta | 420 |
| tttgactatt tggttgcaca tggcaggatg aaggaaaaag aagcaagatc taaatttaga | 480 |
| cagattgtgt ctgcagttca atactgccat cagaaacgga tcgtacatcg agacctcaag | 540 |
| gctgaaaatc tattgttaga tgccgatatg aacattaaaa tagcagattt cggttttagc | 600 |
| aatgaattta ctgttggcgg taaactcgac acgttttgtg gcagtcctcc atacgcagca | 660 |
| cctgagctct tccagggcaa gaaatatgac gggccagaag tggatgtgtg gagtctgggg | 720 |
| gtcattttat acacactagt cagtggctca cttccctttg atgggcaaaa cctaaaggaa | 780 |
| ctgagagaga gagtattaag agggaaatac agaattccct tctacatgtc tacagactgt | 840 |
| gaaaaccttc tcaaacgttt cctggtgcta aatccaatta acgcggcac tctagagcaa | 900 |
| atcatgaagg acaggtggat caatgcaggg catgaagaag atgaactcaa accatttgtt | 960 |
| gaaccagagc tagacatctc agaccaaaaa gaatagata ttatggtggg aatgggatat | 1020 |
| tcacaagaag aaattcaaga atctcttagt aagatgaaat acgatgaaat cacagctaca | 1080 |
| tatttgttat tggggagaaa atcttcagag gttaggccga gcagtgatct caacaacagt | 1140 |
| actggccagt ctcctcacca caaagtgcag agaagtgttt cttcaagcca aaagcaaaga | 1200 |
| cgctacagtg accatgctgg accagctatt ccttctgttg tggcgtatcc gaaaggagt | 1260 |
| cagaccagca ctgcagatag tgacctcaaa gaagatggaa tttcctcccg gaaatcaagt | 1320 |
| ggcagtgctg ttggaggaaa gggaattgct ccagccagtc ccatgcttgg gaatgcaagt | 1380 |
| aatcctaata aggcggatat tcctgaacgc aagaaaagct ccactgtccc tagtagtaac | 1440 |
| acagcatctg gtggaatgac acgacgaaat acttatgttt gcagtgagag aactacagct | 1500 |
| gatagacact cagtgattca gaatggcaaa gaaaacagca ctattcctga tcagagaact | 1560 |
| ccagttgctt caacacagag tatcagtagt gcagccaccc cagatcgaat ccgcttccca | 1620 |
| agaggcactg ccagtcgtag cactttccac ggccagcccc gggaacggcg aaccgcaaca | 1680 |
| tataatggcc ctcctgcctc tcccagcctg tcccatgaag ccacaccatt gtcccagact | 1740 |
| cgaagccgag gctccactaa tctctttagt aaattaactt caaaactcac aaggagtcgc | 1800 |
| aatgtatctg ctgagcaaaa agatgaaaac aaagaagcaa agcctcgatc cctacgcttc | 1860 |
| acctggagca tgaaaaccac tagttcaatg gatcccgggg acatgatgcg ggaaatccgc | 1920 |
| aaagtgttgg acgccaataa ctgcgactat gagcagaggg agcgcttctt gctcttctgc | 1980 |

```
gtccacggag atgggcacgc ggagaacctc gtgcagtggg aaatggaagt gtgcaagctg   2040
ccaagactgt ctctgaacgg ggtccggttt aagcggatat cggggacatc catagccttc   2100
aaaaatattg cttccaaaat tgccaatgag ctaaagctgt aaccc                   2145

<210> SEQ ID NO 17
<211> LENGTH: 2193
<212> TYPE: DNA
<213> ORGANISM: Homo sapiens

<400> SEQUENCE: 17
atgtccacta ggaccccatt gccaacggtg aatgaacgag acactgaaaa ccacacgtca     60
catggagatg ggcgtcaaga agttacctct cgtaccagcc gctcaggagc tcggtgtaga    120
aactctatag cctcctgtgc agatgaacaa cctcacatcg gaaactacag actgttgaaa    180
acaatcggca aggggaattt tgcaaaagta aaattggcaa gacatatcct tacaggcaga    240
gaggttgcaa taaaataat tgacaaaact cagttgaatc aacaagtct acaaaagctc      300 ttcagagaag taagaataat gaagatttta atcatccca atatagtgaa gttattcgaa     360
gtcattgaaa ctgaaaaaac actctaccta atcatggaat atgcaagtgg aggtgaagta    420
tttgactatt tggttgcaca tggcaggatg aaggaaaaag aagcaagatc taaatttaga    480
cagattgtgt ctgcagttca atactgccat cagaaacgga tcgtacatcg agacctcaag    540
gctgaaaatc tattgttaga tgccgatatg aacattaaaa tagcagattt cggttttagc    600
aatgaattta ctgttggcgg taaactcgac acgttttgtg gcagtcctcc atacgcagca    660
cctgagctct tccagggcaa gaaatatgac gggccagaag tggatgtgtg gagtctgggg    720 gtcatttat acacactagt cagtggctca cttcccttg atgggcaaaa cctaaaggaa      780
ctgagagaga gagtattaag agggaaatac agaattccct tctacatgtc tacagactgt    840
gaaaaccttc tcaaacgttt cctggtgcta aatccaatta aacgcggcac tctagagcaa    900
atcatgaagg acaggtggat caatgcaggg catgaagaag atgaactcaa accatttgtt    960
gaaccagagc tagacatctc agaccaaaaa agaatagata ttatggtggg aatgggatat   1020
tcacaagaag aaattcaaga atctcttagt aagatgaaat acgatgaaat cacagctaca   1080
tatttgttat ggggagaaa atcttcagag ctggatgcta gtgattccag ttctagcagc    1140
aatctttcac ttgctaaggt taggccgagc agtgatctca caacagtac tggccagtct    1200 cctcaccaca aagtgcagag aagtgttttct caagccaaa agcaaagacg ctacagtgac   1260
catgctggac cagctattcc ttctgttgtg gcgtatccga aaaggagtca gaccagcact   1320
gcagatagtg acctcaaaga agatggaatt tcctcccgga aatcaagtgg cagtgctgtt   1380
ggaggaaagg gaattgctcc agccagtccc atgcttggga atgcaagtaa tcctaataag   1440
gcggatattc ctgaacgcaa gaaaagctcc actgtcccta gtagtaacac agcatctggt   1500
ggaatgacac gacgaaatac ttatgttgc agtgagagaa ctacagctga tagacactca   1560
gtgattcaga atggcaaaga aaacagcact attcctgatc agagaactcc agttgcttca   1620
acacacagta tcagtagtgc agccacccca gatcgaatcc gcttcccaag aggcactgcc   1680
agtcgtagca ctttccacgg ccagccccgg gaacggcgaa ccgcaacata taatggccct   1740
cctgcctctc ccagcctgtc ccatgaagcc acaccattgt cccagactcg aagccgaggc   1800
tccactaatc tctttagtaa attaacttca aaactcacaa ggagtcgcaa tgtatctgct   1860
gagcaaaaag atgaaaacaa agaagcaaag cctcgatccc tacgcttcac ctggagcatg   1920
aaaaccacta gttcaatgga tcccggggac atgatgcggg aaatccgcaa agtgttggac   1980
```

```
gccaataact gcgactatga gcagagggag cgcttcttgc tcttctgcgt ccacggagat      2040
gggcacgcgg agaacctcgt gcagtgggaa atggaagtgt gcaagctgcc aagactgtct      2100
ctgaacgggg tccggtttaa gcggatatcg gggacatcca tagccttcaa aaatattgct      2160
tccaaaattg ccaatgagct aaagctgtaa ccc                                   2193
```

<210> SEQ ID NO 18
<211> LENGTH: 3373
<212> TYPE: DNA
<213> ORGANISM: Homo sapiens

<400> SEQUENCE: 18

```
caggcgcctc ctccgcagcc cgctccatgg tcggcgccca cagcccgcgg cggcctgtct       60
tgcgctccac ttccttcaca tcctcctccg cctcctcgtt ttcaggcgcc gccggcggcg      120
ctgtgtggag gcccgcgagc tgaaattcgc ggtgcgacgg gagggagtgg agaaggaggt      180
gaggggcccc aggatcgcgg ggcgccctga ggcaagggga cgccggcggg ccgaagcgca      240
gcccgccgcc cgcaggctcg gctccgccac tgccgccctc ccggtctcct cgcctcggcc      300
gccgaggcag ggagagaatg agccccggga cccgccgggg acggcccggg ccaggcccgg      360
gatctagaac ggccgtaggg ggaagggagc cgccctcccc acggcgcctt ttcggaactg      420
ccgtggactc gaggacgctg gtcgccggcc tcctagggct gtgctgtttt gttttgaccc      480
tcgcattgtg cagaattaaa gtgcagtaaa atgtccacta ggaccccatt gccaacggtg      540
aatgaacgag acactgaaaa ccacacgtca catggagatg ggcgtcaaga agttacctct      600
cgtaccagcc gctcaggagc tcggtgtaga aactctatag cctcctgtgc agatgaacaa      660
cctcacatcg gaaactacag actgttgaaa acaatcggca aggggaattt tgcaaaagta      720
aaattggcaa gacatatcct tacaggcaga gaggttgcaa taaaaataat tgacaaaact      780
cagttgaatc caacaagtct acaaaagctc ttcagagaag taagaataat gaagatttta      840
aatcatccca atatagtgaa gttattcgaa gtcattgaaa ctgaaaaaac actctaccta      900
atcatggaat atgcaagtgg aggtaaagta tttgactatt tggttgcaca tggcaggatg      960
aaggaaaaag aagcaagatc taaatttaga cagattgtgt ctgcagttca atactgccat     1020
cagaaacgga tcgtacatcg agacctcaag gctgaaaatc tattgttaga tgccgatatg     1080
aacattaaaa tagcagattt cggttttagc aatgaattta ctgttggcgg taaactcgac     1140
acgttttgtg gcagtcctcc atacgcagca cctgagctct tccagggcaa gaaatatgac     1200
gggccagaag tggatgtgtg gagtctgggg gtcattttat acacactagt cagtggctca     1260 cttcccttg atgggcaaaa cctaaaggaa ctgagagaga gagtattaag agggaaatac     1320
agaattccct tctacatgtc tacagactgt gaaaaccttc tcaaacgttt cctggtgcta     1380
aatccaatta acgcggcac tctagagcaa atcatgaagg acaggtggat caatgcaggg     1440
catgaagaag atgaactcaa accatttgtt gaaccagagc tagacatctc agaccaaaaa     1500
agaatagata ttatggtggg aatgggatat tcacaagaag aaattcaaga atctcttagt     1560
aagatgaaat acgatgaaat cacagctaca tatttgttat ggggagaaa atcttcagag     1620 ctggatgcta gtgattccag ttctagcagc aatctttcac ttgctaaggt taggccgagc     1680
agtgatctca caacagtac tggccagtct cctcaccaca aagtgcagag aagtgttttct     1740 tcaagccaaa agcaaagacg ctacagtgac catgctggac cagctattcc ttctgttgtg     1800
gcgtatccga aaaggagtca gaccagcact gcagatagtg acctcaaaga agatggaatt     1860
tcctcccgga aatcaagtgg cagtgctgtt ggaggaaagg gaattgctcc agccagtccc     1920
```

```
atgcttggga atgcaagtaa tcctaataag gcggatattc ctgaacgcaa gaaaagctcc   1980
actgtcccta gtagtaacac agcatctggt ggaatgacac gacgaaatac ttatgtttgc   2040
agtgagagaa ctacagctga tagacactca gtgattcaga atggcaaaga aaacagcact   2100
attcctgatc agagaactcc agttgcttca acacacagta tcagtagtgc agccacccca   2160
gatcgaatcc gcttcccaag aggcactgcc agtcgtagca cttccacgg ccagccccgg    2220
gaacggcgaa ccgcaacata taatggccct cctgcctctc ccagcctgtc ccatgaagcc   2280
acaccattgt cccagactcg aagccgaggc tccactaatc tctttagtaa attaacttca   2340
aaactcacaa ggagaaacat gtcattcagg tttatcaaaa ggcttccaac tgaatatgag   2400
aggaacggga gatatgaggg ctcaagtcgc aatgtatctg ctgagcaaaa agatgaaaac   2460
aaagaagcaa agcctcgatc cctacgcttc acctggagca tgaaaaccac tagttcaatg   2520
gatcccgggg acatgatgcg ggaaatccgc aaagtgttgg acgccaataa ctgcgactat   2580
gagcagaggg agcgcttctt gctcttctgc gtccacggag atgggcacgc ggagaacctc   2640
gtgcagtggg aaatggaagt gtgcaagctg ccaagactgt ctctgaacgg ggtccggttt   2700
aagcggatat cggggacatc catagccttc aaaaatattg cttccaaaat tgccaatgag   2760
ctaaagctgt aacccagtga ttatgatgta aattaagtag caagtaaagt gttttcctga   2820
acactgatgg aaatgtatag aataatattt aggcaataac gtctgcatct tctaaatcat   2880
gaaattaaag tctgaggacg agagcacgcc tgggagcgaa agctggcctt ttttctacga   2940
atgcactaca ttaaagatgt gcaacctatg cgccccctgc cctacttccg ttaccctgag   3000
agtcggcgtg tggccccatc tccatgtgcc tcccgtctgg gtgggtgtga gagtggacgg   3060
tatgtgtgtg aagtggtgta tatggaagca tctccctaca ctggcagcca gtcattacta   3120
gtacctctgc gggagatcat ccggtgctaa acattacag ttgccaagga ggaaaatact    3180
gaatgactgc taagaattaa ccttaagacc agttcatagt taatacaggt ttacagttca   3240
tgcctgtggt tttgtgtttg ttgttttgtg ttttttagt gcaaaaggtt taaatttata    3300
gttgtgaaca ttgcttgtgt gtgtttttct aagtagattc acaagataat taaaaattca   3360
cttttttctca ggt                                                    3373
```

<210> SEQ ID NO 19
<211> LENGTH: 3609
<212> TYPE: DNA
<213> ORGANISM: Homo sapiens
<220> FEATURE:
<221> NAME/KEY: misc_feature
<222> LOCATION: (3606)..(3606)
<223> OTHER INFORMATION: "n" is A, C, G, or T

<400> SEQUENCE: 19

```
cgcctccctc cgccgccgct tgggccggct ccgcgccccc tccgcggccc ccgcccgccc    60
gcctgcccgc cgcccccatg gcgcccgggg tccccgctgc acgggccac taggaccctc     120
ggcgtccctt cccctccccc gccctgcccc ctctcccgcc gcgcggaccc gggcgttctc    180
ggcgcccagc ttttgagctc gcgtcccag gccggcgggg ggagggga agagagggga      240
ccctgggacc ccgcccccc cacccggcc gccctgccc ccgggaccc ggagaagatg        300
tcttcgcgga cggtgctggc cccgggcaac gatcggaact cggacacgca tggcaccttg    360
ggcagtggcc gctcctcgga caaaggcccg tcctggtcca gccgctcact gggtgcccgt    420
tgccggaact ccatcgcctc ctgtcccgag gagcagcccc acgtgggcaa ctaccgcctg    480
ctgaggacca ttgggaaggg caactctgcc aaagtcaagc tggctcggca catcctcact    540
```

```
ggtcgggagg ttgccatcaa gattatcgac aaaacccagc tgaatcccag cagcctgcag    600
aagctgttcc gagaagtccg catcatgaag ggcctaaacc accccaacat cgtgaagctc    660
tttgaggtga ttgagactga aaagacgctg tacctggtga tggagtacgc aagtgctgga    720
gaagtgtttg actacctcgt gtcgcatggc cgcatgaagg agaaggaagc tcgagccaag    780
ttccgacaga ttgtttcggc tgtgcactat tgtcaccaga aaatattgt acacagggac      840 ctgaaggctg agaacctctt gctggatgcc gaggccaaca tcaagattgc tgactttggc    900
ttcagcaacg agttcacgct gggatcgaag ctggacacgt tctgcgggag cccccccatat  960 gccgccccgg agctgtttca gggcaagaag tacgacgggc cggaggtgga catctggagc   1020 ctggagtca tcctgtacac cctcgtcagc ggctccctgc ccttcgacgg cacaacctc      1080 aaggagctgc gggagcgagt actcagaggg aagtaccggg tccctttcta catgtcaaca    1140
gactgtgaga gcatcctgcg agattttttg gtgctgaacc cagctaaacg ctgtactctc    1200
gagcaaatca tgaaagacaa atggatcaac atcggctatg agggtgagga gttgaagcca    1260
tacacagagc ccgaggagga cttcgggac accaagagaa ttgaggtgat ggtgggtatg     1320
ggctacacac gggaagaaat caaagagtcc ttgaccagcc agaagtacaa cgaagtgacc    1380
gccacctacc tcctgctggg caggaagact gaggagggtg gggaccgggg cgccccaggg    1440
ctggccctgg cacgggtgcg gcgcccagc gacaccacca acggaacaag ttccagcaaa     1500
ggcaccagcc acagcaaagg cagcggagt tcctcttcca cctaccaccg ccagcgcagg     1560
catagcgatt tctgtggccc atcccctgca ccctgcacc caaacgcag cccgacgagc      1620 acggggggagg cggagctgaa ggaggagcgg ctgccaggcc ggaaggcgag ctgcagcacc   1680
gcggggagtg ggagtcgagg gctgcccccc tccagcccca tggtcagcag cgcccacaac   1740
cccaacaagg cagagatccc agagcggcgg aaggacagca cgagcacccc caacaacctc   1800
cctcctagca tgatgacccg cagaaacacc tacgtttgca cagaacgccc gggggctgag   1860
cgcccgtcac tgttgccaaa tgggaaagaa aacagctcag gcaccccacg ggtgcccct    1920 gcctcccccct ccagtcacag cctggcaccc ccatcagggg agcggagccg cctggcacgc  1980
ggttccacca tccgcagcac cttccatggt ggccaggtcc gggaccggcg gcagggggt    2040 gggggtggtg gggtgtgca gaatgggccc cctgcctctc ccacactggc ccatgaggct    2100
gcacccctgc ccgccgggcg gccccgcccc accaccaacc tcttcaccaa gctgacctcc   2160
aaactgaccc gaagggttac cctcgatccc tctaaacggc agaactctaa ccgctgtgtt   2220
tcgggcgcct ctctgcccca gggatccaag atcaggtcgc agacgaacct gagagaatcg   2280
ggggacctga ggtcacaagt tgccatctac cttgggatca aacggaaacc gccccccggc  2340
tgctccgatt cccctggagt gtgaagctga ccagctcgcg ccctcctgag gccctgatgg   2400
cagctctgcg ccaggccaca gcagccgccc gctgccgctg ccgccagcca cagccgttcc   2460
tgctggcctg cctgcacggg ggtgcgggcg ggcccgagcc cctgtcccac ttcgaagtgg   2520
aggtctgcca gctgccccgg ccaggcttgc ggggagttct cttccgccgt gtggcgggca   2580
ccgccctggc cttccgcacc ctcgtcaccc gcatctccaa cgacctcgag ctctgagcca   2640
ccacggtccc agggccctta ctcttcctct cccttgtcgc cttcacttct acagaggggg   2700
aaggggccag ggagggggatt ctccctttat catcacctca gtttccctga attatatttg   2760
ggggcaaaga ttgtcccctc tgctgttctc tggggccgct cagcacagaa gaaggatgag   2820
ggggctcagc gggggagct ggcacctcc tggagcctcc agccagtcct gtcctccctc     2880
gccctaccaa gagggcacct gaggagactt tggggacagg gcaggggcag ggagggaaac   2940
```

```
tgaggaaatc ttccattcct cccaacagct caaaattagg ccttgggcag gggcagggag    3000
agctgctgag cctaaagact ggagaatctg ggggactggg agtgggggtc agagaggcag    3060
attccttccc ctcccgtccc ctcacgctca aaccccccact tcctgcccca ggctggcgcg    3120
gggcactttg tacaaatcct tgtaaatacc ccacaccctc ccctctgcaa aggtctcttg    3180
aggagctgcc gctgtcacct acggttttta agttattaca ccccgacccct cctcctgtca    3240 gccccctcac ctgcagcctg ttgcccaata aatttaagag agtcccccccc tccccaatgc    3300 tgaccctagg attttccttc cctgccctca cctgcaaatg agttaaagaa gaggcgtggg    3360
aatccaggca gtggtttttc ctttcggagc ctcggttttc tcatctgcag aatgggagcg    3420 gtggggggtgg gaaggtaagg atggtcgtgg aagaaggcag gatggaactc ggcctcatcc    3480
ccgaggcccc agttcctata tcgggccccc cattcatcca ctcacactcc cagccaccat    3540
gttacactgg actctaagcc acttcttact ccagtagtaa atttattgca ataaacaatc    3600 attganccc                                                            3609

<210> SEQ ID NO 20
<211> LENGTH: 2085
<212> TYPE: DNA
<213> ORGANISM: Homo sapiens

<400> SEQUENCE: 20
agatgtcttc gcggacggtg ctggccccgg gcaacgatcg gaactcggac acgcatggca      60
ccttgggcag tggccgctcc tcggacaaag gcccgtcctg gtccagccgc tcactgggtg     120
cccgttgccg gaactccatc gcctcctgtc ccgaggagca gccccacgtg ggcaactacc     180
gcctgctgag gaccattggg aagggcaact ttgccaaagt caagctggct cggcacatcc     240
tcactggtcg ggaggttgcc atcaagatta tcgacaaaac ccagctgaat cccagcagcc     300
tgcagaagct gttccgagaa gtccgcatca tgaagggcct aaaccacccc aacatcgtga     360
agctctttga ggtgattgag actgagaaga cgctgtacct ggtgatggag tacgcaagtg     420
ctggagaagt gtttgactac ctcgtgtcgc atggccgcat gaaggagaag gaagctcgag     480
ccaagttccg acagattgtt tcggctgtgc actattgtca ccagaaaaat attgtacaca     540
gggacctgaa ggctgagaac ctcttgctgg atgccgaggc caacatcaag attgctgact     600
ttggcttcag caacgagttc acgctgggat cgaagctgga cacgttctgc gggagccccc     660
catatgccgc cccggagctg tttcagggca gaaagtacga cggccggag gtggacatct     720 ggagcctggg agtcatcctg tacacccctcg tcagcggctc cctgcccttc gacgggcaca     780
acctcaagga gctgcgggag cgagtactca gagggaagta ccgggtccct ttctacatgt     840
caacagactg tgagagcatc ctgcggagat ttttggtgct gaacccagct aaacgctgta     900
ctctcgagca aatcatgaaa gacaaatgga tcaacatcgg ctatgagggt gaggagttga     960
agccatacac agagcccgag gaggacttcg gggacaccaa gagaattgag gtgatggtgg    1020
gtatgggcta cacacgggaa gaaatcaaag agtccttgac cagccagaag tacaacgaag    1080
tgaccgccac ctacctcctg ctgggcagga agactgagga gggtgtgggac cggggcgccc    1140 cagggctggc cctggcacgg gtgcgggcgc ccagcgacac caccaacgga acaagttcca    1200
gcaaaggcac cagccacagc aaagggcagc ggagttcctc ttccacctac caccgccagc    1260
gcaggcatag cgatttctgt ggcccatccc ctgcaccct gcacccccaaa cgcagcccga    1320 cgagcacggg gaggcggag ctgaaggagg agcggctgcc aggccggaag gcgagctgca    1380
gcaccgcggg gagtgggagt cgagggctgc cccctccag ccccatggtc agcagcgccc    1440
```

```
acaaccccaa caaggcagag atcccagagc ggcggaagga cagcacgagc accccccaaca    1500
acctccctcc tagcatgatg acccgcagaa acacctacgt ttgcacagaa cgcccggggg    1560
ctgagcgccc gtcactgttg ccaaatggga agaaaacag ctcaggcacc ccacgggtgc     1620
cccctgcctc cccctccagt cacagcctgg cacccccatc aggggagcgg agccgcctgg    1680
cacgcggttc caccatccgc agcaccttcc atggtggcca ggtccgggac cggcgggcag    1740
ggggtggggg tggtgggggt gtgcagaatg gccccctgc ctctcccaca ctggcccatg     1800
aggctgcacc cctgcccgcc gggcggcccc gccccaccac caacctcttc accaagctga    1860
cctccaaact gacccgaagg gttaccctcg atccctctaa acggcagaac tctaaccgct    1920
gtgtttcggg cgcctctctg ccccagggat ccaagatcag gtcgcagacg aacctgagag    1980
aatcggggga cctgaggtca caagttgcca tctaccttgg gatcaaacgg aaaccgcccc    2040
ccggctgctc cgattcccct ggagtgtgaa gctgaccagc tcgcg                    2085
```

<210> SEQ ID NO 21
<211> LENGTH: 2278
<212> TYPE: DNA
<213> ORGANISM: Homo sapiens

<400> SEQUENCE: 21

```
agatgtcttc gcggacggtg ctggccccgg gcaacgatcg gaactcggac acgcatggca      60
ccttgggcag tggccgctcc tcggacaaag gcccgtcctg gtccagccgc tcactgggtg     120
cccgttgccg gaactccatc gcctcctgtc ccgaggagca gccccacgtg ggcaactacc     180
gcctgctgag gaccattggg aagggcaact tgccaaagt caagctggct cggcacatcc      240
tcactggtcg ggaggttgcc atcaagatta tcgacaaaac ccagctgaat cccagcagcc     300
tgcagaagct gttccgagaa gtccgcatca tgaagggcct aaaccacccc aacatcgtga    360
agctctttga ggtgattgag actgagaaga cgctgtacct ggtgatggag tacgcaagtg    420
ctggagaagt gtttgactac ctcgtgtcgc atggccgcat gaaggagaag gaagctcgag    480
ccaagttccg acagattgtt tcggctgtgc actattgtca ccagaaaaat attgtacaca    540
gggacctgaa ggctgagaac ctcttgctgg atgccgaggc caacatcaag attgctgact    600
ttggcttcag caacgagttc acgctgggat cgaagctgga cacgttctgc gggagccccc    660
catatgccgc cccggagctg tttcagggca agaagtacga cggccggag gtggacatct    720
ggagcctggg agtcatcctg tacaccctcg tcagcggctc cctgcccttc gacgggcaca    780
acctcaagga gctgcgggag cgagtactca gagggaagta ccgggtccct ttctacatgt    840
caacagactg tgagcatc ctgcggagat ttttggtgct gaacccagct aaacgctgta     900
ctctcgagca aatcatgaaa gacaaatgga tcaacatcgg ctatgagggt gaggagttga    960
agccatacac agagcccgag gaggacttcg gggacaccaa gagaattgag gtgatggtgg   1020
gtatgggcta cacgcgggaa gaaatcaaag agtccttgac cagccagaag tacaacgaag   1080
tgaccgccac ctacctcctg ctgggcagga agactgagga gggtgggac cggggcgccc    1140
cagggctggc cctggcacgg gtgcgggcgc ccagcgacac caccaacgga caagttcca     1200
gcaaaggcac cagccacagc aaagggcagc ggagttcctc ttccacctac caccgccagc    1260
gcaggcatag cgatttctgt ggcccatccc ctgcaccct gcaccccaaa cgcagccga     1320
cgagcacgcg ggaggcggag ctgaaggagg agccggctgcc aggccggaag gcgagctgca   1380
gcaccgcggg gagtgggagt cgagggctgc cccctccag ccccatggtc agcagcgccc    1440
acaaccccaa caaggcagag atcccagagc ggcggaagga cagcacgagc accccccaaca  1500
```

| | |
|---|---|
| acctccctcc tagcatgatg acccgcagaa acacctacgt ttgcacagaa cgcccggggg | 1560 |
| ctgagcgccc gtcactgttg ccaaatggga agaaaacag ctcaggcacc ccacgggtgc | 1620 |
| ccctgcctc ccctccagt cacagcctgg caccccatc aggggagcgg agccgcctgg | 1680 |
| cacgcggttc caccatccgc agcaccttcc atggtggcca ggtccgggac cggcgggcag | 1740 |
| ggggtggggg tggtgggggt gtgcagaatg ggcccctgc ctctcccaca ctggcccatg | 1800 |
| aggctgcacc cctgcccgcc gggcggcccc gccccaccac caacctcttc accaagctga | 1860 |
| cctccaaact gacccgaagg gtcgcagacg aacctgagag aatcggggga cctgaggtca | 1920 |
| caagttgcca tctaccttgg gatcaaacgg aaaccgcccc ccggctgctc cgattcccct | 1980 |
| ggagtgtgaa gctgaccagc tcgcgccctc ctgaggccct gatggcagct ctgcgccagg | 2040 |
| ccacagcagc cgcccgctgc cgctgccgcc agccacagcc gttcctgctg gcctgcctgc | 2100 |
| acggggtgc gggcgggccc gagccctgt cccacttcga agtggaggtc tgccagctgc | 2160 |
| cccggccagg cttgcgggga gttctcttcc gccgtgtggc gggcaccgcc ctggccttcc | 2220 |
| gcaccctcgt cacccgcatc tccaacgacc tcgagctctg agccaccacg gtcccagg | 2278 |

<210> SEQ ID NO 22
<211> LENGTH: 4917
<212> TYPE: DNA
<213> ORGANISM: Homo sapiens

<400> SEQUENCE: 22

| | |
|---|---|
| agaagatgtc ttcgcggacg gtgctggccc cgggcaacga tcggaactcg gacacgcatg | 60 |
| gcaccttggg cagtggccgc tcctcggaca aaggcccgtc ctggtccagc cgctcactgg | 120 |
| gtgcccgttg ccggaactcc atcgcctcct gtcccgagga gcagcccac gtgggcaact | 180 |
| accgcctgct gaggaccatt gggaagggca actttgccaa agtcaagctg gctcggcaca | 240 |
| tcctcactgg tcgggaggtt gccatcaaga ttatcgacaa aacccagctg aatcccagca | 300 |
| gcctgcagaa gctgttccga gaagtccgca tcatgaaggg cctaaaccac cccaacatcg | 360 |
| tgaagctctt tgaggtgatt gagactgaga agacgctgta cctggtgatg gagtacgcaa | 420 |
| gtgctggaga agtgtttgac tacctcgtgt cgcatggccg catgaaggag aaggaagctc | 480 |
| gagccaagtt ccgacagatt gtttcggctg tgcactattg tcaccagaaa aatattgtac | 540 |
| acagggacct gaaggctgag aacctcttgc tggatgccga ggccaacatc aagattgctg | 600 |
| actttggctt cagcaacgag ttcacgctgg gatcgaagct ggacacgttc tgcgggagcc | 660 |
| ccccatatgc cgccccggag ctgtttcagg gcaagaagta cgacgggccg gaggtggaca | 720 |
| tctggagcct gggagtcatc ctgtacaccc tcgtcagcgg ctccctgccc ttcgacgggc | 780 |
| acaacctcaa ggagctgcgg gagcgagtac tcagagggaa gtaccgggtc cctttctaca | 840 |
| tgtcaacaga ctgtgagagc atcctgcgga gatttttggt gctgaaccca gctaaacgct | 900 |
| gtactctcga gcaaatcatg aaagacaaat ggatcaacat cggctatgag ggtgaggagt | 960 |
| tgaagccata cacagagccc gaggaggact tcgggacac caagagaatt gaggtgatgg | 1020 |
| tgggtatggg ctacacacgg gaagaaatca aagagtcctt gaccagccag aagtacaacg | 1080 |
| aagtgaccgc cacctacctc ctgctgggca ggaagactga ggagggtggg gaccggggcg | 1140 |
| ccccagggct ggccctggca cgggtgcggg cgcccagcga caccaccaac ggaacaagtt | 1200 |
| ccagcaaagg caccagccac agcaaagggc agcggagttc ctcttccacc taccaccgcc | 1260 |
| agcgcaggca tagcgatttc tgtggcccat ccctgcacc cctgcacccc aaacgcagcc | 1320 |
| cgacgagcac gggggaggcg gagctgaagg aggagcggct gccaggccgg aaggcgagct | 1380 |

```
gcagcaccgc ggggagtggg agtcgagggc tgccccctc  cagccccatg gtcagcagcg   1440
cccacaaccc caacaaggca gagatcccag agcggcggaa ggacagcacg agcaccccca   1500
acaacctccc tcctagcatg atgacccgca gaaacaccta cgtttgcaca gaacgcccgg   1560
gggctgagcg cccgtcactg ttgccaaatg ggaaagaaaa cagctcaggc accccacggg   1620
tgccccctgc ctcccctcc  agtcacagcc tggcaccccc atcaggggag cggagccgcc   1680
tggcacgcgg ttccaccatc cgcagcacct tccatggtgg ccaggtccgg gaccggcggg   1740
caggggtgg  gggtggtggg ggtgtgcaga atgggccccc tgcctctccc acactggccc   1800
atgaggctgc accctgccc  gccgggcggc cccgccccac caccaacctc ttcaccaagc   1860
tgacctccaa actgacccga agggttaccc tcgatccctc taaacggcag aactctaacc   1920
gctgtgtttc gggcgcctct ctgccccagg gatccaagat caggtcgcag acgaacctga   1980
gagaatcggg ggacctgagg tcacaagttg ccatctacct tgggatcaaa cggaaaccgc   2040
cccccggctg ctccgattcc cctggagtgt gaagctgacc agctcgcgcc ctcctgaggc   2100
cctgatggca gctctgcgcc aggccacagc agccgcccgc tgccgctgcc gccagccaca   2160
gccgttcctg ctggcctgcc tgcacggggg tgcgggcggg cccgagcccc tgtcccactt   2220
cgaagtggag gtctgccagc tgccccggcc aggcttgcgg ggagttctct ccgccgtgt   2280
ggcgggcacc gccctggcct tccgcaccct cgtcacccgc atctccaacg acctcgagct   2340
ctgagccacc acggtcccag ggcccttact cttcctctcc cttgtcgcct tcacttctac   2400
aggaggggaa ggggccaggg aggggattct ccctttatca tcacctcagt ttccctgaat   2460
tatatttggg ggcaaagatt gtcccctctg ctgttctctg gggccgctca gcacagaaga   2520
aggatgaggg ggctcagcgg ggggagctgg caccttcctg gagcctccag ccagtcctgt   2580
cctccctcgc cctaccaaga gggcacctga ggagactttg gggacagggc aggggcaggg   2640
agggaaactg aggaaatctt ccattcctcc caacagctca aaattaggcc ttgggcaggg   2700
gcagggagag ctgctgagcc taaagactgg agaatctggg ggactgggag tgggggtcag   2760
agaggcagat tccttcccct cccgtcccct cacgctcaaa ccccccacttc ctgccccagg   2820
ctggcgcggg gcactttgta caaatccttg taaataccccc acaccctccc ctctgcaaag   2880
gtctcttgag gagctgccgc tgtcacctac ggttttttaag ttattacacc ccgaccctcc   2940
tcctgtcagc cccctcacct gcagcctgtt gcccaataaa tttaagagag tcccccctc   3000
cccaatgctg accctaggat tttccttccc tgccctcacc tgcaaatgag ttaaagaaga   3060
ggcgtgggaa tccaggcagt ggttttttcct ttcggagcct cggttttctc atctgcagaa   3120
tgggagcggt gggggtggga aggtaaggat ggtcgtggaa gaaggcagga tggaactcgg   3180
cctcatcccc gaggcccag  ttcctatatc gggccccca  ttcatccact cacactccca   3240
gccaccatgt tacactggac tctaagccac ttcttactcc agtagtaaat ttattcaata   3300
aacaatcatt gacccatgcc tactccatgc caggcccagt gctggacaca gagacatgaa   3360
gctctgtctg tgggagacag ggattctgac acagacaccg gacaaaccat tgtcttgggg   3420
agcccagaag agaaagtggg cagggtgggg tcattgggga agatgctcta gaggaattaa   3480
tgctggaatg gggtgttgaa ggatgagtag gagttagtta ggcattgagt ttgccctggg   3540
caaaagccca gaagtgggag tatgtggtat atcttcagag aactgggtaa tttcagtgtg   3600
gctgctgtgt tgggcatgga tggagaatca gcaagagaaa tgctgtatta ggactaataa   3660
tccatctacg ctgcttaagc aaaaaggtat ttgttggttt atgttactta atagtccagg   3720
ggcacctggc ttcaggtagg tttgatccag gcatcaggcc attgcatcta ttttttcagt   3780
```

```
gtaagttgaa ttctagtaat ttttatcaag taagggctcc tttcctggtg gcacagatga   3840
cttcagcagt tagaagtttc tatccctcca gctttctgca gcagaaagac cctcattgtc   3900
agtttcccag caaaagtccc agggcagact ctcattggcc caaatgggcc atgtgatttt   3960
ctctaaacca atcactgtga ctctagagtg gccagactca gagctgcact tagtaggggt   4020
tcctcaaagg aaggtcaagt gtcatgagca ggagaaaagg catgggagct ggacagatta   4080
tagtggttga agtctgtgca gtacagaagg gcggagctta ttcacacagc acctttgggg   4140
ccaaaatgaa taagctggac tttctcccca tggcactggg gaaccatgga agttcaggga   4200
acttcaggga agaggcttgg tcaattcctg agagcatcct ctgtgctggg gacacagtgg   4260
taatcaagac agccccaaca ctgccctcat agagctcaca gtccaatgga ggaggcagat   4320
gtgtcctcag gcagcgactg ggcagggctg gtataggga gtccagaggt gatgcctgcc    4380
tcagccaggg agggcttcct ggaggagaag gagccagcta gacatggata ggagtgcgtt   4440
ttaggcacag caaatggcac atacaagggc caggagcaa gagagaggac aggtcctcaa    4500
caaatggcat gtgactttgt aagtgtagaa ttgctgtgag gtatgggct aggggcgtca    4560 gtagggcctt gaaggttatg gacagggccc tgggctttct tccaagggca ctggggagc    4620 catggcaagg ttgtaggtag ggtagagatg ggcgggtttg tgctatgtgc agggtggaag   4680
ggagggaagt tgacaggtca gaagatcagg aaagaggtcg gggctggaca gatggggaga   4740
gcgcagatag atttaagaga gtcctgtgag gcaaagtggg caggacctgg taacaggtgt   4800
ctggactgtg gctttggctg gctcagaagg tccccactgg cgtgtgtggt ctatgtagcc   4860
tctgggtgtg gagctgggat cttcaactgg ggacagtaca gtaaagaaca tcacagc     4917

<210> SEQ ID NO 23
<211> LENGTH: 3226
<212> TYPE: DNA
<213> ORGANISM: Homo sapiens

<400> SEQUENCE: 23
gacccggaga agatgtcttc gcggacggtg ctggccccgg gcaacgatcg gaactcggac     60
acgcatggca ccttgggcag tggccgctcc tcggacaaag gcccgtcctg gtccagccgc    120
tcactgggtg cccgttgccg gaactccatc gcctcctgtc ccgaggagca gccccacgtg    180
ggcaactacc gcctgctgag gaccattggg aagggcaact tgccaaagt caagctggct    240 cggcacatcc tcactggtcg ggaggttgcc atcaagatta tcgacaaaac ccagctgaat   300
cccagcagcc tgcagaagct gttccgagaa gtccgcatca tgaagggcct aaaccacccc    360
aacatcgtga agctctttga ggtgattgag actgagaaga cgctgtacct ggtgatggag    420
tacgcaagtg ctggagaagt gtttgactac ctcgtgtcgc atggccgcat gaaggagaag    480
gaagctcgag ccaagttccg acagattgtt tcggctgtgc actattgtca ccagaaaaat    540
attgtacaca gggacctgaa ggctgagaac ctcttgctgg atgccgaggc caacatcaag    600
attgctgact ttggcttcag caacgagttc acgctgggat cgaagctgga cacgttctgc    660
gggagccccc catatgccgc cccggagctg tttcagggca gaagtacga cgggccggag    720 gtggacatct ggagcctggg agtcatcctg tacacctcg tcagcggctc cctgccttc     780 gacgggcaca acctcaagga gctgcgggag cgagtactca gagggaagta ccgggtccct    840
ttctacatgt caacgactg tgagagcatc ctgcggagat ttttggtgct gaacccagct    900
aaacgctgta ctctcgagca aatcatgaaa gacaaatgga tcaacatcgg ctatgagggt    960
gaggagttga agccatacac agagcccgag gaggacttcg gggacaccaa gagaattgag   1020
```

```
gtgatggtgg gtatgggcta cacacgggaa gaaatcaaag agtccttgac cagccagaag    1080
tacaacgaag tgaccgccac ctacctcctg ctgggcagga agactgagga gggtggggac    1140
cggggcgccc cagggctggc cctggcacgg gtgcgggcgc ccagcgacac caccaacgga    1200
acaagttcca gcaaaggcac cagccacagc aaagggcagc ggagttcctc ttccacctac    1260
caccgccagc gcaggcatag cgatttctgt ggcccatccc ctgcacccct gcaccccaaa    1320
cgcagcccga cgagcacggg ggaggcggag ctgaaggagg agcggctgcc aggccggaag    1380
gcgagctgca gcaccgcggg gagtgggagt cgagggctgc cccctccag cccatggtc     1440 agcagcgccc acaaccccaa caaggcagag atcccagagc ggcggaagga cagcacgagc    1500 accccaaca acctccctcc tagcatgatg acccgcagaa acacctacgt ttgcacagaa     1560
cgcccggggg ctgagcgccc gtcactgttg ccaaatggga agaaaacag ctcaggcacc     1620 ccacgggtgc cccctgcctc cccctccagt cacagcctgg cacccccatc aggggagcgg    1680
agccgcctgg cacgcggttc caccatccgc agcaccttcc atggtggcca ggtccgggac    1740
cggcgggcag ggggtggggg tggtgggggt gtgcagaatg ggcccctgc ctctcccaca     1800 ctggcccatg aggctgcacc cctgcccgcc gggcggcccc gccccaccac caacctcttc    1860
accaagctga cctccaaact gacccgaagg gtcgcagacg aacctgagag aatcggggga    1920
cctgaggtca caagttgcca tctaccttgg gatcaaacgg aaaccgcccc ccggctgctc    1980
cgattcccct ggagtgtgaa gctgaccagc tcgcgccctc ctgaggccct gatggcagct    2040
ctgcgccagg ccacagcagc cgcccgctgc cgctgccgcc agccacagcc gttcctgctg    2100
gcctgcctgc acggggtgc gggcgggccc gagcccctgt cccacttcga agtggaggtc     2160
tgccagctgc cccggccagg cttgcgggga gttctcttcc gccgtgtggc gggcaccgcc    2220
ctggccttcc gcaccctcgt cacccgcatc tccaacgacc tcgagctctg agccaccacg    2280
gtcccaggcc cttatcttct ctcccttgtc gcttcacttc tacaggaggg gaaggggcca    2340 gggagggat tctcccttta tcatcacctc agtttccctg aattatattt gggggcaaag     2400 attgtccct ctgctgttct ctgggccgc tcagcacaga agaaggatga gggggctcag      2460
cggggggagc tggcaccttc ctggagcctc cagccagtcc tgtcctccct cgccctacca    2520
agagggcacc tgaggagact ttggggacag ggcaggggca gggagggaaa ctgaggaaat    2580
cttccattcc tcccaacagc tcaaaattag gccttgggca ggggcaggga gagctgctga    2640
gcctaaagac tggagaatct ggggactgg agtgggggt cagagaggca gattccttcc      2700
cctcccgtcc cctcacgctc aaaccccac ttcctgcccc aggctggcgc ggggcacttt     2760
gtacaaatcc ttgtaaatac cccacacctt cccttctgca aagtctctt gaggagctgc     2820 cgctgtcacc tacggttttt aagttattac accccgaccc tcctcctgtc agccccctca    2880
cgtgcagcct gttgcccaat aaatttagga gagtccccccc ctccccaatg ctgaccctag   2940 gatttttcctt ccctgccctc acctgcaaat gagttaaaga gaggcgtgg gaatccaggc    3000 agtggttttt cctttcggag cctcggtttt ctcatctgca gaatgggagc ggtggggtg     3060 ggaaggtaag gatggtcgtc caagaaggca ggatggaact cggcctcatc cccgaggccc    3120
cagttcctat atcgggcccc ccattcatcc actcacactc ccagccacca tgttacactg    3180
gactttaagc catttcttac tccagtagta aatttattca ataaac                   3226
```

<210> SEQ ID NO 24
<211> LENGTH: 745
<212> TYPE: PRT
<213> ORGANISM: Homo sapiens

<400> SEQUENCE: 24

```
Met Ile Arg Gly Arg Asn Ser Ala Thr Ser Ala Asp Glu Gln Pro His
1               5                   10                  15

Ile Gly Asn Tyr Arg Leu Leu Lys Thr Ile Gly Lys Gly Asn Phe Ala
            20                  25                  30

Lys Val Lys Leu Ala Arg His Ile Leu Thr Gly Lys Glu Val Ala Val
        35                  40                  45

Lys Ile Ile Asp Lys Thr Gln Leu Asn Ser Ser Leu Gln Lys Leu
    50                  55                  60

Phe Arg Glu Val Arg Ile Met Lys Val Leu Asn His Pro Asn Ile Val
65                  70                  75                  80

Lys Leu Phe Glu Val Ile Glu Thr Glu Lys Thr Leu Tyr Leu Val Met
                85                  90                  95

Glu Tyr Ala Ser Gly Gly Glu Val Phe Asp Tyr Leu Val Ala His Gly
            100                 105                 110

Arg Met Lys Glu Lys Glu Ala Arg Ala Lys Phe Arg Gln Ile Val Ser
        115                 120                 125

Ala Val Gln Tyr Cys His Gln Lys Phe Ile Val His Arg Asp Leu Lys
130                 135                 140

Ala Glu Asn Leu Leu Leu Asp Ala Asp Met Asn Ile Lys Ile Ala Asp
145                 150                 155                 160

Phe Gly Phe Ser Asn Glu Phe Thr Phe Gly Asn Lys Leu Asp Thr Phe
                165                 170                 175

Cys Gly Ser Pro Pro Tyr Ala Ala Pro Glu Leu Phe Gln Gly Lys Lys
            180                 185                 190

Tyr Asp Gly Pro Glu Val Asp Val Trp Ser Leu Gly Val Ile Leu Tyr
        195                 200                 205

Thr Leu Val Ser Gly Ser Leu Pro Phe Asp Gly Gln Asn Leu Lys Glu
    210                 215                 220

Leu Arg Glu Arg Val Leu Arg Gly Lys Tyr Arg Ile Pro Phe Tyr Met
225                 230                 235                 240

Ser Thr Asp Cys Glu Asn Leu Leu Lys Lys Phe Leu Ile Leu Asn Pro
                245                 250                 255

Ser Lys Arg Gly Thr Leu Glu Gln Ile Met Lys Asp Arg Trp Met Asn
            260                 265                 270

Val Gly His Glu Asp Asp Glu Leu Lys Pro Tyr Val Glu Pro Leu Pro
        275                 280                 285

Asp Tyr Lys Asp Pro Arg Arg Thr Glu Leu Met Val Ser Met Gly Tyr
    290                 295                 300

Thr Arg Glu Glu Ile Gln Asp Ser Leu Val Gly Gln Arg Tyr Asn Glu
305                 310                 315                 320

Val Met Ala Thr Tyr Leu Leu Leu Gly Tyr Lys Ser Ser Glu Leu Glu
                325                 330                 335

Gly Asp Thr Ile Thr Leu Lys Pro Arg Pro Ser Ala Asp Leu Thr Asn
            340                 345                 350

Ser Ser Ala Gln Phe Pro Ser His Lys Val Arg Ser Val Ser Ala
        355                 360                 365

Asn Pro Lys Gln Arg Arg Phe Ser Asp Gln Ala Gly Pro Ala Ile Pro
370                 375                 380

Thr Ser Asn Ser Tyr Ser Lys Lys Thr Gln Ser Asn Asn Ala Glu Asn
385                 390                 395                 400

Lys Arg Pro Glu Glu Asp Arg Glu Ser Gly Arg Lys Ala Ser Ser Thr
                405                 410                 415
```

```
Ala Lys Val Pro Ala Ser Pro Leu Pro Gly Leu Glu Arg Lys Lys Thr
            420                 425                 430

Thr Pro Thr Pro Ser Thr Asn Ser Val Leu Ser Thr Ser Thr Asn Arg
            435                 440                 445

Ser Arg Asn Ser Pro Leu Leu Glu Arg Ala Ser Leu Gly Gln Ala Ser
450                 455                 460

Ile Gln Asn Gly Lys Asp Ser Leu Thr Met Pro Gly Ser Arg Ala Ser
465                 470                 475                 480

Thr Ala Ser Ala Ser Ala Ala Val Ser Ala Ala Arg Pro Arg Gln His
            485                 490                 495

Gln Lys Ser Met Ser Ala Ser Val His Pro Asn Lys Ala Ser Gly Leu
            500                 505                 510

Pro Pro Thr Glu Ser Asn Cys Glu Val Pro Arg Pro Ser Thr Ala Pro
            515                 520                 525

Gln Arg Val Pro Val Ala Ser Pro Ser Ala His Asn Ile Ser Ser Ser
530                 535                 540

Gly Gly Ala Pro Asp Arg Thr Asn Phe Pro Arg Gly Val Ser Ser Arg
545                 550                 555                 560

Ser Thr Phe His Ala Gly Gln Leu Arg Gln Val Arg Asp Gln Gln Asn
            565                 570                 575

Leu Pro Tyr Gly Val Thr Pro Ala Ser Pro Ser Gly His Ser Gln Gly
            580                 585                 590

Arg Arg Gly Ala Ser Gly Ser Ile Phe Ser Lys Phe Thr Ser Lys Phe
            595                 600                 605

Val Arg Arg Asn Leu Asn Glu Pro Glu Ser Lys Asp Arg Val Glu Thr
610                 615                 620

Leu Arg Pro His Val Val Gly Ser Gly Asn Asp Lys Glu Lys Glu
625                 630                 635                 640

Glu Phe Arg Glu Ala Lys Pro Arg Ser Leu Arg Phe Thr Trp Ser Met
            645                 650                 655

Lys Thr Thr Ser Ser Met Glu Pro Asn Glu Met Met Arg Glu Ile Arg
            660                 665                 670

Lys Val Leu Asp Ala Asn Ser Cys Gln Ser Glu Leu His Glu Lys Tyr
            675                 680                 685

Met Leu Leu Cys Met His Gly Thr Pro Gly His Glu Asp Phe Val Gln
            690                 695                 700

Trp Glu Met Glu Val Cys Lys Leu Pro Arg Leu Ser Leu Asn Gly Val
705                 710                 715                 720

Arg Phe Lys Arg Ile Ser Gly Thr Ser Met Ala Phe Lys Asn Ile Ala
            725                 730                 735

Ser Lys Ile Ala Asn Glu Leu Lys Leu
            740                 745

<210> SEQ ID NO 25
<211> LENGTH: 795
<212> TYPE: PRT
<213> ORGANISM: Homo sapiens

<400> SEQUENCE: 25

Met Ser Ala Arg Thr Pro Leu Pro Thr Val Asn Glu Arg Asp Thr Val
1               5                   10                  15

Asn His Thr Thr Val Asp Gly Tyr Thr Glu Pro His Ile Gln Pro Thr
            20                  25                  30

Lys Ser Ser Ser Arg Gln Asn Ile Pro Arg Cys Arg Asn Ser Ile Thr
        35                  40                  45
```

```
Ser Ala Thr Asp Glu Gln Pro His Ile Gly Asn Tyr Arg Leu Gln Lys
    50                  55                  60

Thr Ile Gly Lys Gly Asn Phe Ala Lys Val Lys Leu Ala Arg His Val
65                  70                  75                  80

Leu Thr Gly Arg Glu Val Ala Val Lys Ile Ile Asp Lys Thr Gln Leu
                85                  90                  95

Asn Pro Thr Ser Leu Gln Lys Leu Phe Arg Glu Val Arg Ile Met Lys
                100                 105                 110

Ile Leu Asn His Pro Asn Ile Val Lys Leu Phe Glu Val Ile Glu Thr
            115                 120                 125

Glu Lys Thr Leu Tyr Leu Val Met Glu Tyr Ala Ser Gly Gly Glu Val
        130                 135                 140

Phe Asp Tyr Leu Val Ala His Gly Arg Met Lys Glu Lys Glu Ala Arg
145                 150                 155                 160

Ala Lys Phe Arg Gln Ile Val Ser Ala Val Gln Tyr Cys His Gln Lys
                165                 170                 175

Tyr Ile Val His Arg Asp Leu Lys Ala Glu Asn Leu Leu Leu Asp Gly
            180                 185                 190

Asp Met Asn Ile Lys Ile Ala Asp Phe Gly Phe Ser Asn Glu Phe Thr
        195                 200                 205

Val Gly Asn Lys Leu Asp Thr Phe Cys Gly Ser Pro Pro Tyr Ala Ala
    210                 215                 220

Pro Glu Leu Phe Gln Gly Lys Lys Tyr Asp Gly Pro Glu Val Asp Val
225                 230                 235                 240

Trp Ser Leu Gly Val Ile Leu Tyr Thr Leu Val Ser Gly Ser Leu Pro
                245                 250                 255

Phe Asp Gly Gln Asn Leu Lys Glu Leu Arg Glu Arg Val Leu Arg Gly
                260                 265                 270

Lys Tyr Arg Ile Pro Phe Tyr Met Ser Thr Asp Cys Glu Asn Leu Leu
        275                 280                 285

Lys Lys Leu Leu Val Leu Asn Pro Ile Lys Arg Gly Ser Leu Glu Gln
    290                 295                 300

Ile Met Lys Asp Arg Trp Met Asn Val Gly His Glu Glu Glu Glu Leu
305                 310                 315                 320

Lys Pro Tyr Thr Glu Pro Asp Pro Asp Phe Asn Asp Thr Lys Arg Ile
                325                 330                 335

Asp Ile Met Val Thr Met Gly Phe Ala Arg Asp Glu Ile Asn Asp Ala
            340                 345                 350

Leu Ile Asn Gln Lys Tyr Asp Glu Val Met Ala Thr Tyr Ile Leu Leu
        355                 360                 365

Gly Arg Lys Pro Pro Glu Phe Glu Gly Gly Glu Ser Leu Ser Ser Gly
    370                 375                 380

Asn Leu Cys Gln Arg Ser Arg Pro Ser Ser Asp Leu Asn Asn Ser Thr
385                 390                 395                 400

Leu Gln Ser Pro Ala His Leu Lys Val Gln Arg Ser Ile Ser Ala Asn
                405                 410                 415

Gln Lys Gln Arg Arg Phe Ser Asp His Ala Gly Pro Ser Ile Pro Pro
            420                 425                 430

Ala Val Ser Tyr Thr Lys Arg Pro Gln Ala Asn Ser Val Glu Ser Glu
        435                 440                 445

Gln Lys Glu Glu Trp Asp Lys Asp Val Ala Arg Lys Leu Gly Ser Thr
    450                 455                 460

Thr Val Gly Ser Lys Ser Glu Met Thr Ala Ser Pro Leu Val Gly Pro
```

```
                465                 470                 475                 480
Glu Arg Lys Lys Ser Ser Thr Ile Pro Ser Asn Asn Val Tyr Ser Gly
                    485                 490                 495
Gly Ser Met Ala Arg Arg Asn Thr Tyr Val Cys Glu Arg Thr Thr Asp
                500                 505                 510
Arg Tyr Val Ala Leu Gln Asn Gly Lys Asp Ser Ser Leu Thr Glu Met
                515                 520                 525
Ser Val Ser Ser Ile Ser Ser Ala Gly Ser Ser Val Ala Ser Ala Val
                530                 535                 540
Pro Ser Ala Arg Pro Arg His Gln Lys Ser Met Ser Thr Ser Gly His
545                 550                 555                 560
Pro Ile Lys Val Thr Leu Pro Thr Ile Lys Asp Gly Ser Glu Ala Tyr
                    565                 570                 575
Arg Pro Gly Thr Thr Gln Arg Val Pro Ala Ala Ser Pro Ser Ala His
                580                 585                 590
Ser Ile Ser Thr Ala Thr Pro Asp Arg Thr Arg Phe Pro Arg Gly Ser
                595                 600                 605
Ser Ser Arg Ser Thr Phe His Gly Glu Gln Leu Arg Glu Arg Arg Ser
                610                 615                 620
Val Ala Tyr Asn Gly Pro Pro Ala Ser Pro Ser His Glu Thr Gly Ala
625                 630                 635                 640
Phe Ala His Ala Arg Arg Gly Thr Ser Thr Gly Ile Ile Ser Lys Ile
                    645                 650                 655
Thr Ser Lys Phe Val Arg Arg Asp Pro Ser Glu Gly Glu Ala Ser Gly
                660                 665                 670
Arg Thr Asp Thr Ser Arg Ser Thr Ser Gly Glu Pro Lys Glu Arg Asp
                675                 680                 685
Lys Glu Glu Gly Lys Asp Ser Lys Pro Arg Ser Leu Arg Phe Thr Trp
                690                 695                 700
Ser Met Lys Thr Thr Ser Ser Met Asp Pro Asn Asp Met Met Arg Glu
705                 710                 715                 720
Ile Arg Lys Val Leu Asp Ala Asn Asn Cys Asp Tyr Glu Gln Lys Glu
                    725                 730                 735
Arg Phe Leu Leu Phe Cys Val His Gly Asp Ala Arg Gln Asp Ser Leu
                740                 745                 750
Val Gln Trp Glu Met Glu Val Cys Lys Leu Pro Arg Leu Ser Leu Asn
                755                 760                 765
Gly Val Arg Phe Lys Arg Ile Ser Gly Thr Ser Ile Ala Phe Lys Asn
                770                 775                 780
Ile Ala Ser Lys Ile Ala Asn Glu Leu Lys Leu
785                 790                 795

<210> SEQ ID NO 26
<211> LENGTH: 729
<212> TYPE: PRT
<213> ORGANISM: Homo sapiens

<400> SEQUENCE: 26

Met Ser Thr Arg Thr Pro Leu Pro Thr Val Asn Glu Arg Asp Thr Glu
1               5                   10                  15
Asn His Thr Ser His Gly Asp Gly Arg Gln Glu Val Thr Ser Arg Thr
                20                  25                  30
Ser Arg Ser Gly Ala Arg Cys Arg Asn Ser Ile Ala Ser Cys Ala Asp
                35                  40                  45
Glu Gln Pro His Ile Gly Asn Tyr Arg Leu Leu Lys Thr Ile Gly Lys
```

```
                50                  55                  60
Gly Asn Phe Ala Lys Val Lys Leu Ala Arg His Ile Leu Thr Gly Arg
 65                  70                  75                  80

Glu Val Ala Ile Lys Ile Ile Asp Lys Thr Gln Leu Asn Pro Thr Ser
                 85                  90                  95

Leu Gln Lys Leu Phe Arg Glu Val Arg Ile Met Lys Ile Leu Asn His
                100                 105                 110

Pro Asn Ile Val Lys Leu Phe Glu Val Ile Glu Thr Glu Lys Thr Leu
                115                 120                 125

Tyr Leu Ile Met Glu Tyr Ala Ser Gly Gly Glu Val Phe Asp Tyr Leu
                130                 135                 140

Val Ala His Gly Arg Met Lys Glu Lys Glu Ala Arg Ser Lys Phe Arg
145                 150                 155                 160

Gln Ile Val Ser Ala Val Gln Tyr Cys His Gln Lys Arg Ile Val His
                165                 170                 175

Arg Asp Leu Lys Ala Glu Asn Leu Leu Leu Asp Ala Asp Met Asn Ile
                180                 185                 190

Lys Ile Ala Asp Phe Gly Phe Ser Asn Glu Phe Thr Val Gly Gly Lys
                195                 200                 205

Leu Asp Thr Phe Cys Gly Ser Pro Pro Tyr Ala Ala Pro Glu Leu Phe
210                 215                 220

Gln Gly Lys Lys Tyr Asp Gly Pro Glu Val Asp Val Trp Ser Leu Gly
225                 230                 235                 240

Val Ile Leu Tyr Thr Leu Val Ser Gly Ser Leu Pro Phe Asp Gly Gln
                245                 250                 255

Asn Leu Lys Glu Leu Arg Glu Arg Val Leu Arg Gly Lys Tyr Arg Ile
                260                 265                 270

Pro Phe Tyr Met Ser Thr Asp Cys Glu Asn Leu Leu Lys Arg Phe Leu
                275                 280                 285

Val Leu Asn Pro Ile Lys Arg Gly Thr Leu Glu Gln Ile Met Lys Asp
                290                 295                 300

Arg Trp Ile Asn Ala Gly His Glu Glu Asp Glu Leu Lys Pro Phe Val
305                 310                 315                 320

Glu Pro Glu Leu Asp Ile Ser Asp Gln Lys Arg Ile Asp Ile Met Val
                325                 330                 335

Gly Met Gly Tyr Ser Gln Glu Glu Ile Gln Glu Ser Leu Ser Lys Met
                340                 345                 350

Lys Tyr Asp Glu Ile Thr Ala Thr Tyr Leu Leu Leu Gly Arg Lys Ser
                355                 360                 365

Ser Glu Leu Asp Ala Ser Asp Ser Ser Ser Ser Asn Leu Ser Leu
                370                 375                 380

Ala Lys Val Arg Pro Ser Ser Asp Leu Asn Asn Ser Thr Gly Gln Ser
385                 390                 395                 400

Pro His His Lys Val Gln Arg Ser Val Ser Ser Gln Lys Gln Arg
                405                 410                 415

Arg Tyr Ser Asp His Ala Gly Pro Ala Ile Pro Ser Val Val Ala Tyr
                420                 425                 430

Pro Lys Arg Ser Gln Thr Ser Thr Ala Asp Gly Asp Leu Lys Glu Asp
                435                 440                 445

Gly Ile Ser Ser Arg Lys Ser Ser Gly Ser Ala Val Gly Gly Lys Gly
                450                 455                 460

Ile Ala Pro Ala Ser Pro Met Leu Gly Asn Ala Ser Asn Pro Asn Lys
465                 470                 475                 480
```

```
Ala Asp Ile Pro Glu Arg Lys Lys Ser Ser Thr Val Pro Ser Ser Asn
                485                 490                 495

Thr Ala Ser Gly Gly Met Thr Arg Arg Asn Thr Tyr Val Cys Ser Glu
            500                 505                 510

Arg Thr Thr Ala Asp Arg His Ser Val Ile Gln Asn Gly Lys Glu Asn
        515                 520                 525

Ser Thr Ile Pro Asp Gln Arg Thr Pro Val Ala Ser Thr His Ser Ile
    530                 535                 540

Ser Ser Ala Ala Thr Pro Asp Arg Ile Arg Phe Pro Arg Gly Thr Ala
545                 550                 555                 560

Ser Arg Ser Thr Phe His Gly Gln Pro Arg Glu Arg Thr Ala Thr
                565                 570                 575

Tyr Asn Gly Pro Pro Ala Ser Pro Ser Leu Ser His Glu Ala Thr Pro
            580                 585                 590

Leu Ser Gln Thr Arg Ser Arg Gly Ser Thr Asn Leu Phe Ser Lys Leu
        595                 600                 605

Thr Ser Lys Leu Thr Arg Ser Arg Asn Val Ser Ala Glu Gln Lys Asp
    610                 615                 620

Glu Asn Lys Glu Ala Lys Pro Arg Ser Leu Arg Phe Thr Trp Ser Met
625                 630                 635                 640

Lys Thr Thr Ser Ser Met Asp Pro Gly Asp Met Met Arg Glu Ile Arg
                645                 650                 655

Lys Val Leu Asp Ala Asn Asn Cys Asp Tyr Glu Gln Arg Glu Arg Phe
            660                 665                 670

Leu Leu Phe Cys Val His Gly Asp Gly His Ala Glu Asn Leu Val Gln
        675                 680                 685

Trp Glu Met Glu Val Cys Lys Leu Pro Arg Leu Ser Leu Asn Gly Val
    690                 695                 700

Arg Phe Lys Arg Ile Ser Gly Thr Ser Ile Ala Phe Lys Asn Ile Ala
705                 710                 715                 720

Ser Lys Ile Ala Asn Glu Leu Lys Leu
                725

<210> SEQ ID NO 27
<211> LENGTH: 713
<212> TYPE: PRT
<213> ORGANISM: Homo sapiens

<400> SEQUENCE: 27

Met Ser Thr Arg Thr Pro Leu Pro Thr Val Asn Glu Arg Asp Thr Glu
1               5                   10                  15

Asn His Thr Ser His Gly Asp Gly Arg Gln Glu Val Thr Ser Arg Thr
            20                  25                  30

Ser Arg Ser Gly Ala Arg Cys Arg Asn Ser Ile Ala Ser Cys Ala Asp
        35                  40                  45

Glu Gln Pro His Ile Gly Asn Tyr Arg Leu Leu Lys Thr Ile Gly Lys
    50                  55                  60

Gly Asn Phe Ala Lys Val Lys Leu Ala Arg His Ile Leu Thr Gly Arg
65                  70                  75                  80

Glu Val Ala Ile Lys Ile Ile Asp Lys Thr Gln Leu Asn Pro Thr Ser
                85                  90                  95

Leu Gln Lys Leu Phe Arg Glu Val Arg Ile Met Lys Ile Leu Asn His
            100                 105                 110

Pro Asn Ile Val Lys Leu Phe Glu Val Ile Glu Thr Gln Lys Thr Leu
        115                 120                 125
```

```
Tyr Leu Ile Met Glu Tyr Ala Ser Gly Gly Lys Val Phe Asp Tyr Leu
            130                 135                 140

Val Ala His Gly Arg Met Lys Glu Lys Glu Ala Arg Ser Lys Phe Arg
145                 150                 155                 160

Gln Ile Val Ser Ala Val Gln Tyr Cys His Gln Lys Arg Ile Val His
                165                 170                 175

Arg Asp Leu Lys Ala Glu Asn Leu Leu Leu Asp Ala Asp Met Asn Ile
            180                 185                 190

Lys Ile Ala Asp Phe Gly Phe Ser Asn Glu Phe Thr Val Gly Gly Lys
            195                 200                 205

Leu Asp Thr Phe Cys Gly Ser Pro Pro Tyr Ala Ala Pro Glu Leu Phe
210                 215                 220

Gln Gly Lys Lys Tyr Asp Gly Pro Glu Val Asp Val Trp Ser Leu Gly
225                 230                 235                 240

Val Ile Leu Tyr Thr Leu Val Ser Gly Ser Leu Pro Phe Asp Gly Gln
                245                 250                 255

Asn Leu Lys Glu Leu Arg Glu Arg Val Leu Arg Gly Lys Tyr Arg Ile
            260                 265                 270

Pro Phe Tyr Met Ser Thr Asp Cys Glu Asn Leu Leu Lys Arg Phe Leu
            275                 280                 285

Val Leu Asn Pro Ile Lys Arg Gly Thr Leu Glu Gln Ile Met Lys Asp
290                 295                 300

Arg Trp Ile Asn Ala Gly His Glu Glu Asp Glu Leu Lys Pro Phe Val
305                 310                 315                 320

Glu Pro Glu Leu Asp Ile Ser Asp Gln Lys Arg Ile Asp Ile Met Val
                325                 330                 335

Gly Met Gly Tyr Ser Gln Glu Glu Ile Gln Glu Ser Leu Ser Lys Met
            340                 345                 350

Lys Tyr Asp Glu Ile Thr Ala Thr Tyr Leu Leu Leu Gly Arg Lys Ser
            355                 360                 365

Ser Glu Val Arg Pro Ser Ser Asp Leu Asn Asn Ser Thr Gly Gln Ser
370                 375                 380

Pro His His Lys Val Gln Arg Ser Val Ser Ser Ser Gln Lys Gln Arg
385                 390                 395                 400

Arg Tyr Ser Asp His Ala Gly Pro Gly Ile Pro Ser Val Val Ala Tyr
                405                 410                 415

Pro Lys Arg Ser Gln Thr Ser Thr Ala Asp Ser Asp Leu Lys Glu Asp
            420                 425                 430

Gly Ile Ser Ser Arg Lys Ser Thr Gly Ser Ala Val Gly Gly Lys Gly
            435                 440                 445

Ile Ala Pro Ala Ser Pro Met Leu Gly Asn Ala Ser Asn Pro Asn Lys
450                 455                 460

Ala Asp Ile Pro Glu Arg Lys Lys Ser Ser Thr Val Pro Ser Ser Asn
465                 470                 475                 480

Thr Ala Ser Gly Gly Met Thr Arg Arg Asn Thr Tyr Val Cys Ser Glu
                485                 490                 495

Arg Thr Thr Asp Asp Arg His Ser Val Ile Gln Asn Gly Lys Glu Asn
            500                 505                 510

Ser Thr Ile Pro Asp Gln Arg Thr Pro Val Ala Ser Thr His Ser Ile
            515                 520                 525

Ser Ser Ala Ala Thr Pro Asp Arg Ile Arg Phe Pro Arg Gly Thr Ala
530                 535                 540

Ser Arg Ser Thr Phe His Gly Gln Pro Arg Glu Arg Arg Thr Ala Thr
545                 550                 555                 560
```

Tyr Asn Gly Pro Pro Ala Ser Pro Ser Leu Ser His Glu Ala Thr Pro
            565                 570                 575

Leu Ser Gln Thr Arg Ser Arg Gly Ser Thr Thr Leu Phe Ser Lys Leu
            580                 585                 590

Thr Ser Lys Leu Thr Arg Ser Arg Asn Val Ser Ala Lys Gln Lys Asp
            595                 600                 605

Glu Asn Lys Glu Ala Lys Pro Arg Ser Leu Arg Phe Thr Trp Ser Met
            610                 615                 620

Lys Thr Thr Ser Ser Met Asp Pro Gly Asp Met Met Arg Glu Ile Arg
625                 630                 635                 640

Lys Val Leu Asp Ala Asn Asn Cys Asp Tyr Glu Gln Arg Glu Arg Phe
                645                 650                 655

Leu Leu Phe Cys Val His Gly Asp Gly His Ala Glu Asn Leu Val Gln
                660                 665                 670

Trp Glu Met Glu Val Cys Lys Leu Pro Arg Leu Ser Leu Asn Gly Val
            675                 680                 685

Arg Phe Lys Arg Ile Ser Gly Thr Ser Ile Ala Phe Lys Asn Ile Ala
            690                 695                 700

Ser Lys Ile Ala Asn Glu Leu Lys Leu
705                 710

<210> SEQ ID NO 28
<211> LENGTH: 688
<212> TYPE: PRT
<213> ORGANISM: Homo sapiens

<400> SEQUENCE: 28

Met Ser Ser Arg Thr Val Leu Ala Pro Gly Asn Asp Arg Asn Ser Asp
1               5                   10                  15

Thr His Gly Thr Leu Gly Ser Gly Arg Ser Ser Asp Lys Gly Pro Ser
            20                  25                  30

Trp Ser Ser Arg Ser Leu Gly Ala Arg Cys Arg Asn Ser Ile Ala Ser
            35                  40                  45

Cys Pro Glu Glu Gln Pro His Val Gly Asn Tyr Arg Leu Leu Arg Thr
        50                  55                  60

Ile Gly Lys Gly Asn Ser Ala Lys Val Lys Leu Ala Arg His Ile Leu
65                  70                  75                  80

Thr Gly Arg Glu Val Ala Ile Lys Ile Ile Asp Lys Thr Gln Leu Asn
                85                  90                  95

Pro Ser Ser Leu Gln Lys Leu Phe Arg Glu Val Arg Ile Met Lys Gly
            100                 105                 110

Leu Asn His Pro Asn Ile Val Lys Leu Phe Glu Val Ile Glu Thr Glu
            115                 120                 125

Lys Thr Leu Tyr Leu Val Met Glu Tyr Ala Ser Ala Gly Glu Val Phe
        130                 135                 140

Asp Tyr Leu Val Ser His Gly Arg Met Lys Glu Lys Glu Ala Arg Ala
145                 150                 155                 160

Lys Phe Arg Gln Ile Val Ser Ala Val His Tyr Cys His Gln Lys Asn
                165                 170                 175

Ile Val His Arg Asp Leu Lys Ala Glu Asn Leu Leu Leu Asp Ala Glu
            180                 185                 190

Ala Asn Ile Lys Ile Ala Asp Phe Gly Phe Ser Asn Glu Phe Thr Leu
        195                 200                 205

Gly Ser Lys Leu Asp Thr Phe Cys Gly Ser Pro Pro Tyr Ala Ala Pro
    210                 215                 220

```
Glu Leu Phe Gln Gly Lys Lys Tyr Asp Gly Pro Glu Val Asp Ile Trp
225                 230                 235                 240

Ser Leu Gly Val Ile Leu Tyr Thr Leu Val Ser Gly Ser Leu Pro Phe
                245                 250                 255

Asp Gly His Asn Leu Lys Glu Leu Arg Glu Arg Val Leu Arg Gly Lys
            260                 265                 270

Tyr Arg Val Pro Phe Tyr Met Ser Thr Asp Cys Glu Ser Ile Leu Arg
        275                 280                 285

Arg Phe Leu Val Leu Asn Pro Ala Lys Arg Cys Thr Leu Glu Gln Ile
    290                 295                 300

Met Lys Asp Lys Trp Ile Asn Ile Gly Tyr Glu Gly Glu Glu Leu Lys
305                 310                 315                 320

Pro Tyr Thr Glu Pro Glu Glu Asp Phe Gly Asp Thr Lys Arg Ile Glu
                325                 330                 335

Val Met Val Gly Met Gly Tyr Thr Arg Glu Glu Ile Lys Glu Ser Leu
            340                 345                 350

Thr Ser Gln Lys Tyr Asn Glu Val Thr Ala Thr Tyr Leu Leu Leu Gly
        355                 360                 365

Arg Lys Thr Glu Glu Gly Gly Asp Arg Gly Ala Pro Gly Leu Ala Leu
    370                 375                 380

Ala Arg Val Arg Ala Pro Ser Asp Thr Thr Asn Gly Thr Ser Ser Ser
385                 390                 395                 400

Lys Gly Thr Ser His Ser Lys Gly Gln Arg Ser Ser Ser Thr Tyr
                405                 410                 415

His Arg Gln Arg Arg His Ser Asp Phe Cys Gly Pro Ser Pro Ala Pro
            420                 425                 430

Leu His Pro Lys Arg Ser Pro Thr Ser Thr Gly Glu Ala Glu Leu Lys
        435                 440                 445

Glu Glu Arg Leu Pro Gly Arg Lys Ala Ser Cys Ser Thr Ala Gly Ser
    450                 455                 460

Gly Ser Arg Gly Leu Pro Pro Ser Ser Pro Met Val Ser Ser Ala His
465                 470                 475                 480

Asn Pro Asn Lys Ala Glu Ile Pro Glu Arg Arg Lys Asp Ser Thr Ser
                485                 490                 495

Thr Pro Asn Asn Leu Pro Pro Ser Met Met Thr Arg Arg Asn Thr Tyr
            500                 505                 510

Val Cys Thr Glu Arg Pro Gly Ala Glu Arg Pro Ser Leu Leu Pro Asn
        515                 520                 525

Gly Lys Glu Asn Ser Ser Gly Thr Pro Arg Val Pro Pro Ala Ser Pro
    530                 535                 540

Ser Ser His Ser Leu Ala Pro Pro Ser Gly Glu Arg Ser Arg Leu Ala
545                 550                 555                 560

Arg Gly Ser Thr Ile Arg Ser Thr Phe His Gly Gly Gln Val Arg Asp
                565                 570                 575

Arg Arg Ala Gly Gly Gly Gly Gly Val Gln Asn Gly Pro Pro
            580                 585                 590

Ala Ser Pro Thr Leu Ala His Glu Ala Ala Pro Leu Pro Ala Gly Arg
        595                 600                 605

Pro Arg Pro Thr Thr Asn Leu Phe Thr Lys Leu Thr Ser Lys Leu Thr
    610                 615                 620

Arg Arg Val Thr Leu Asp Pro Ser Lys Arg Gln Asn Ser Asn Arg Cys
625                 630                 635                 640

Val Ser Gly Ala Ser Leu Pro Gln Gly Ser Lys Ile Arg Ser Gln Thr
```

```
                      645                 650                 655
Asn Leu Arg Glu Ser Gly Asp Leu Arg Ser Gln Val Ala Ile Tyr Leu
                660                 665                 670

Gly Ile Lys Arg Lys Pro Pro Gly Cys Ser Asp Ser Pro Gly Val
            675                 680                 685

<210> SEQ ID NO 29
<211> LENGTH: 688
<212> TYPE: PRT
<213> ORGANISM: Homo sapiens

<400> SEQUENCE: 29

Met Ser Ser Arg Thr Val Leu Ala Pro Gly Asn Asp Arg Asn Ser Asp
1               5                   10                  15

Thr His Gly Thr Leu Gly Ser Gly Arg Ser Ser Asp Lys Gly Pro Ser
            20                  25                  30

Trp Ser Arg Ser Leu Gly Ala Arg Cys Arg Asn Ser Ile Ala Ser
        35                  40                  45

Cys Pro Glu Glu Gln Pro His Val Gly Asn Tyr Arg Leu Leu Arg Thr
    50                  55                  60

Ile Gly Lys Gly Asn Ser Ala Lys Val Lys Leu Ala Arg His Ile Leu
65                  70                  75                  80

Thr Gly Arg Glu Val Ala Ile Lys Ile Ile Asp Lys Thr Gln Leu Asn
                85                  90                  95

Pro Ser Ser Leu Gln Lys Leu Phe Arg Glu Val Arg Ile Met Lys Gly
            100                 105                 110

Leu Asn His Pro Asn Ile Val Lys Leu Phe Glu Val Ile Glu Thr Glu
        115                 120                 125

Lys Thr Leu Tyr Leu Val Met Glu Tyr Ala Ser Ala Gly Glu Val Phe
    130                 135                 140

Asp Tyr Leu Val Ser His Gly Arg Met Lys Glu Lys Glu Ala Arg Ala
145                 150                 155                 160

Lys Phe Arg Gln Ile Val Ser Ala Val His Tyr Cys His Gln Lys Asn
                165                 170                 175

Ile Val His Arg Asp Leu Lys Ala Glu Asn Leu Leu Leu Asp Ala Glu
            180                 185                 190

Ala Asn Ile Lys Ile Ala Asp Phe Gly Phe Ser Asn Glu Phe Thr Leu
        195                 200                 205

Gly Ser Lys Leu Asp Thr Phe Cys Gly Ser Pro Pro Tyr Ala Ala Pro
    210                 215                 220

Glu Leu Phe Gln Gly Lys Lys Tyr Asp Gly Pro Glu Val Asp Ile Trp
225                 230                 235                 240

Ser Leu Gly Val Ile Leu Tyr Thr Leu Val Ser Gly Ser Leu Pro Phe
                245                 250                 255

Asp Gly His Asn Leu Lys Glu Leu Arg Glu Arg Val Leu Arg Gly Lys
            260                 265                 270

Tyr Arg Val Pro Phe Tyr Met Ser Thr Asp Cys Glu Ser Ile Leu Arg
        275                 280                 285

Arg Phe Leu Val Leu Asn Pro Ala Lys Arg Cys Thr Leu Glu Gln Ile
    290                 295                 300

Met Lys Asp Lys Trp Ile Asn Ile Gly Tyr Glu Gly Glu Glu Leu Lys
305                 310                 315                 320

Pro Tyr Thr Glu Pro Glu Glu Asp Phe Gly Asp Thr Lys Arg Ile Glu
                325                 330                 335

Val Met Val Gly Met Gly Tyr Thr Arg Glu Glu Ile Lys Glu Ser Leu
```

-continued

```
                         340                 345                 350
Thr Ser Gln Lys Tyr Asn Glu Val Thr Ala Thr Tyr Leu Leu Leu Gly
            355                 360                 365
Arg Lys Thr Glu Glu Gly Gly Asp Arg Gly Ala Pro Gly Leu Ala Leu
            370                 375                 380
Ala Arg Val Arg Ala Pro Ser Asp Thr Thr Asn Gly Thr Ser Ser Ser
385                 390                 395                 400
Lys Gly Thr Ser His Ser Lys Gly Gln Arg Ser Ser Ser Thr Tyr
            405                 410                 415
His Arg Gln Arg Arg His Ser Asp Phe Cys Gly Pro Ser Pro Ala Pro
            420                 425                 430
Leu His Pro Lys Arg Ser Pro Thr Ser Thr Gly Glu Ala Glu Leu Lys
            435                 440                 445
Glu Glu Arg Leu Pro Gly Arg Lys Ala Ser Cys Ser Thr Ala Gly Ser
            450                 455                 460
Gly Ser Arg Gly Leu Pro Pro Ser Ser Pro Met Val Ser Ser Ala His
465                 470                 475                 480
Asn Pro Asn Lys Ala Glu Ile Pro Glu Arg Arg Lys Asp Ser Thr Ser
            485                 490                 495
Thr Pro Asn Asn Leu Pro Pro Ser Met Met Thr Arg Arg Asn Thr Tyr
            500                 505                 510
Val Cys Thr Glu Arg Pro Gly Ala Glu Arg Pro Ser Leu Leu Pro Asn
            515                 520                 525
Gly Lys Glu Asn Ser Ser Gly Thr Pro Arg Val Pro Pro Ala Ser Pro
            530                 535                 540
Ser Ser His Ser Leu Ala Pro Pro Ser Gly Glu Arg Ser Arg Leu Ala
545                 550                 555                 560
Arg Gly Ser Thr Ile Arg Ser Thr Phe His Gly Gly Gln Val Arg Asp
            565                 570                 575
Arg Arg Ala Gly Gly Gly Gly Gly Val Gln Asn Gly Pro Pro
            580                 585                 590
Ala Ser Pro Thr Leu Ala His Glu Ala Ala Pro Leu Pro Ala Gly Arg
            595                 600                 605
Pro Arg Pro Thr Thr Asn Leu Phe Thr Lys Leu Thr Ser Lys Leu Thr
            610                 615                 620
Arg Arg Val Thr Leu Asp Pro Ser Lys Arg Gln Asn Ser Asn Arg Cys
625                 630                 635                 640
Val Ser Gly Ala Ser Leu Pro Gln Gly Ser Lys Ile Arg Ser Gln Thr
            645                 650                 655
Asn Leu Arg Glu Ser Gly Asp Leu Arg Ser Gln Val Ala Ile Tyr Leu
            660                 665                 670
Gly Ile Lys Arg Lys Pro Pro Pro Gly Cys Ser Asp Ser Pro Gly Val
            675                 680                 685
```

MARKS AS MODIFIERS OF THE P53 PATHWAY AND METHODS OF USE

REFERENCE TO RELATED APPLICATIONS

This application is a continuation application of U.S. application Ser. No. 11/627,976, filed Jan. 28, 2007 (abandoned), which is a continuation of U.S. application Ser. No. of 10/161,565 filed Aug. 2, 2002 (abandoned), which claims priority to U.S. provisional patent application 60/296,076, filed Jun. 5, 2001, U.S. provisional patent application 60/328,605, filed Oct. 10, 2001, and U.S. provisional patent application 60/357,253, filed Feb. 15, 2002. The contents of the prior applications are hereby incorporated by reference in their entireties.

BACKGROUND OF THE INVENTION

The p53 gene is mutated in over 50 different types of human cancers, including familial and spontaneous cancers, and is believed to be the most commonly mutated gene in human cancer (Zambetti and Levine, FASEB (1993) 7:855-865; Hollstein, et al., Nucleic Acids Res. (1994) 22:3551-3555). Greater than 90% of mutations in the p53 gene are missense mutations that alter a single amino acid that inactivates p53 function. Aberrant forms of human p53 are associated with poor prognosis, more aggressive tumors, metastasis, and short survival rates (Mitsudomi et al., Clin Cancer Res 2000 October; 6(10):4055-63; Koshland, Science (1993) 262:1953).

The human p53 protein normally functions as a central integrator of signals including DNA damage, hypoxia, nucleotide deprivation, and oncogene activation (Prives, Cell (1998) 95:5-8). In response to these signals, p53 protein levels are greatly increased with the result that the accumulated p53 activates cell cycle arrest or apoptosis depending on the nature and strength of these signals. Indeed, multiple lines of experimental evidence have pointed to a key role for p53 as a tumor suppressor (Levine, Cell (1997) 88:323-331). For example, homozygous p53 "knockout" mice are developmentally normal but exhibit nearly 100% incidence of neoplasia in the first year of life (Donehower et al., Nature (1992) 356:215-221).

The biochemical mechanisms and pathways through which p53 functions in normal and cancerous cells are not fully understood, but one clearly important aspect of p53 function is its activity as a gene-specific transcriptional activator. Among the genes with known p53-response elements are several with well-characterized roles in either regulation of the cell cycle or apoptosis, including GADD45, p21/Waf1/Cip1, cyclin G, Bax, IGF-BP3, and MDM2 (Levine, Cell (1997) 88:323-331).

Microtubules have a central role in the regulation of cell shape and polarity during differentiation, chromosome partitioning at mitosis, and intracellular transport. Microtubules undergo rearrangements involving rapid transitions between stable and dynamic states during these processes. Microtubule affinity regulating kinases (MARK) are a novel family of protein kinases that phosphorylate microtubule-associated proteins and trigger microtubule disruption (Drewes, G., et al. (1997) Cell 89: 297-308).

Microtubule affinity regulating kinase 1 (MARK1) is a serine/threonine kinase that phosphorylates microtubule-associated protein tau, leading to disruption of microtubules. It shares 90% amino acid homology with the rat version of MARK1, and demonstrates ubiquitous expression with highest levels in testis and brain (Nagase, T. et al. (2000) DNA Res. 7:143-150).

EMK1 (MARK2) is a serine/threonine protein kinase with two isoforms, which differ by the presence or absence of a 162-bp alternative exon (Espinosa, L. and Navarro, E. (1998) Cytogenet. Cell Genet. 81:278-282). Both human isoforms are coexpressed in a number of cell lines and tissues, with the highest expression found in heart, brain, placenta, skeletal muscle, and pancreas, and at lower levels in lung, liver, and kidney (Inglis, J. et al. (1993) Mammalian Genome 4: 401-403). Due to the physical location of this gene, 11q12-q13, EMK1 is a candidate gene for carcinogenic events (Courseaux, A. et al. (1995) Mammalian Genome 6: 311-312), and has been associated with colon and prostate cancer (Moore, T. M., et al. (2000) J Biol Chem 275:4311-22; Navarro, E., et al. (1999) Biochim Biophys Acta 1450: 254-64).

Microtubule affinity regulating kinase 3 (MARK3) was originally identified as a marker (KP78) induced by treatment with DNA damaging agents. The loss of MARK3 was associated with carcinogenesis in the pancreas (Parsa, I. (1988) Cell Growth Differ. 9: 197-208). MARK3 may be involved in cell cycle regulation, and alterations in the MARK3 gene may lead to carcinogenesis. MARK 3 is ubiquitously expressed throughout human tissues, with an additional 3.0 Kb transcript present in the heart (Peng, C. et al. (1998) Cell Growth Differ. 9: 197-208).

MAP/microtubule affinity-regulating kinase like 1 (MARKL1) has two isoforms (Nagase, T. et al. (2001) DNA Res. 8: 85-95), is activated by the beta-catenin/Tcf complex in hepatic cell lines, and may be involved in hepatic carcinogenesis (Kato, T. et al. (2001). Neoplasia 3:4-9).

The ability to manipulate the genomes of model organisms such as *Drosophila* provides a powerful means to analyze biochemical processes that, due to significant evolutionary conservation, has direct relevance to more complex vertebrate organisms. Due to a high level of gene and pathway conservation, the strong similarity of cellular processes, and the functional conservation of genes between these model organisms and mammals, identification of the involvement of novel genes in particular pathways and their functions in such model organisms can directly contribute to the understanding of the correlative pathways and methods of modulating them in mammals (see, for example, Mechler B M et al., 1985 EMBO J 4:1551-1557; Gateff E. 1982 Adv. Cancer Res. 37: 33-74; Watson K L., et al., 1994 J Cell Sci. 18: 19-33; Miklos G L, and Rubin G M. 1996 Cell 86:521-529; Wassarman D A, et al., 1995 Curr Opin Gen Dev 5: 44-50; and Booth D R. 1999 Cancer Metastasis Rev. 18: 261-284). For example, a genetic screen can be carried out in an invertebrate model organism having underexpression (e.g. knockout) or overexpression of a gene (referred to as a "genetic entry point") that yields a visible phenotype. Additional genes are mutated in a random or targeted manner. When a gene mutation changes the original phenotype caused by the mutation in the genetic entry point, the gene is identified as a "modifier" involved in the same or overlapping pathway as the genetic entry point. When the genetic entry point is an ortholog of a human gene implicated in a disease pathway, such as p53, modifier genes can be identified that may be attractive candidate targets for novel therapeutics.

All references cited herein, including sequence information in referenced Genbank identifier numbers and website references, are incorporated herein in their entireties.

SUMMARY OF THE INVENTION

We have discovered genes that modify the p53 pathway in *Drosophila*, and identified their human orthologs, hereinafter referred to as MARK. The invention provides methods for utilizing these p53 modifier genes and polypeptides to identify candidate therapeutic agents that can be used in the treatment of disorders associated with defective p53 function. Preferred MARK-modulating agents specifically bind to MARK polypeptides and restore p53 function. Other preferred MARK-modulating agents are nucleic acid modulators such as antisense oligomers and RNAi that repress MARK gene expression or product activity by, for example, binding to and inhibiting the respective nucleic acid (i.e. DNA or mRNA).

MARK-specific modulating agents may be evaluated by any convenient in vitro or in vivo assay for molecular interaction with a MARK polypeptide or nucleic acid. In one embodiment, candidate p53 modulating agents are tested with an assay system comprising a MARK polypeptide or nucleic acid. Candidate agents that produce a change in the activity of the assay system relative to controls are identified as candidate p53 modulating agents. The assay system may be cell-based or cell-free. MARK-modulating agents include MARK related proteins (e.g. dominant negative mutants, and biotherapeutics); MARK-specific antibodies; MARK-specific antisense oligomers and other nucleic acid modulators; and chemical agents that specifically bind MARK or compete with MARK binding target. In one specific embodiment, a small molecule modulator is identified using a kinase assay. In specific embodiments, the screening assay system is selected from a binding assay, an apoptosis assay, a cell proliferation assay, an angiogenesis assay, and a hypoxic induction assay.

In another embodiment, candidate p53 pathway modulating agents are further tested using a second assay system that detects changes in the p53 pathway, such as angiogenic, apoptotic, or cell proliferation changes produced by the originally identified candidate agent or an agent derived from the original agent. The second assay system may use cultured cells or non-human animals. In specific embodiments, the secondary assay system uses non-human animals, including animals predetermined to have a disease or disorder implicating the p53 pathway, such as an angiogenic, apoptotic, or cell proliferation disorder (e.g. cancer).

The invention further provides methods for modulating the p53 pathway in a mammalian cell by contacting the mammalian cell with an agent that specifically binds a MARK polypeptide or nucleic acid. The agent may be a small molecule modulator, a nucleic acid modulator, or an antibody and may be administered to a mammalian animal predetermined to have a pathology associated the p53 pathway.

DETAILED DESCRIPTION OF THE INVENTION

Genetic screens were designed to identify modifiers of the p53 pathway in *Drosophila* in which p53 was overexpressed in the wing (Ollmann M, et al., Cell 2000 101: 91-101). The KP78a gene was identified as a modifier of the p53 pathway. Accordingly, vertebrate orthologs of these modifiers, and preferably the human orthologs, microtubule affinity regulator kinase (MARK) genes (i.e., nucleic acids and polypeptides) are attractive drug targets for the treatment of pathologies associated with a defective p53 signaling pathway, such as cancer.

In vitro and in vivo methods of assessing MARK function are provided herein. Modulation of the MARK or their respective binding partners is useful for understanding the association of the p53 pathway and its members in normal and disease conditions and for developing diagnostics and therapeutic modalities for p53 related pathologies. MARK-modulating agents that act by inhibiting or enhancing MARK expression, directly or indirectly, for example, by affecting a MARK function such as enzymatic (e.g., catalytic) or binding activity, can be identified using methods provided herein. MARK modulating agents are useful in diagnosis, therapy and pharmaceutical development.

Nucleic Acids and Polypeptides of the Invention

Sequences related to MARK nucleic acids and polypeptides that can be used in the invention are disclosed in Genbank (referenced by Genbank identifier (GI) number) as GI#s 9845486 (SEQ ID NO:1), 9845488 (SEQ ID NO:2), 18578044 (SEQ ID NO:3), 14250621 (SEQ ID NO:6), 15042610 (SEQ ID NO:7), 8923921 (SEQ ID NO:8), 17445805 (SEQ ID N0:9), 7959214 (SEQ ID NO:11), 14042208 (SEQ ID NO:12), 3089348 (SEQ ID NO:13), 4505102 (SEQ ID NO:14), 5714635 (SEQ ID NO:15), 18448970 (SEQ ID NO:18), 13366083 (SEQ ID NO:19), 14017936 (SEQ ID NO:22), and 16555377 (SEQ ID NO:23) for nucleic acid, and GI#s 9845487 (SEQ ID NO:24), 8923922 (SEQ ID NO:25), 3089349 (SEQ ID NO:26), 4505103 (SEQ ID NO:27), 13366084 (SEQ ID NO:28) and 13899225 (SEQ ID NO:29) for polypeptides. Additionally, nucleic acid sequences of SEQ ID NOs:4, 5, 16, 17, 20, 21, and novel nucleic acid sequence of SEQ ID NO:10 can also be used in the invention.

MARKs are kinase proteins with kinase and UBA/TS-N domains. The term "MARK polypeptide" refers to a full-length MARK protein or a functionally active fragment or derivative thereof. A "functionally active" MARK fragment or derivative exhibits one or more functional activities associated with a full-length, wild-type MARK protein, such as antigenic or immunogenic activity, enzymatic activity, ability to bind natural cellular substrates, etc. The functional activity of MARK proteins, derivatives and fragments can be assayed by various methods known to one skilled in the art (Current Protocols in Protein Science (1998) Coligan et al., eds., John Wiley & Sons, Inc., Somerset, New Jersey) and as further discussed below. For purposes herein, functionally active fragments also include those fragments that comprise one or more structural domains of a MARK, such as a kinase domain or a binding domain. Protein domains can be identified using the PFAM program (Bateman A., et al., Nucleic Acids Res, 1999, 27:260-2;. For example, the protein kinase domains of MARKs from GI#s 9845487 (SEQ II) NO:24), 8923922 (SEQ ID NO:25), 4505103 (SEQ ID NO:27), and 13899225 (SEQ ID NO:29) is located at approximately amino acid residues 20 to 271, 60 to 311, 56 to 307, and 59 to 310, respectively (PFAM 00069). Further, the ubiquitin associated (UBA/TS-N) domains of MARKS from GI#s 9845487 (SEQ ID NO:24), 8923922 (SEQ ID NO:25), 4505103 (SEQ ID NO:27 and 13899225 (SEQ ID NO:29) is located at approximately amino acid residues 291 to 330, 331 to 370, 327 to 366, and 330 to 369, respectively (PFAM 00627). Methods for obtaining MARK polypeptides are also further described below. In some embodiments, preferred fragments are functionally active, domain-containing fragments comprising at least 25 contiguous amino acids, preferably at least 50, more preferably 75, and most preferably at least 100 contiguous amino acids of any one of SEQ ID NOs:24, 25,26,27, 28, or 29 (a MARK). In further preferred embodiments, the fragment comprises the entire kinase (functionally active) domain.

The term "MARK nucleic acid" refers to a DNA or RNA molecule that encodes a MARK polypeptide. Preferably, the MARK polypeptide or nucleic acid or fragment thereof is from a human, but can also be an ortholog, or derivative thereof with at least 70% sequence identity, preferably at least 80%, more preferably 85%, still more preferably 90%, and most preferably at least 95% sequence identity with MARK. Normally, orthologs in different species retain the same function, due to presence of one or more protein motifs and/or 3-dimensional structures. Orthologs are generally identified by sequence homology analysis, such as BLAST analysis, usually using protein bait sequences. Sequences are assigned as a potential ortholog if the best hit sequence from the forward BLAST result retrieves the original query sequence in the reverse BLAST (Huynen MA and Bork P, Proc Nati Acad Sci (1998) 95:5849-5856; Huynen MA et al., (Genome Research (2000) 10:1204-1210). Programs for multiple sequence alignment, such as CLUSTAL (Thompson JD et al, 1994, Nucleic Acids Res 22:4673-4680) may be used to highlight conserved regions and/or residues of orthologous proteins and to generate phylogenetic trees. In a phylogenetic tree representing multiple homologous sequences from diverse species (e.g., retrieved through BLAST analysis), orthologous sequences from two species generally appear closest on the tree with respect to all other sequences from these two species. Structural threading or other analysis of protein folding (e.g., using software by ProCeryon, Biosciences, Salzburg, Austria) may also identify potential orthologs. In evolution, when a gene duplication event follows speciation, a single gene in one species, such as *Drosophila*, may correspond to multiple genes (paralogs) in another, such as human. As used herein, the term "orthologs" encompasses paralogs. As used herein, "percent (%) sequence identity" with respect to a subject sequence, or a specified portion of a subject sequence, is defined as the percentage of nucleotides or amino acids in the candidate derivative sequence identical with the nucleotides or amino acids in the subject sequence (or specified portion thereof), after aligning the sequences and introducing gaps, if necessary to achieve the maximum percent sequence identity, as generated by the program WU-BLAST-2.0a19 (Altschul et al., J. Mol. Biol. (1997) 215:403-410; with all the search parameters set to default values. The HSP S and HSP S2 parameters are dynamic values and are established by the program itself depending upon the composition of the particular sequence and composition of the particular database against which the sequence of interest is being searched. A % identity value is determined by the number of matching identical nucleotides or amino acids divided by the sequence length for which the percent identity is being reported. "Percent (%) amino acid sequence similarity" is determined by doing the same calculation as for determining % amino acid sequence identity, but including conservative amino acid substitutions in addition to identical amino acids in the computation.

A conservative amino acid substitution is one in which an amino acid is substituted for another amino acid having similar properties such that the folding or activity of the protein is not significantly affected. Aromatic amino acids that can be substituted for each other are phenylalanine, tryptophan, and tyrosine; interchangeable hydrophobic amino acids are leucine, isoleucine, methionine, and valine; interchangeable polar amino acids are glutamine and asparagine; interchangeable basic amino acids are arginine, lysine and histidine; interchangeable acidic amino acids are aspartic acid and glutamic acid; and interchangeable small amino acids are alanine, serine, threonine, cysteine and glycine.

Alternatively, an alignment for nucleic acid sequences is provided by the local homology algorithm of Smith and Waterman (Smith and Waterman, 1981, Advances in Applied Mathematics 2:482-489; database: European Bioinformatics Institute ; Smith and Waterman, 1981, J. of Molec.Biol., 147:195-197; Nicholas et al., 1998, "A Tutorial on Searching Sequence Databases and Sequence Scoring Methods" and references cited therein; W.R. Pearson, 1991, Genomics 11:635-650). This algorithm can be applied to amino acid sequences by using the scoring matrix developed by Dayhoff (Dayhoff: Atlas of Protein Sequences and Structure, M. 0. Dayhoff ed., 5 suppl. 3:353-358, National Biomedical Research Foundation, Washington, D.C., USA), and normalized by Gribskov (Gribskov 1986 Nucl. Acids Res. 14(6): 6745-6763). The Smith-Waterman algorithm may be employed where default parameters are used for scoring (for example, gap open penalty of 12, gap extension penalty of two). From the data generated, the "Match" value reflects "sequence identity."

Derivative nucleic acid molecules of the subject nucleic acid molecules include sequences that hybridize to the nucleic acid sequence of any of SEQ ID NOs:1 through 23. The stringency of hybridization can be controlled by temperature, ionic strength, pH, and the presence of denaturing agents such as formamide during hybridization and washing. Conditions routinely used are set out in readily available procedure texts (e.g., Current Protocol in Molecular Biology, Vol. 1, Chap. 2.10, John Wiley & Sons, Publishers (1994); Sambrook et al., Molecular Cloning, Cold Spring Harbor (1989)). In some embodiments, a nucleic acid molecule of the invention is capable of hybridizing to a nucleic acid molecule containing the nucleotide sequence of any one of SEQ ID NOs:1 through 23 under stringent hybridization conditions that comprise: prehybridization of filters containing nucleic acid for 8 hours to overnight at 65° C. in a solution comprising 6× single strength citrate (SSC) (1×SSC is 0.15 M NaCl, 0.015 M Na citrate; pH 7.0), 5×Denhardt's solution, 0.05% sodium pyrophosphate and 100 µg/ml herring sperm DNA; hybridization for 18-20 hours at 65° C. in a solution containing 6×SSC, 1×Denhardt's solution, 100 µg/ml yeast tRNA and 0.05% sodium pyrophosphate; and washing of filters at 65° C. for 1 h in a solution containing 0.2×SSC and 0.1% SDS (sodium dodecyl sulfate).

In other embodiments, moderately stringent hybridization conditions are used that comprise: pretreatment of filters containing nucleic acid for 6 h at 40° C. in a solution containing 35% formamide, 5×SSC, 50 mM Tris-HCl (pH7.5), 5mM EDTA, 0.1% PVP, 0.1% FICOLL®, 1% BSA, and 500 µg/ml denatured salmon sperm DNA; hybridization for 18-20h at 40° C. in a solution containing 35% formamide, 5×SSC, 50 mM Tris-HCl (pH7.5), 5mM EDTA, 0.02% PVP, 0.02% FICOLL®, 0.2% BSA, 100 µg/ml salmon sperm DNA, and 10% (wt/vol) dextran sulfate; followed by washing twice for 1 hour at 55° C. in a solution containing 2× SSC and 0.1% SDS.

Alternatively, low stringency conditions can be used that comprise: incubation for 8 hours to overnight at 37° C. in a solution comprising 20% formamide, 5×SSC, 50 mM sodium phosphate (pH 7.6), 5×Denhardt's solution, 10% dextran sulfate, and 20 µg/ml denatured sheared salmon sperm DNA; hybridization in the same buffer for 18 to 20 hours; and washing of filters in 1×SSC at about 37° C. for 1 hour.

Isolation, Production, Expression, and Mis-Expression of MARK Nucleic Acids and Polypeptides MARK nucleic acids and polypeptides, useful for identifying and testing agents that modulate MARK function and for other applications related to the involvement of MARK in the p53 pathway. MARK nucleic acids and derivatives and orthologs thereof may be obtained using any available method. For instance, techniques for isolating cDNA or genomic DNA sequences of interest by screening DNA libraries or by using polymerase chain reaction (PCR) are well known in the art. In general, the particular use for the protein will dictate the particulars of expression, production, and purification methods. For instance, production of proteins for use in screening for modulating agents may require methods that preserve specific biological activities of these proteins, whereas production of proteins for antibody generation may require structural integrity of particular epitopes. Expression of proteins to be purified for screening or antibody production may require the addition of specific tags (e.g., generation of fusion proteins). Overexpression of a MARK protein for assays used to assess MARK function, such as involvement in cell cycle regulation or hypoxic response, may require expression in eukaryotic cell lines capable of these cellular activities. Techniques for the expression, production, and purification of proteins are well known in the art; any suitable means therefore may be used (e.g., Higgins S J and Hames B D (eds.) Protein Expression: A Practical Approach, Oxford University Press Inc., New York 1999; Stanbury P F et al., Principles of Fermentation Technology, $2^{nd}$ edition, Elsevier Science, New York, 1995; Doonan S (ed.) Protein Purification Protocols, Humana Press, New Jersey, 1996; Coligan J E et al, Current Protocols in Protein Science (eds.), 1999, John Wiley & Sons, New York). In particular embodiments, recombinant MARK is expressed in a cell line known to have defective p53 function (e.g. SAOS-2 osteoblasts, H1299 lung cancer cells, C33A and HT3 cervical cancer cells, HT-29 and DLD-1 colon cancer cells, among others, available from American Type Culture Collection (ATCC), Manassas, Va.). The recombinant cells are used in cell-based screening assay systems of the invention, as described further below.

The nucleotide sequence encoding a MARK polypeptide can be inserted into any appropriate expression vector. The necessary transcriptional and translational signals, including promoter/enhancer element, can derive from the native MARK gene and/or its flanking regions or can be heterologous. A variety of host-vector expression systems may be utilized, such as mammalian cell systems infected with virus (e.g. vaccinia virus, adenovirus, etc.); insect cell systems infected with virus (e.g. baculovirus); microorganisms such as yeast containing yeast vectors, or bacteria transformed with bacteriophage, plasmid, or cosmid DNA. A host cell strain that modulates the expression of, modifies, and/or specifically processes the gene product may be used.

To detect expression of the MARK gene product, the expression vector can comprise a promoter operably linked to a MARK gene nucleic acid, one or more origins of replication, and, one or more selectable markers (e.g. thymidine kinase activity, resistance to antibiotics, etc.). Alternatively, recombinant expression vectors can be identified by assaying for the expression of the MARK gene product based on the physical or functional properties of the MARK protein in in vitro assay systems (e.g. immunoassays).

The MARK protein, fragment, or derivative may be optionally expressed as a fusion, or chimeric protein product (i.e. it is joined via a peptide bond to a heterologous protein sequence of a different protein), for example to facilitate purification or detection. A chimeric product can be made by ligating the appropriate nucleic acid sequences encoding the desired amino acid sequences to each other using standard methods and expressing the chimeric product. A chimeric product may also be made by protein synthetic techniques, e.g. by use of a peptide synthesizer (Hunkapiller et al., Nature (1984) 310:105-111).

Once a recombinant cell that expresses the MARK gene sequence is identified, the gene product can be isolated and purified using standard methods (e.g. ion exchange, affinity, and gel exclusion chromatography; centrifugation; differential solubility; electrophoresis, cite purification reference). Alternatively, native MARK proteins can be purified from natural sources, by standard methods (e.g. immunoaffinity purification). Once a protein is obtained, it may be quantified and its activity measured by appropriate methods, such as immunoassay, bioassay, or other measurements of physical properties, such as crystallography.

The methods of this invention may also use cells that have been engineered for altered expression (mis-expression) of MARK or other genes associated with the p53 pathway. As used herein, mis-expression encompasses ectopic expression, over-expression, under-expression, and non-expression (e.g. by gene knock-out or blocking expression that would otherwise normally occur).

Genetically Modified Animals

Animal models that have been genetically modified to alter MARK expression may be used in in vivo assays to test for activity of a candidate p53 modulating agent, or to further assess the role of MARK in a p53 pathway process such as apoptosis or cell proliferation. Preferably, the altered MARK expression results in a detectable phenotype, such as decreased or increased levels of cell proliferation, angiogenesis, or apoptosis compared to control animals having normal MARK expression. The genetically modified animal may additionally have altered p53 expression (e.g. p53 knockout). Preferred genetically modified animals are mammals such as primates, rodents (preferably mice), cows, horses, goats, sheep, pigs, dogs and cats. Preferred non-mammalian species include zebrafish, *C. elegans*, and *Drosophila*. Preferred genetically modified animals are transgenic animals having a heterologous nucleic acid sequence present as an extrachromosomal element in a portion of its cells, i.e. mosaic animals (see, for example, techniques described by Jakobovits, 1994, Curr. Biol. 4:761-763.) or stably integrated into its germ line DNA (i.e., in the genomic sequence of most or all of its cells). Heterologous nucleic acid is introduced into the germ line of such transgenic animals by genetic manipulation of, for example, embryos or embryonic stem cells of the host animal.

Methods of making transgenic animals are well-known in the art (for transgenic mice see Brinster et al., Proc. Nat. Acad. Sci. USA 82: 4438-4442 (1985), U.S. Pat. Nos. 4,736,866 and 4,870,009, both by Leder et al., U.S. Pat. No. 4,873,191 by Wagner et al., and Hogan, B., Manipulating the Mouse Embryo, Cold Spring Harbor Laboratory Press, Cold Spring Harbor, N.Y., (1986); for particle bombardment see U.S. Pat. No. 4,945,050, by Sandford et al.; for transgenic *Drosophila* see Rubin and Spradling, Science (1982) 218:348-53 and U.S. Pat. No. 4,670,388; for transgenic insects see Berghammer A. J. et al., A Universal Marker for Transgenic Insects (1999) Nature 402:370-371; for transgenic Zebrafish see Lin S., Transgenic Zebrafish, Methods Mol Biol. (2000); 136: 375-3830); for microinjection procedures for fish, amphibian eggs and birds see Houdebine and Chourrout, Experientia (1991) 47:897-905; for transgenic rats see Hammer et al., Cell (1990) 63:1099-1112; and for culturing of embryonic stem (ES) cells and the subsequent production of transgenic animals by the introduction of DNA into ES cells using methods such as electroporation, calcium phosphate/DNA precipitation and direct injection see, e.g., Teratocarcinomas and Embryonic Stem Cells, A Practical Approach, E. J. Robertson, ed., IRL Press (1987)). Clones of the nonhuman transgenic animals can be produced according to available methods (see Wilmut, I. et al. (1997) Nature 385:810-813; and PCT International Publication Nos. WO 97/07668 and WO 97/07669).

In one embodiment, the transgenic animal is a "knock-out" animal having a heterozygous or homozygous alteration in the sequence of an endogenous MARK gene that results in a decrease of MARK function, preferably such that MARK expression is undetectable or insignificant. Knock-out animals are typically generated by homologous recombination with a vector comprising a transgene having at least a portion of the gene to be knocked out. Typically a deletion, addition or substitution has been introduced into the transgene to functionally disrupt it. The transgene can be a human gene (e.g., from a human genomic clone) but more preferably is an ortholog of the human gene derived from the transgenic host species. For example, a mouse MARK gene is used to construct a homologous recombination vector suitable for altering an endogenous MARK gene in the mouse genome. Detailed methodologies for homologous recombination in mice are available (see Capecchi, Science (1989) 244:1288-1292; Joyner et al., Nature (1989) 338:153-156). Procedures for the production of non-rodent transgenic mammals and other animals are also available (Houdebine and Chourrout, supra; Pursel et al., Science (1989) 244:1281-1288; Simms et al., Bio/Technology (1988) 6:179-183). In a preferred embodiment, knock-out animals, such as mice harboring a knockout of a specific gene, may be used to produce antibodies against the human counterpart of the gene that has been knocked out (Claesson M H et al., (1994) Scan J Immunol 40:257-264; Declerck P J et al., (1995) J Biol Chem. 270: 8397-400).

In another embodiment, the transgenic animal is a "knock-in" animal having an alteration in its genome that results in altered expression (e.g., increased (including ectopic) or decreased expression) of the MARK gene, e.g., by introduction of additional copies of MARK, or by operatively inserting a regulatory sequence that provides for altered expression of an endogenous copy of the MARK gene. Such regulatory sequences include inducible, tissue-specific, and constitutive promoters and enhancer elements. The knock-in can be homozygous or heterozygous.

Transgenic nonhuman animals can also be produced that contain selected systems allowing for regulated expression of the transgene. One example of such a system that may be produced is the cre/loxP recombinase system of bacteriophage P1 (Lakso et al., PNAS (1992) 89:6232-6236; U.S. Pat. No. 4,959,317). If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase. Another example of a recombinase system is the FLP recombinase system of Saccharomyces cerevisiae (O'Gorman et al. (1991) Science 251:1351-1355; U.S. Pat. No. 5,654,182). In a preferred embodiment, both Cre-LoxP and Flp-Frt are used in the same system to regulate expression of the transgene, and for sequential deletion of vector sequences in the same cell (Sun X et al (2000) Nat Genet 25:83-6).

The genetically modified animals can be used in genetic studies to further elucidate the p53 pathway, as animal models of disease and disorders implicating defective p53 function, and for in vivo testing of candidate therapeutic agents, such as those identified in screens described below. The candidate therapeutic agents are administered to a genetically modified animal having altered MARK function and phenotypic changes are compared with appropriate control animals such as genetically modified animals that receive placebo treatment, and/or animals with unaltered MARK expression that receive candidate therapeutic agent.

In addition to the above-described genetically modified animals having altered MARK function, animal models having defective p53 function (and otherwise normal MARK function), can be used in the methods of the present invention. For example, a p53 knockout mouse can be used to assess, in vivo, the activity of a candidate p53 modulating agent identified in one of the in vitro assays described below. p53 knockout mice are described in the literature (Jacks et al., Nature 2001; 410:1111-1116, 1043-1044; Donehower et al., supra). Preferably, the candidate p53 modulating agent when administered to a model system with cells defective in p53 function, produces a detectable phenotypic change in the model system indicating that the p53 function is restored, i.e., the cells exhibit normal cell cycle progression.

Modulating Agents

The invention provides methods to identify agents that interact with and/or modulate the function of MARK and/or the p53 pathway. Such agents are useful in a variety of diagnostic and therapeutic applications associated with the p53 pathway, as well as in further analysis of the MARK protein and its contribution to the p53 pathway. Accordingly, the invention also provides methods for modulating the p53 pathway comprising the step of specifically modulating MARK activity by administering a MARK-interacting or -modulating agent.

In a preferred embodiment, MARK-modulating agents inhibit or enhance MARK activity or otherwise affect normal MARK function, including transcription, protein expression, protein localization, and cellular or extra-cellular activity. In a further preferred embodiment, the candidate p53 pathway-modulating agent specifically modulates the function of the MARK. The phrases "specific modulating agent", "specifically modulates", etc., are used herein to refer to modulating agents that directly bind to the MARK polypeptide or nucleic acid, and preferably inhibit, enhance, or otherwise alter, the function of the MARK. The term also encompasses modulating agents that alter the interaction of the MARK with a binding partner or substrate (e.g. by binding to a binding partner of a MARK, or to a protein/binding partner complex, and inhibiting function).

Preferred MARK-modulating agents include small molecule compounds; MARK-interacting proteins, including antibodies and other biotherapeutics; and nucleic acid modulators such as antisense and RNA inhibitors. The modulating agents may be formulated in pharmaceutical compositions, for example, as compositions that may comprise other active ingredients, as in combination therapy, and/or suitable carriers or excipients. Techniques for formulation and administration of the compounds may be found in "Remington's Pharmaceutical Sciences" Mack Publishing Co., Easton, Pa., 19$^{th}$ edition.

Small Molecule Modulators

Small molecules, are often preferred to modulate function of proteins with enzymatic function, and/or containing protein interaction domains. Chemical agents, referred to in the art as "small molecule" compounds are typically organic, non-peptide molecules, having a molecular weight less than 10,000, preferably less than 5,000, more preferably less than 1,000, and most preferably less than 500. This class of modulators includes chemically synthesized molecules, for instance, compounds from combinatorial chemical libraries. Synthetic compounds may be rationally designed or identified based on known or inferred properties of the MARK protein or may be identified by screening compound libraries.

Alternative appropriate modulators of this class are natural products, particularly secondary metabolites from organisms such as plants or fungi, which can also be identified by screening compound libraries for MARK-modulating activity. Methods for generating and obtaining compounds are well known in the art (Schreiber S L, Science (2000) 151: 1964-1969; Radmann J and Gunther J, Science (2000) 151:1947-1948).

Small molecule modulators identified from screening assays, as described below, can be used as lead compounds from which candidate clinical compounds may be designed, optimized, and synthesized. Such clinical compounds may have utility in treating pathologies associated with the p53 pathway. The activity of candidate small molecule modulating agents may be improved several-fold through iterative secondary functional validation, as further described below, structure determination, and candidate modulator modification and testing. Additionally, candidate clinical compounds are generated with specific regard to clinical and pharmacological properties. For example, the reagents may be derivatized and re-screened using in vitro and in vivo assays to optimize activity and minimize toxicity for pharmaceutical development.

Protein Modulators

Specific MARK-interacting proteins are useful in a variety of diagnostic and therapeutic applications related to the p53 pathway and related disorders, as well as in validation assays for other MARK-modulating agents. In a preferred embodiment, MARK-interacting proteins affect normal MARK function, including transcription, protein expression, protein localization, and cellular or extra-cellular activity. In another embodiment, MARK-interacting proteins are useful in detecting and providing information about the function of MARK proteins, as is relevant to p53 related disorders, such as cancer (e.g., for diagnostic means).

An MARK-interacting protein may be endogenous, i.e. one that naturally interacts genetically or biochemically with a MARK, such as a member of the MARK pathway that modulates MARK expression, localization, and/or activity. MARK-modulators include dominant negative forms of MARK-interacting proteins and of MARK proteins themselves. Yeast two-hybrid and variant screens offer preferred methods for identifying endogenous MARK-interacting proteins (Finley, R. L. et al. (1996) in DNA Cloning-Expression Systems: A Practical Approach, eds. Glover D. & Hames B. D (Oxford University Press, Oxford, England), pp. 169-203; Fashema S F et al., Gene (2000) 250:1-14; Drees B L Curr Opin Chem Biol (1999) 3:64-70; Vidal M and Legrain P Nucleic Acids Res (1999) 27:919-29; and U.S. Pat. No. 5,928,868). Mass spectrometry is an alternative preferred method for the elucidation of protein complexes (reviewed in, e.g., Pandley A and Mann M, Nature (2000) 405:837-846; Yates J R 3$^{rd}$, Trends Genet (2000) 16:5-8).

An MARK-interacting protein may be an exogenous protein, such as a MARK-specific antibody or a T-cell antigen receptor (see, e.g., Harlow and Lane (1988) Antibodies, A Laboratory Manual, Cold Spring Harbor Laboratory; Harlow and Lane (1999) Using antibodies: a laboratory manual. Cold Spring Harbor, N.Y.: Cold Spring Harbor Laboratory Press). MARK antibodies are further discussed below.

In preferred embodiments, a MARK-interacting protein specifically binds a MARK protein. In alternative preferred embodiments, a MARK-modulating agent binds a MARK substrate, binding partner, or cofactor.

Antibodies

In another embodiment, the protein modulator is a MARK specific antibody agonist or antagonist. The antibodies have therapeutic and diagnostic utilities, and can be used in screening assays to identify MARK modulators. The antibodies can also be used in dissecting the portions of the MARK pathway responsible for various cellular responses and in the general processing and maturation of the MARK.

Antibodies that specifically bind MARK polypeptides can be generated using known methods. Preferably the antibody is specific to a mammalian ortholog of MARK polypeptide, and more preferably, to human MARK. Antibodies may be polyclonal, monoclonal (mAbs), humanized or chimeric antibodies, single chain antibodies, Fab fragments, F(ab').sub.2 fragments, fragments produced by a FAb expression library, anti-idiotypic (anti-Id) antibodies, and epitope-binding fragments of any of the above. Epitopes of MARK which are particularly antigenic can be selected, for example, by routine screening of MARK polypeptides for antigenicity or by applying a theoretical method for selecting antigenic regions of a protein (Hopp and Wood (1981), Proc. Nati. Acad. Sci. U.S.A. 78:3824-28; Hopp and Wood, (1983) Mol. Immunol. 20:483-89; Sutcliffe et al., (1983) Science 219:660-66) to the amino acid sequence shown in any of SEQ ID NOs:24, 25, 26, 27, 28, or 29. Monoclonal antibodies with affinities of $10^8$ $M^{-1}$ preferably $10^9 M^{-1}$ to $10^{10} M^{-1}$, or stronger can be made by standard procedures as described (Harlow and Lane, supra; Goding (1986) Monoclonal Antibodies: Principles and Practice (2d ed) Academic Press, New York; and U.S. Pat. Nos. 4,381,292; 4,451,570; and 4,618,577). Antibodies may be generated against crude cell extracts of MARK or substantially purified fragments thereof. If MARK fragments are used, they preferably comprise at least 10, and more preferably, at least 20 contiguous amino acids of a MARK protein. In a particular embodiment, MARK-specific antigens and/or immunogens are coupled to carrier proteins that stimulate the immune response. For example, the subject polypeptides are covalently coupled to the keyhole limpet hemocyanin (KLH) carrier, and the conjugate is emulsified in Freund's complete adjuvant, which enhances the immune response. An appropriate immune system such as a laboratory rabbit or mouse is immunized according to conventional protocols.

The presence of MARK-specific antibodies is assayed by an appropriate assay such as a solid phase enzyme-linked immunosorbant assay (ELISA) using immobilized corresponding MARK polypeptides. Other assays, such as radio-immunoassays or fluorescent assays might also be used.

Chimeric antibodies specific to MARK polypeptides can be made that contain different portions from different animal species. For instance, a human immunoglobulin constant region may be linked to a variable region of a murine mAb, such that the antibody derives its biological activity from the human antibody, and its binding specificity from the murine fragment. Chimeric antibodies are produced by splicing together genes that encode the appropriate regions from each species (Morrison et al., Proc. Natl. Acad. Sci. (1984) 81:6851-6855; Neuberger et al., Nature (1984) 312:604-608; Takeda et al., Nature (1985) 31:452-454). Humanized antibodies, which are a form of chimeric antibodies, can be generated by grafting complementary-determining regions (CDRs) (Carlos, T. M., J. M. Harlan. 1994. Blood 84:2068-2101) of mouse antibodies into a background of human framework regions and constant regions by recombinant DNA technology (Riechmann LM, et al., 1988 Nature 323: 323-327). Humanized antibodies contain ~10% murine sequences and ~90% human sequences, and thus further reduce or eliminate immunogenicity, while retaining the antibody specificities (Co M S, and Queen C. 1991 Nature 351: 501-501; Morrison S L. 1992 Ann. Rev. Immun. 10:239-265).

Humanized antibodies and methods of their production are well-known in the art (U.S. Pat. Nos. 5,530,101, 5,585,089, 5,693,762, and 6,180,370).

MARK-specific single chain antibodies which are recombinant, single chain polypeptides formed by linking the heavy and light chain fragments of the Fv regions via an amino acid bridge, can be produced by methods known in the art (U.S. Pat. No. 4,946,778; Bird, Science (1988) 242:423-426; Huston et al., Proc. Natl. Acad. Sci. USA (1988) 85:5879-5883; and Ward et al., Nature (1989) 334:544-546).

Other suitable techniques for antibody production involve in vitro exposure of lymphocytes to the antigenic polypeptides or alternatively to selection of libraries of antibodies in phage or similar vectors (Huse et al., Science (1989) 246: 1275-1281). As used herein, T-cell antigen receptors are included within the scope of antibody modulators (Harlow and Lane, 1988, supra).

The polypeptides and antibodies of the present invention may be used with or without modification. Frequently, antibodies will be labeled by joining, either covalently or non-covalently, a substance that provides for a detectable signal, or that is toxic to cells that express the targeted protein (Menard S, et al., Int J. Biol Markers (1989) 4:131-134). A wide variety of labels and conjugation techniques are known and are reported extensively in both the scientific and patent literature. Suitable labels include radionuclides, enzymes, substrates, cofactors, inhibitors, fluorescent moieties, fluorescent emitting lanthanide metals, chemiluminescent moieties, bioluminescent moieties, magnetic particles, and the like (U.S. Pat. Nos. 3,817,837; 3,850,752; 3,939,350; 3,996,345; 4,277,437; 4,275,149; and 4,366,241). Also, recombinant immunoglobulins may be produced (U.S. Pat. No. 4,816, 567). Antibodies to cytoplasmic polypeptides may be delivered and reach their targets by conjugation with membrane-penetrating toxin proteins (U.S. Pat. No. 6,086,900).

When used therapeutically in a patient, the antibodies of the subject invention are typically administered parenterally, when possible at the target site, or intravenously. The therapeutically effective dose and dosage regimen is determined by clinical studies. Typically, the amount of antibody administered is in the range of about 0.1 mg/kg-to about 10 mg/kg of patient weight. For parenteral administration, the antibodies are formulated in a unit dosage injectable form (e.g., solution, suspension, emulsion) in association with a pharmaceutically acceptable vehicle. Such vehicles are inherently nontoxic and non-therapeutic. Examples are water, saline, Ringer's solution, dextrose solution, and 5% human serum albumin. Nonaqueous vehicles such as fixed oils, ethyl oleate, or liposome carriers may also be used. The vehicle may contain minor amounts of additives, such as buffers and preservatives, which enhance isotonicity and chemical stability or otherwise enhance therapeutic potential. The antibodies' concentrations in such vehicles are typically in the range of about 1 mg/ml to about 10 mg/ml. Immunotherapeutic methods are further described in the literature (U.S. Pat. No. 5,859, 206; WO0073469).

Nucleic Acid Modulators

Other preferred MARK-modulating agents comprise nucleic acid molecules, such as antisense oligomers or double stranded RNA (dsRNA), which generally inhibit MARK activity. Preferred nucleic acid modulators interfere with the function of the MARK nucleic acid such as DNA replication, transcription, translocation of the MARK RNA to the site of protein translation, translation of protein from the MARK RNA, splicing of the MARK RNA to yield one or more mRNA species, or catalytic activity which may be engaged in or facilitated by the MARK RNA.

In one embodiment, the antisense oligomer is an oligonucleotide that is sufficiently complementary to a MARK mRNA to bind to and prevent translation, preferably by binding to the 5' untranslated region. MARK-specific antisense oligonucleotides, preferably range from at least 6 to about 200 nucleotides. In some embodiments the oligonucleotide is preferably at least 10, 15, or 20 nucleotides in length. In other embodiments, the oligonucleotide is preferably less than 50, 40, or 30 nucleotides in length. The oligonucleotide can be DNA or RNA or a chimeric mixture or derivatives or modified versions thereof, single-stranded or double-stranded. The oligonucleotide can be modified at the base moiety, sugar moiety, or phosphate backbone. The oligonucleotide may include other appending groups such as peptides, agents that facilitate transport across the cell membrane, hybridization-triggered cleavage agents, and intercalating agents.

In another embodiment, the antisense oligomer is a phosphothioate morpholino oligomer (PMO). PMOs are assembled from four different morpholino subunits, each of which contain one of four genetic bases (A, C, G, or T) linked to a six-membered morpholine ring. Polymers of these subunits are joined by non-ionic phosphordiamidate intersubunit linkages. Details of how to make and use PMOs and other antisense oligomers are well known in the art (e.g. see WO99/18193; Probst J C, Antisense Oligodeoxynucleotide and Ribozyme Design, Methods. (2000) 22(3):271-281; Summerton J, and Weller D. 1997 Antisense Nucleic Acid Drug Dev.: 7:187-95; U.S. Pat. No. 5,235,033; and U.S. Pat. No. 5,378,841).

Alternative preferred MARK nucleic acid modulators are double-stranded RNA species mediating RNA interference (RNAi). RNAi is the process of sequence-specific, post-transcriptional gene silencing in animals and plants, initiated by double-stranded RNA (dsRNA) that is homologous in sequence to the silenced gene. Methods relating to the use of RNAi to silence genes in C. elegans, Drosophila, plants, and humans are known in the art (Fire A, et al., 1998 Nature 391:806-811; Fire, A. Trends Genet. 15, 358-363 (1999); Sharp, P. A. RNA interference 2001. Genes Dev. 15, 485-490 (2001); Hammond, S. M., et al., Nature Rev. Genet. 2, 110-1119 (2001); Tuschl, T. Chem. Biochem. 2, 239-245 (2001); Hamilton, A. et al., Science 286, 950-952 (1999); Hammond, S. M., et al., Nature 404, 293-296 (2000); Zamore, P. D., et al., Cell 101, 25-33 (2000); Bernstein, E., et al., Nature 409, 363-366 (2001); Elbashir, S. M., et al., Genes Dev. 15, 188-200 (2001); WO0129058; WO9932619; Elbashir S M, et al., 2001 Nature 411:494-498).

Nucleic acid modulators are commonly used as research reagents, diagnostics, and therapeutics. For example, antisense oligonucleotides, which are able to inhibit gene expression with exquisite specificity, are often used to elucidate the function of particular genes (see, for example, U.S. Pat. No. 6,165,790). Nucleic acid modulators are also used, for example, to distinguish between functions of various members of a biological pathway. For example, antisense oligomers have been employed as therapeutic moieties in the treatment of disease states in animals and man and have been demonstrated in numerous clinical trials to be safe and effective (Milligan J F, et al, Current Concepts in Antisense Drug Design, J Med Chem. (1993) 36:1923-1937; Tonkinson J L et al., Antisense Oligodeoxynucleotides as Clinical Therapeutic Agents, Cancer Invest. (1996) 14:54-65). Accordingly, in one aspect of the invention, a MARK-specific nucleic acid modulator is used in an assay to further elucidate the role of the MARK in the p53 pathway, and/or its relationship to other members of the pathway. In another aspect of the invention, a MARK-specific antisense oligomer is used as a therapeutic agent for treatment of p53-related disease states.

Assay Systems

The invention provides assay systems and screening methods for identifying specific modulators of MARK activity. As used herein, an "assay system" encompasses all the components required for performing and analyzing results of an assay that detects and/or measures a particular event. In general, primary assays are used to identify or confirm a modulator's specific biochemical or molecular effect with respect to the MARK nucleic acid or protein. In general, secondary assays further assess the activity of a MARK modulating agent identified by a primary assay and may confirm that the modulating agent affects MARK in a manner relevant to the p53 pathway. In some cases, MARK modulators will be directly tested in a secondary assay.

In a preferred embodiment, the screening method comprises contacting a suitable assay system comprising a MARK polypeptide with a candidate agent under conditions whereby, but for the presence of the agent, the system provides a reference activity (e.g. kinase activity), which is based on the particular molecular event the screening method detects. A statistically significant difference between the agent-biased activity and the reference activity indicates that the candidate agent modulates MARK activity, and hence the p53 pathway.

Primary Assays

The type of modulator tested generally determines the type of primary assay.

Primary Assays for Small Molecule Modulators

For small molecule modulators, screening assays are used to identify candidate modulators. Screening assays may be cell-based or may use a cell-free system that recreates or retains the relevant biochemical reaction of the target protein (reviewed in Sittampalam G S et al., Curr Opin Chem Biol (1997) 1:384-91 and accompanying references). As used herein the term "cell-based" refers to assays using live cells, dead cells, or a particular cellular fraction, such as a membrane, endoplasmic reticulum, or mitochondrial fraction. The term "cell free" encompasses assays using substantially purified protein (either endogenous or recombinantly produced), partially purified or crude cellular extracts. Screening assays may detect a variety of molecular events, including protein-DNA interactions, protein-protein interactions (e.g., receptor-ligand binding), transcriptional activity (e.g., using a reporter gene), enzymatic activity (e.g., via a property of the substrate), activity of second messengers, immunogenicity and changes in cellular morphology or other cellular characteristics. Appropriate screening assays may use a wide range of detection methods including fluorescent, radioactive, colorimetric, spectrophotometric, and amperometric methods, to provide a read-out for the particular molecular event detected.

Cell-based screening assays usually require systems for recombinant expression of MARK and any auxiliary proteins demanded by the particular assay. Appropriate methods for generating recombinant proteins produce sufficient quantities of proteins that retain their relevant biological activities and are of sufficient purity to optimize activity and assure assay reproducibility. Yeast two-hybrid and variant screens, and mass spectrometry provide preferred methods for determining protein-protein interactions and elucidation of protein complexes. In certain applications, when MARK-interacting proteins are used in screens to identify small molecule modulators, the binding specificity of the interacting protein to the MARK protein may be assayed by various known methods such as substrate processing (e.g. ability of the candidate MARK-specific binding agents to function as negative effectors in MARK-expressing cells), binding equilibrium constants (usually at least about $10^7 M^{-1}$, preferably at least about $10^8 M^{-1}$, more preferably at least about $10^9 M^{-1}$), and immunogenicity (e.g. ability to elicit MARK specific antibody in a heterologous host such as a mouse, rat, goat or rabbit). For enzymes and receptors, binding may be assayed by, respectively, substrate and ligand processing.

The screening assay may measure a candidate agent's ability to specifically bind to or modulate activity of a MARK polypeptide, a fusion protein thereof, or to cells or membranes bearing the polypeptide or fusion protein. The MARK polypeptide can be full length or a fragment thereof that retains functional MARK activity. The MARK polypeptide may be fused to another polypeptide, such as a peptide tag for detection or anchoring, or to another tag. The MARK polypeptide is preferably human MARK, or is an ortholog or derivative thereof as described above. In a preferred embodiment, the screening assay detects candidate agent-based modulation of MARK interaction with a binding target, such as an endogenous or exogenous protein or other substrate that has MARK-specific binding activity, and can be used to assess normal MARK gene function.

Suitable assay formats that may be adapted to screen for MARK modulators are known in the art. Preferred screening assays are high throughput or ultra high throughput and thus provide automated, cost-effective means of screening compound libraries for lead compounds (Fernandes P B, Curr Opin Chem Biol (1998) 2:597-603; Sundberg S A, Curr Opin Biotechnol 2000, 11:47-53). In one preferred embodiment, screening assays uses fluorescence technologies, including fluorescence polarization, time-resolved fluorescence, and fluorescence resonance energy transfer. These systems offer means to monitor protein-protein or DNA-protein interactions in which the intensity of the signal emitted from dye-labeled molecules depends upon their interactions with partner molecules (e.g., Selvin P R, Nat Struct Biol (2000) 7:730-4; Fernandes P B, supra; Hertzberg R P and Pope A J, Curr Opin Chem Biol (2000) 4:445-451).

A variety of suitable assay systems may be used to identify candidate MARK and p53 pathway modulators (e.g. U.S. Pat. No. 6,165,992 (kinase assays); U.S. Pat. Nos. 5,550,019 and 6,133,437 (apoptosis assays); U.S. Pat. No. 6,020,135 (p53 modulation), among others). Specific preferred assays are described in more detail below.

Kinase assays. In some preferred embodiments the screening assay detects the ability of the test agent to modulate the kinase activity of a MARK polypeptide. In further embodiments, a cell-free kinase assay system is used to identify a candidate p53 modulating agent, and a secondary, cell-based assay, such as an apoptosis or hypoxic induction assay (described below), may be used to further characterize the candidate p53 modulating agent. Many different assays for kinases have been reported in the literature and are well known to those skilled in the art (e.g. U.S. Pat. No. 6,165,992; Zhu et al., Nature Genetics (2000) 26:283-289; and WO0073469). Radioassays, which monitor the transfer of a gamma phosphate are frequently used. For instance, a scintillation assay for p56 (lck) kinase activity monitors the transfer of the gamma phosphate from gamma-$^{33}$P ATP to a biotinylated peptide substrate; the substrate is captured on a streptavidin coated bead that transmits the signal (Beveridge M et al., J Biomol Screen (2000) 5:205-212). This assay uses the scintillation proximity assay (SPA), in which only radio-ligand bound to receptors tethered to the surface of an SPA bead are detected by the scintillant immobilized within it, allowing binding to be measured without separation of bound from free ligand.

Other assays for protein kinase activity may use antibodies that specifically recognize phosphorylated substrates. For instance, the kinase receptor activation (KIRA) assay measures receptor tyrosine kinase activity by ligand stimulating the intact receptor in cultured cells, then capturing solubilized receptor with specific antibodies and quantifying phosphorylation via phosphotyrosine ELISA (Sadick M D, Dev Biol Stand (1999) 97:121-133).

Another example of antibody based assays for protein kinase activity is TRF (time-resolved fluorometry). This method utilizes europium chelate-labeled anti-phosphotyrosine antibodies to detect phosphate transfer to a polymeric substrate coated onto microtiter plate wells. The amount of phosphorylation is then detected using time-resolved, dissociation-enhanced fluorescence (Braunwalder A F, et al., Anal Biochem 1996 Jul. 1; 238(2):159-64).

Apoptosis assays. Assays for apoptosis may be performed by terminal deoxynucleotidyl transferase-mediated digoxigenin-11-dUTP nick end labeling (TUNEL) assay. The TUNEL assay is used to measure nuclear DNA fragmentation characteristic of apoptosis (Lazebnik et al., 1994, Nature 371, 346), by following the incorporation of fluorescein-dUTP (Yonehara et al., 1989, J. Exp. Med. 169, 1747). Apoptosis may further be assayed by acridine orange staining of tissue culture cells (Lucas, R., et al., 1998, Blood 15:4730-41). An apoptosis assay system may comprise a cell that expresses a MARK, and that optionally has defective p53 function (e.g. p53 is over-expressed or under-expressed relative to wild-type cells). A test agent can be added to the apoptosis assay system and changes in induction of apoptosis relative to controls where no test agent is added, identify candidate p53 modulating agents. In some embodiments of the invention, an apoptosis assay may be used as a secondary assay to test a candidate p53 modulating agents that is initially identified using a cell-free assay system. An apoptosis assay may also be used to test whether MARK function plays a direct role in apoptosis. For example, an apoptosis assay may be performed on cells that over- or under-express MARK relative to wild type cells. Differences in apoptotic response compared to wild type cells suggests that the MARK plays a direct role in the apoptotic response. Apoptosis assays are described further in U.S. Pat. No. 6,133,437.

Cell proliferation and cell cycle assays. Cell proliferation may be assayed via bromodeoxyuridine (BRDU) incorporation. This assay identifies a cell population undergoing DNA synthesis by incorporation of BRDU into newly-synthesized DNA. Newly-synthesized DNA may then be detected using an anti-BRDU antibody (Hoshino et al., 1986, Int. J. Cancer 38, 369; Campana et al., 1988, J. Immunol. Meth. 107, 79), or by other means.

Cell Proliferation may also be examined using [$^3$H]-thymidine incorporation (Chen, J., 1996, Oncogene 13:1395-403; Jeoung, J., 1995, J. Biol. Chem. 270:18367-73). This assay allows for quantitative characterization of S-phase DNA syntheses. In this assay, cells synthesizing DNA will incorporate [$^3$H]-thymidine into newly synthesized DNA. Incorporation can then be measured by standard techniques such as by counting of radioisotope in a scintillation counter (e.g., Beckman LS 3800 Liquid Scintillation Counter).

Cell proliferation may also be assayed by colony formation in soft agar (Sambrook et al., Molecular Cloning, Cold Spring Harbor (1989)). For example, cells transformed with MARK are seeded in soft agar plates, and colonies are measured and counted after two weeks incubation.

Involvement of a gene in the cell cycle may be assayed by flow cytometry (Gray J W et al. (1986) Int J Radiat Biol Relat Stud Phys Chem Med 49:237-55). Cells transfected with a MARK may be stained with propidium iodide and evaluated in a flow cytometer (available from Becton Dickinson).

Accordingly, a cell proliferation or cell cycle assay system may comprise a cell that expresses a MARK, and that optionally has defective p53 function (e.g. p53 is over-expressed or under-expressed relative to wild-type cells). A test agent can be added to the assay system and changes in cell proliferation or cell cycle relative to controls where no test agent is added, identify candidate p53 modulating agents. In some embodiments of the invention, the cell proliferation or cell cycle assay may be used as a secondary assay to test a candidate p53 modulating agents that is initially identified using another assay system such as a cell-free kinase assay system. A cell proliferation assay may also be used to test whether MARK function plays a direct role in cell proliferation or cell cycle. For example, a cell proliferation or cell cycle assay may be performed on cells that over- or under-express MARK relative to wild type cells. Differences in proliferation or cell cycle compared to wild type cells suggests that the MARK plays a direct role in cell proliferation or cell cycle.

Angiogenesis. Angiogenesis may be assayed using various human endothelial cell systems, such as umbilical vein, coronary artery, or dermal cells. Suitable assays include Alamar Blue based assays (available from Biosource International) to measure proliferation; migration assays using fluorescent molecules, such as the use of Becton Dickinson Falcon HTS FluoroBlock cell culture inserts to measure migration of cells through membranes in presence or absence of angiogenesis enhancer or suppressors; and tubule formation assays based on the formation of tubular structures by endothelial cells on Matrigel® (Becton Dickinson). Accordingly, an angiogenesis assay system may comprise a cell that expresses a MARK, and that optionally has defective p53 function (e.g. p53 is over-expressed or under-expressed relative to wild-type cells). A test agent can be added to the angiogenesis assay system and changes in angiogenesis relative to controls where no test agent is added, identify candidate p53 modulating agents. In some embodiments of the invention, the angiogenesis assay may be used as a secondary assay to test a candidate p53 modulating agents that is initially identified using another assay system. An angiogenesis assay may also be used to test whether MARK function plays a direct role in cell proliferation. For example, an angiogenesis assay may be performed on cells that over- or under-express MARK relative to wild type cells. Differences in angiogenesis compared to wild type cells suggests that the MARK plays a direct role in angiogenesis.

Hypoxic induction. The alpha subunit of the transcription factor, hypoxia inducible factor-1 (HIF-1), is upregulated in tumor cells following exposure to hypoxia in vitro. Under hypoxic conditions, HIF-1 stimulates the expression of genes known to be important in tumour cell survival, such as those encoding glyolytic enzymes and VEGF. Induction of such genes by hypoxic conditions may be assayed by growing cells transfected with MARK in hypoxic conditions (such as with 0.1% 02, 5% CO2, and balance N2, generated in a NAPCO® 7001 incubator (Precision Scientific)) and normoxic conditions, followed by assessment of gene activity or expression by TAQMAN®. For example, a hypoxic induction assay system may comprise a cell that expresses a MARK, and that optionally has a mutated p53 (e.g. p53 is over-expressed or under-expressed relative to wild-type cells). A test agent can be added to the hypoxic induction assay system and changes in hypoxic response relative to controls where no test agent is added, identify candidate p53 modulating agents. In some embodiments of the invention, the hypoxic induction assay may be used as a secondary assay to test a candidate p53 modulating agent that is initially identified using another assay system. A hypoxic induction assay may also be used to test whether MARK function plays a direct role in the hypoxic response. For example, a hypoxic induction assay may be performed on cells that over- or under-express MARK relative to wild type cells. Differences in hypoxic response compared to wild type cells suggests that the MARK plays a direct role in hypoxic induction.

Cell adhesion. Cell adhesion assays measure adhesion of cells to purified adhesion proteins, or adhesion of cells to each other, in presence or absence of candidate modulating agents. Cell-protein adhesion assays measure the ability of agents to modulate the adhesion of cells to purified proteins. For example, recombinant proteins are produced, diluted to 2.5 g/mL in PBS, and used to coat the wells of a microtiter plate. The wells used for negative control are not coated. Coated wells are then washed, blocked with 1% BSA, and washed again. Compounds are diluted to 2× final test concentration and added to the blocked, coated wells. Cells are then added to the wells, and the unbound cells are washed off. Retained cells are labeled directly on the plate by adding a membrane-permeable fluorescent dye, such as calcein-AM, and the signal is quantified in a fluorescent microplate reader.

Cell-cell adhesion assays measure the ability of agents to modulate binding of cell adhesion proteins with their native ligands. These assays use cells that naturally or recombinantly express the adhesion protein of choice. In an exemplary assay, cells expressing the cell adhesion protein are plated in wells of a multiwell plate. Cells expressing the ligand are labeled with a membrane-permeable fluorescent dye, such as BCECF, and allowed to adhere to the monolayers in the presence of candidate agents. Unbound cells are washed off, and bound cells are detected using a fluorescence plate reader.

High-throughput cell adhesion assays have also been described. In one such assay, small molecule ligands and peptides are bound to the surface of microscope slides using a microarray spotter, intact cells are then contacted with the slides, and unbound cells are washed off. In this assay, not only the binding specificity of the peptides and modulators against cell lines are determined, but also the functional cell signaling of attached cells using immunofluorescence techniques in situ on the microchip is measured (Falsey J R et al., Bioconjug Chem. 2001 May-June; 12(3):346-53).

Primary Assays for Antibody Modulators

For antibody modulators, appropriate primary assays test is a binding assay that tests the antibody's affinity to and specificity for the MARK protein. Methods for testing antibody affinity and specificity are well known in the art (Harlow and Lane, 1988, 1999, supra). The enzyme-linked immunosorbant assay (ELISA) is a preferred method for detecting MARK-specific antibodies; others include FACS assays, radioimmunoassays, and fluorescent assays.

Primary Assays for Nucleic Acid Modulators

For nucleic acid modulators, primary assays may test the ability of the nucleic acid modulator to inhibit or enhance MARK gene expression, preferably mRNA expression. In general, expression analysis comprises comparing MARK expression in like populations of cells (e.g., two pools of cells that endogenously or recombinantly express MARK) in the presence and absence of the nucleic acid modulator. Methods for analyzing mRNA and protein expression are well known in the art. For instance, Northern blotting, slot blotting, ribonuclease protection, quantitative RT-PCR (e.g.,. using the TAQMAN®, PE APPLIED BIOSYSTEMS®), or microarray analysis may be used to confirm that MARK mRNA expression is reduced in cells treated with the nucleic acid modulator (e.g., Current Protocols in Molecular Biology (1994) Ausubel FM et al., eds., John Wiley & Sons, Inc., chapter 4; Freeman WM et al., Biotechniques (1999) 26:112125; Kallioniemi OP, Ann Med 2001, 33:142-147; Blohm DH and Guiseppi-Elie, A. Curr Opin Biotechnol 2001, 12:41-47). Protein expression may also be monitored. Proteins are most commonly detected with specific antibodies or antisera directed against either the MARK protein or specific peptides. A variety of means including Western blotting, ELISA, or in situ detection, are available (Harlow E and Lane D, 1988 and 1999, supra).

Secondary Assays

Secondary assays may be used to further assess the activity of MARK-modulating agent identified by any of the above methods to confirm that the modulating agent affects MARK in a manner relevant to the p53 pathway. As used herein, MARK-modulating agents encompass candidate clinical compounds or other agents derived from previously identified modulating agent. Secondary assays can also be used to test the activity of a modulating agent on a particular genetic or biochemical pathway or to test the specificity of the modulating agent's interaction with MARK.

Secondary assays generally compare like populations of cells or animals (e.g., two pools of cells or animals that endogenously or recombinantly express MARK) in the presence and absence of the candidate modulator. In general, such assays test whether treatment of cells or animals with a candidate MARK-modulating agent results in changes in the p53 pathway in comparison to untreated (or mock- or placebo-treated) cells or animals. Certain assays use "sensitized genetic backgrounds", which, as used herein, describe cells or animals engineered for altered expression of genes in the p53 or interacting pathways.

Cell-Based Assays

Cell based assays may use a variety of mammalian cell lines known to have defective p53 function (e.g. SAOS-2 osteoblasts, H1299 lung cancer cells, C33A and HT3 cervical cancer cells, HT-29 and DLD-1 colon cancer cells, among others, available from American Type Culture Collection (ATCC), Manassas, Va.). Cell based assays may detect endogenous p53 pathway activity or may rely on recombinant expression of p53 pathway components. Any of the aforementioned assays may be used in this cell-based format. Candidate modulators are typically added to the cell media but may also be injected into cells or delivered by any other efficacious means.

Animal Assays

A variety of non-human animal models of normal or defective p53 pathway may be used to test candidate MARK modulators. Models for defective p53 pathway typically use genetically modified animals that have been engineered to mis-express (e.g., over-express or lack expression in) genes involved in the p53 pathway. Assays generally require systemic delivery of the candidate modulators, such as by oral administration, injection, etc.

In a preferred embodiment, p53 pathway activity is assessed by monitoring neovascularization and angiogenesis. Animal models with defective and normal p53 are used to test the candidate modulator's affect on MARK in Matrigel® assays. Matrigel® is an extract of basement membrane proteins, and is composed primarily of laminin, collagen IV, and heparin sulfate proteoglycan. It is provided as a sterile liquid at 4° C., but rapidly forms a solid gel at 37° C. Liquid Matrigel® is mixed with various angiogenic agents, such as bFGF and VEGF, or with human tumor cells which over-express the MARK. The mixture is then injected subcutaneously (SC) into female athymic nude mice (Taconic, Germantown, N.Y.)

to support an intense vascular response. Mice with Matrigel® pellets may be dosed via oral (PO), intraperitoneal (IP), or intravenous (IV) routes with the candidate modulator. Mice are euthanized 5-12 days post-injection, and the Matrigel® pellet is harvested for hemoglobin analysis (Sigma plasma hemoglobin kit). Hemoglobin content of the gel is found to correlate the degree of neovascularization in the gel.

In another preferred embodiment, the effect of the candidate modulator on MARK is assessed via tumorigenicity assays. In one example, xenograft human tumors are implanted SC into female athymic mice, 6-7 week old, as single cell suspensions either from a pre-existing tumor or from in vitro culture. The tumors which express the MARK endogenously are injected in the flank, $1\times10^5$ to $1\times10^7$ cells per mouse in a volume of 100 μL using a 27 gauge needle. Mice are then ear tagged and tumors are measured twice weekly. Candidate modulator treatment is initiated on the day the mean tumor weight reaches 100 mg. Candidate modulator is delivered IV, SC, IP, or PO by bolus administration. Depending upon the pharmacokinetics of each unique candidate modulator, dosing can be performed multiple times per day. The tumor weight is assessed by measuring perpendicular diameters with a caliper and calculated by multiplying the measurements of diameters in two dimensions. At the end of the experiment, the excised tumors maybe utilized for biomarker identification or further analyses. For immunohistochemistry staining, xenograft tumors are fixed in 4% paraformaldehyde, 0.1M phosphate, pH 7.2, for 6 hours at 4° C., immersed in 30% sucrose in PBS, and rapidly frozen in isopentane cooled with liquid nitrogen.

Diagnostic and Therapeutic Uses

Specific MARK-modulating agents are useful in a variety of diagnostic and therapeutic applications where disease or disease prognosis is related to defects in the p53 pathway, such as angiogenic, apoptotic, or cell proliferation disorders. Accordingly, the invention also provides methods for modulating the p53 pathway in a cell, preferably a cell pre-determined to have defective p53 function, comprising the step of administering an agent to the cell that specifically modulates MARK activity. Preferably, the modulating agent produces a detectable phenotypic change in the cell indicating that the p53 function is restored, i.e., for example, the cell undergoes normal proliferation or progression through the cell cycle.

The discovery that MARK is implicated in p53 pathway provides for a variety of methods that can be employed for the diagnostic and prognostic evaluation of diseases and disorders involving defects in the p53 pathway and for the identification of subjects having a predisposition to such diseases and disorders.

Various expression analysis methods can be used to diagnose whether MARK expression occurs in a particular sample, including Northern blotting, slot blotting, ribonuclease protection, quantitative RT-PCR, and microarray analysis. (e.g., Current Protocols in Molecular Biology (1994) Ausubel F M et al., eds., John Wiley & Sons, Inc., chapter 4; Freeman W M et al., Biotechniques (1999) 26:112-125; Kallioniemi O P, Ann Med 2001, 33:142-147; Blohm and Guiseppi-Elie, Curr Opin Biotechnol 2001, 12:41-47). Tissues having a disease or disorder implicating defective p53 signaling that express a MARK, are identified as amenable to treatment with a MARK modulating agent. In a preferred application, the p53 defective tissue overexpresses a MARK relative to normal tissue. For example, a Northern blot analysis of mRNA from tumor and normal cell lines, or from tumor and matching normal tissue samples from the same patient, using full or partial MARK cDNA sequences as probes, can determine whether particular tumors express or overexpress MARK. Alternatively, the TaqMan® is used for quantitative RT-PCR analysis of MARK expression in cell lines, normal tissues and tumor samples (PE Applied Biosystems).

Various other diagnostic methods may be performed, for example, utilizing reagents such as the MARK oligonucleotides, and antibodies directed against a MARK, as described above for: (1) the detection of the presence of MARK gene mutations, or the detection of either over- or under-expression of MARK mRNA relative to the non-disorder state; (2) the detection of either an over- or an under-abundance of MARK gene product relative to the non-disorder state; and (3) the detection of perturbations or abnormalities in the signal transduction pathway mediated by MARK.

Thus, in a specific embodiment, the invention is drawn to a method for diagnosing a disease in a patient, the method comprising: a) obtaining a biological sample from the patient; b) contacting the sample with a probe for MARK expression; c) comparing results from step (b) with a control; and d) determining whether step (c) indicates a likelihood of disease. Preferably, the disease is cancer, most preferably a cancer as shown in TABLE 1. The probe may be either DNA or protein, including an antibody.

EXAMPLES

The following experimental section and examples are offered by way of illustration and not by way of limitation.

I. *Drosophila* p53 Screen

The *Drosophila* p53 gene was overexpressed specifically in the wing using the vestigial margin quadrant enhancer. Increasing quantities of *Drosophila* p53 (titrated using different strength transgenic inserts in 1 or 2 copies) caused deterioration of normal wing morphology from mild to strong, with phenotypes including disruption of pattern and polarity of wing hairs, shortening and thickening of wing veins, progressive crumpling of the wing and appearance of dark "death" inclusions in wing blade. In a screen designed to identify enhancers and suppressors of *Drosophila* p53, homozygous females carrying two copies of p53 were crossed to 5663 males carrying random insertions of a piggyBac transposon (Fraser M et al., Virology (1985) 145:356-361). Progeny containing insertions were compared to non-insertion-bearing sibling progeny for enhancement or suppression of the p53 phenotypes. Sequence information surrounding the piggyBac insertion site was used to identify the modifier genes. Modifiers of the wing phenotype were identified as members of the p53 pathway. kp78a was a suppressor of the wing phenotype. Human orthologs of the modifiers are referred to herein as MARK.

BLAST analysis (Altschul et al., supra) was employed to identify Targets from *Drosophila* modifiers. For example, representative sequences from MARK GI# 9845487 (SEQ ID NO:24), GI# 8923922(SEQ ID NO:25), GI# 4505103 (SEQ ID NO:27), and GI#13899225 (SEQ ID NO:29) share 43%, 65%, 65% and 45% amino acid identity, respectively, with the *Drosophila* kp78a.

Various domains, signals, and functional subunits in proteins were analyzed using the PSORT (Nakai K., and Horton P., Trends Biochem Sci, 1999, 24:34-6; Kenta Nakai, Protein sorting signals and prediction of subcellular localization, Adv. Protein Chem. 54, 277-344 (2000)), PFAM (Bateman A., et al., Nucleic Acids Res, 1999, 27:260-2;, SMART (Ponting CP, et al., SMART: identification and annotation of domains from signaling and extracellular protein sequences. Nucleic Acids Res. 1999 Jan 1;27(1):229-32), TM-HMM (Erik L.L. Sonnhammer, Gunnar von Heijne, and Anders Krogh: A hidden Markov model for predicting transmembrane helices in protein sequences. In Proc. of Sixth Int. Conf. on Intelligent Systems for Molecular Biology, p 175-182 Ed J. Glasgow, T. Littlejohn, F. Major, R. Lathrop, D. Sankoff, and C. Sensen Menlo Park, CA: AAAI Press, 1998), and dust (Renun M, and Sonnhammer E. Classification of transmembrane protein families in the Caenorhabditis elegans genome and identification of human orthologs. Genome Res. 2000 Nov;10(11):1679-89) programs. For example, the proten kinase domains of MARKs from GI#s 9845487 (SEQ ID NO:24), 8923922 (SEQ ID NO:25), 4505103 (SEQ ID NO:27), and 13899225 (SEQ ID NO:29) is located at approximately amino acid residues 20 to 271, 60 to 311, 56 to 307, and 59 to 310, respectively (PFAM 00069). Further, the ubiquitin associated (UBA/TS-N) domains of MARKs from GI#s 9845487 (SEQ ID NO:24), 8923922 (SEQ ID NO:25), 4505103 (SEQ ID NO:27), and 13899225 (SEQ ID NO:29) is located at approximately amino acid residues 291 to 330, 331 to 370, 327 to 366, and 330 to 369, respectively (PFAM 00627). Still further, the kinase associated domains from MARKs of GI#s9845487 (SEQ ID NO:24), 8923922 (SEQ ID NO:25), and 4505103 (SEQ ID NO:27) are located at approximately amino acid residues 696 to 745, 746 to 795, and 664 to 713, respectively (PFAM 02149).

II. High-Throughput In Vitro Fluorescence Polarization Assay

Fluorescently-labeled MARK peptide/substrate are added to each well of a 96-well microtiter plate, along with a test agent in a test buffer (10 mM HEPES, 10 mM NaCl, 6 mM magnesium chloride, pH 7.6). Changes in fluorescence polarization, determined by using a Fluorolite FPM-2 Fluorescence Polarization Microtiter System (Dynatech Laboratories, Inc), relative to control values indicates the test compound is a candidate modifier of MARK activity.

III. High-Throughput In Vitro Binding Assay $^{33}$P-labeled MARK peptide is added in an assay buffer (100 mM KCl, 20 mM HEPES pH 7.6, 1 mM $MgCl_2$, 1% glycerol, 0.5% NP-40, 50 mM beta-mercaptoethanol, 1 mg/ml BSA, cocktail of protease inhibitors) along with a test agent to the wells of a Neutralite-avidin coated assay plate and incubated at 25° C. for 1 hour. Biotinylated substrate is then added to each well and incubated for 1 hour. Reactions are stopped by washing with PBS, and counted in a scintillation counter. Test agents that cause a difference in activity relative to control without test agent are identified as candidate p53 modulating agents.

IV. Immunoprecipitations and Immunoblotting

For coprecipitation of transfected proteins, $3\times10^6$ appropriate recombinant cells containing the MARK proteins are plated on 10-cm dishes and transfected on the following day with expression constructs. The total amount of DNA is kept constant in each transfection by adding empty vector. After 24 h, cells are collected, washed once with phosphate-buffered saline and lysed for 20 min on ice in 1 ml of lysis buffer containing 50 mM Hepes, pH 7.9, 250 mM NaCl, 20 mM-glycerophosphate, 1 mM sodium orthovanadate, 5 mM p-nitrophenyl phosphate, 2 mM dithiothreitol, protease inhibitors (complete, Roche Molecular Biochemicals), and 1% Nonidet P-40. Cellular debris is removed by centrifugation twice at 15,000×g for 15 min. The cell lysate is incubated with 25 μl of M2 beads (Sigma) for 2 h at 4° C. with gentle rocking.

After extensive washing with lysis buffer, proteins bound to the beads are solubilized by boiling in SDS sample buffer, fractionated by SDS-polyacrylamide gel electrophoresis, transferred to polyvinylidene difluoride membrane and blotted with the indicated antibodies. The reactive bands are visualized with horseradish peroxidase coupled to the appropriate secondary antibodies and the enhanced chemiluminescence (ECL) Western blotting detection system (Amersham Pharmacia Biotech).

V. Kinase Assay

A purified or partially purified MARK is diluted in a suitable reaction buffer, e.g., 50 mM Hepes, pH 7.5, containing magnesium chloride or manganese chloride (1-20 mM) and a peptide or polypeptide substrate, such as myelin basic protein or casein (1-10 μg/ml). The final concentration of the kinase is 1-20 nM. The enzyme reaction is conducted in microtiter plates to facilitate optimization of reaction conditions by increasing assay throughput. A 96-well microtiter plate is employed using a final volume 30-100 μl. The reaction is initiated by the addition of $^{33}$P-gamma-ATP (0.5 μCi/ml) and incubated for 0.5 to 3 hours at room temperature. Negative controls are provided by the addition of EDTA, which chelates the divalent cation ($Mg2^+$ or $Mn^{2+}$) required for enzymatic activity. Following the incubation, the enzyme reaction is quenched using EDTA. Samples of the reaction are transferred to a 96-well glass fiber filter plate (MultiScreen, Millipore). The filters are subsequently washed with phosphate-buffered saline, dilute phosphoric acid (0.5%) or other suitable medium to remove excess radiolabeled ATP. Scintillation cocktail is added to the filter plate and the incorporated radioactivity is quantitated by scintillation counting (Wallac/Perkin Elmer). Activity is defined by the amount of radioactivity detected following subtraction of the negative control reaction value (EDTA quench).

VI. Expression Analysis

All cell lines used in the following experiments are NCI (National Cancer Institute) lines, and are available from ATCC$^{SM}$ (American Type Culture Collection, Manassas, VA 20110-2209). Normal and tumor tissues were obtained from Impath, UC Davis, CLONTECH™, STRATAGENE®, and AMBION®.

TAQMAN® analysis was used to assess expression levels of the disclosed genes in various samples.

RNA was extracted from each tissue sample using QIAGEN™(Valencia, CA) RNEASY® kits, following manufacturer's protocols, to a final concentration of 50ng/μl. Single stranded cDNA was then synthesized by reverse transcribing the RNA samples using random hexamers and 500ng of total RNA per reaction, following protocol 4304965 of APPLIED BIOSYSTEMS® (Foster City, CA,).

Primers for expression analysis using TAQMAN® assay APPLIED BIOSYSTEMS®, Foster City, CA) were prepared according to the TAQMAN® protocols, and the following criteria:

a) primer pairs were designed to span introns to eliminate genomic contamination, and b) each primer pair produced only one product. Expression analysis was performed using 7900HT instrument.

TAQMAN® reactions were carried out following manufacturer's protocols, in 25 μl total volume for 96-well plates and 10 μl total volume for 384-well plates, using 300 nM primer and 250 nM probe, and approximately 25 ng of cDNA. The standard curve for result analysis was prepared using a universal pool of human cDNA samples, which is a mixture of cDNAs from a wide variety of tissues so that the chance that a target will be present in appreciable amounts is good. The raw data were normalized using 18 S rRNA (universally expressed in all tissues and cells).

For each expression analysis, tumor tissue samples were compared with matched normal tissues from the same patient. A gene was considered overexpressed in a tumor when the level of expression of the gene was 2 fold or higher in the tumor compared with its matched normal sample.

Results are shown in Table 1. Data presented in bold indicate that greater than 50% of tested tumor samples of the tissue type indicated in row 1 exhibited over expression of the gene listed in column 1, relative to normal samples. Underlined data indicates that between 25% to 49% of tested tumor samples exhibited over expression. A modulator identified by an assay described herein can be further validated for therapeutic effect by administration to a tumor in which the gene is overexpressed. A decrease in tumor growth confirms therapeutic utility of the modulator. Prior to treating a patient with the modulator, the likelihood that the patient will respond to treatment can be diagnosed by obtaining a tumor sample from the patient, and assaying for expression of the gene targeted by the modulator. The expression data for the gene(s) can also be used as a diagnostic marker for disease progression. The assay can be performed by expression analysis as described above, by antibody directed to the gene target, or by any other available detection method.

TABLE 1

| | breast | | colon | | lung | | ovary | |
|---|---|---|---|---|---|---|---|---|
| GI#9845486 (SEQ ID NO: 1) | 7 | 11 | 8 | 30 | 8 | 13 | 5 | 7 |
| GI#9845488 (SEQ ID NO: 2) | 1 | 11 | 4 | 30 | 0 | 13 | 1 | 7 |
| GI#8923921 (SEQ ID NO: 8) | 2 | 11 | 7 | 30 | 6 | 13 | 0 | 7 |
| GI#3089348 (SEQ ID NO: 13) | 2 | 11 | 2 | 30 | 0 | 13 | 2 | 7 |
| GI#13366083 (SEQ ID NO: 19) | 2 | 11 | 2 | 30 | 5 | 13 | 1 | 7 |

What is claimed is:

1. A method for diagnosing ovarian cancer in a subject comprising:
   (a) obtaining a biological sample from a subject, wherein the biological sample is derived from ovarian tissue;
   (b) determining the level of expression of Microtubule Affinity Regulating Kinase 2 (MARK2) or Microtubule Affinity Regulating Kinase 3 (MARK3) in the biological sample of step (a), wherein the expression of MARK2 is determined by measuring the expression of SEQ ID NO: 1 or an encoded polypeptide thereof, and the expression of MARK3 is determined by measuring the expression of SEQ ID NO: 13 or an encoded polypeptide thereof;
   (c) comparing the level of expression of MARK2 or MARK3 in the biological sample of step (b) with the level of expression of MARK2 or MARK3, respectively, in a control sample; and
   (d) diagnosing ovarian cancer by detecting an elevated level of MARK2 or MARK3 expression in the biological sample compared with the control sample.

2. The method of claim 1, wherein the control sample is a non-cancerous sample derived from ovarian tissue.

3. The method of claim 1, wherein the level of MARK2 or MARK3 expression in the biological sample is at least 2-fold higher than the level of expression in the control sample.

4. The method of claim 1, wherein the level of MARK2 expression is determined using an anti-MARK2 antibody and the level of MARK3 expression is determined using an anti-MARK3 antibody.

5. The method of claim 1, wherein the level of MARK2 expression is determined using a MARK2 nucleic acid and the level of MARK3 expression is determined using a MARK3 nucleic acid.

6. A method for diagnosing breast or colon cancer in a subject comprising:
   (a) obtaining a biological sample from a subject, wherein the biological sample is derived from breast or colon tissue;
   (b) determining the level of expression of MARK2 in the biological sample of step (a), wherein the expression of MARK2 is determined by measuring the expression of SEQ ID NO: 1 or an encoded polypeptide thereof;
   (c) comparing the level of expression of MARK2 in the biological sample of step (b) with the level of expression of MARK2 in a control sample; and
   (d) diagnosing breast or colon cancer by determining an elevated level of expression of MARK2 in the biological sample compared with the control sample.

7. The method of claim 6, wherein the control sample is a non-cancerous sample derived from breast or colon tissue that matches that of the biological sample of the subject.

8. The method of claim 6, wherein the level of MARK2 expression in the biological sample is at least 2-fold higher than the level of expression in the control sample.

9. The method of claim 6, wherein the level of MARK2 expression is determined using an anti-MARK2 antibody.

10. The method of claim 6, wherein the level of MARK2 expression is determined using a MARK2 nucleic acid.

11. A method for diagnosing lung cancer in a subject comprising:
    (a) obtaining a biological sample from a subject, wherein the biological sample is derived from lung tissue;
    (b) determining the level of expression of Microtubule Affinity Regulating Kinase (MARK) in the biological sample of step (a), wherein the MARK is selected from MARK1, MARK2, and MARKL1 and wherein the expression of MARK1, MARK2, or MARKL1 is determined by measuring the expression of SEQ ID NO: 8, SEQ ID NO:1, or SEQ ID NO: 19, respectively, or an encoded polypeptide of SEQ ID NO: 8, SEQ ID NO:1, or SEQ ID NO: 19, respectively;
    (c) comparing the level of expression of MARK1, MARK2, or MARKL1 in the biological sample of step (b) with the level of expression of MARK1, MARK2, or MARKL1, respectively, in a control sample; and
    (d) diagnosing lung cancer by determining an elevated level of expression of MARK1, MARK2, or MARKL1 in the biological sample compared with the control sample.

12. The method of claim 11, wherein the control sample is a non-cancerous sample derived from lung tissue.

13. The method of claim 11, wherein the level of MARK1, MARK2, or MARKL1 expression in the biological sample is at least 2-fold higher than the level of expression in the control sample.

14. The method of claim 11, wherein the level of MARK1, MARK2, or MARKL1 expression is determined using an anti-MARK1 antibody, an anti-MARK2 antibody, or an anti-MARKL1 antibody, respectively.

15. The method of claim 11, wherein the level of MARK1, MARK2, or MARKL1 expression is determined using a MARK1 nucleic acid, a MARK2 nucleic acid, or a MARKL1 nucleic acid, respectively.

* * * * *